United States Patent [19]
Lichter et al.

[11] Patent Number: 6,159,147
[45] Date of Patent: *Dec. 12, 2000

[54] PERSONAL COMPUTER CARD FOR COLLECTION OF REAL-TIME BIOLOGICAL DATA

[75] Inventors: Patrick A. Lichter, Plymouth; Spencer J. Lien, Medina, both of Minn.

[73] Assignee: QRS Diagnostics, LLC, Plymouth, Minn.

[*] Notice: This patent is subject to a terminal disclaimer.

[21] Appl. No.: 09/173,059

[22] Filed: Oct. 15, 1998

Related U.S. Application Data

[63] Continuation-in-part of application No. 08/810,632, Feb. 28, 1997, Pat. No. 5,827,179.

[51] Int. Cl.[7] .................................................. A61B 5/00
[52] U.S. Cl. ..................... 600/300; 600/301; 600/323; 600/538; 600/544; 600/546; 600/481; 128/920
[58] Field of Search ..................... 600/300, 301, 600/309, 323, 529, 537, 538, 544, 546, 549, 481, 308, 364; 128/920

[56] References Cited

U.S. PATENT DOCUMENTS

| | | | |
|---|---|---|---|
| 5,307,263 | 4/1994 | Brown | 600/301 |
| 5,623,925 | 4/1997 | Swenson et al. | 600/301 |
| 5,701,894 | 12/1997 | Cherry et al. | 600/300 |
| 5,827,179 | 10/1998 | Lichter et al. | 600/300 |

*Primary Examiner*—Eric F. Winakur
*Attorney, Agent, or Firm*—Stout, Uka, Buyan & Mullins, LLP; Kenton R. Mullins; Frank J. Uka

[57] ABSTRACT

A real-time biological data processing PC card is lightweight, cost effective, and portable. The real-time biological data processing PC card is capable of converting a host personal computer system into a powerful diagnostic instrument. Each real-time biological data processing PC card is adapted to input and process biological data from one or more biological data sensors, and is interchangeable with other real-time biological data processing PC cards. A practitioner having three different real-time biological data processing PC cards, for example, each one corresponding to a different biological data collection device, effectively carries three full-sized, powerful diagnostic instruments. The full resources of a host personal computer can be utilized and converted into a powerful diagnostic instrument, for each biological data collection device, by the insertion of one of the real-time biological data processing PC cards.

163 Claims, 26 Drawing Sheets

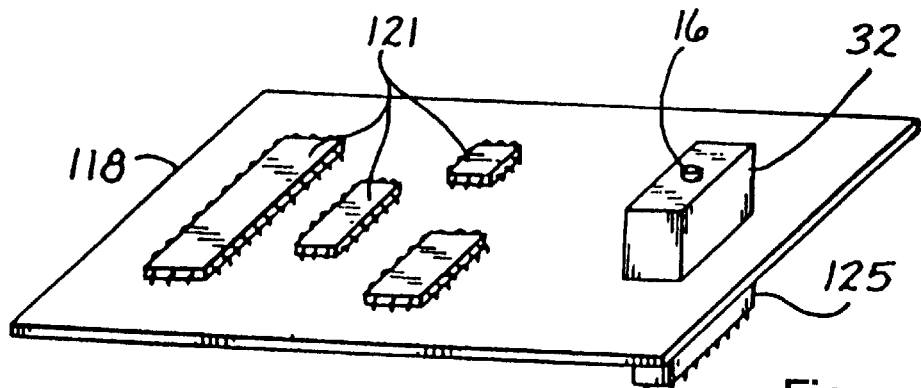
Figure 6a
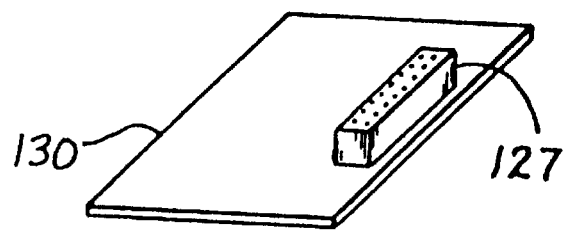
Figure 6b
Figure 7
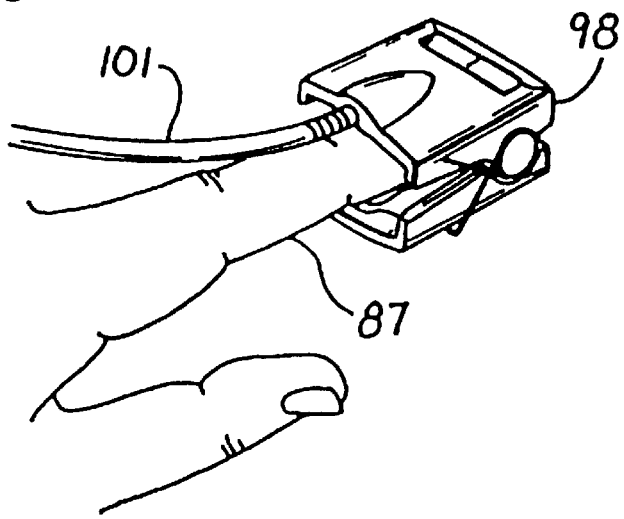

PERSONAL COMPUTER CARD FOR COLLECTION OF REAL-TIME BIOLOGICAL DATA

This application is a continuation-in-part of U.S. application Ser. No. 08/810,632, entitled PERSONAL COMPUTER CARD FOR COLLECTION OF REAL-TIME BIOLOGICAL DATA, which is commonly assigned and the contents of which are expressly incorporated herein by reference, filed Feb. 28, 1997 now U.S. Pat. No. 5,827,179.

BACKGROUND OF THE INVENTION

1. Field of the Invention

The present invention relates generally to personal computer (PC) cards and, more particularly, to PC cards for use in combination with personal computers for collecting biological data on a real-time basis.

2. Description of Related Art

The United States health care system is currently in the midst of a transformation away from specialized medicine toward a more cost-conscious, primary-care oriented system. Devices having cost-effective means for diagnosing and monitoring patients are expected to gain prominence in the market place. Many current data acquisition devices exist in the medical industry, but few, if any, of these devices are economical, extremely lightweight and portable, accurate, versatile, and interchangeable with other biological data collection devices.

One prior art device, manufactured by the assignee of the present application, incorporates a diagnostic box which is adapted to interface with a serial port of a personal computer. This diagnostic box is manufactured with a relatively expensive housing, having a size approximately equal to that of a book, an alternating current (AC) chord and power adapter, a serial port cable, a microprocessor, and other hardware elements.

The diagnostic box allows a user to perform real-time spirometry operations, while harnessing the PC computer's display, keyboard, printer, and other items. The PC computer display instructs the user with selectable patient incentives, and user-customized reports can be generated. The display of the personal computer can be configured to display volume-versus-time and flow-versus-volume curves. Additionally, parameters such as maximum exhale volume, maximum inhale volume and maximum flow rate can be computed and displayed on the personal computer display.

Data acquisition cards have existed in the prior art for transferring electrical signals from a data sensor through the data acquisition card and into a personal computer. These data acquisitions cards have been configured into Personal Computer Memory Card International Association (PCMCIA) cards.

Prior art data acquisition cards are often configured to measure potential signals ranging from zero to ten volts, and are often configured with twelve bit accuracy. A typical prior art data acquisition card may comprise a 30 pin connector and a cable, which is connected to a connector board. The connector board allows a user to hook up various signals thereto. In addition to the relatively high-voltage signal range (zero to ten volts), low-accuracy (e.g. twelve bits), extra hardware (30 pin connector, cable, and a connector board), and additional optional hardware, these prior art data acquisition cards are configured with a plurality of inputs and outputs and, further, are not adapted to convert a personal computer into a powerful biological data signal collecting, processing, and monitoring system.

Prior art data acquisition cards are not adapted for performing spirometry collection and analysis, since these cards are not equipped with pressure transducers for converting pressure signals into electrical signals. Even if these prior art data acquisition cards were equipped with pressure transducers, the cards would not be equipped with high-precision low-voltage signal collection and conditioning circuitry. A prior art data acquisition card, additionally, would not be suitable for other biological data collection and processing purposes, such as Electrocardiography (ECG) biological data collection, since these prior art data acquisition cards are not equipped with any insulating means for insulating a patient from potential shock, which may be delivered from the data acquisition card to the patient.

Another prior art device is disclosed in U.S. Pat. No. 5,549,115 to Morgan et al. The Morgan et al. patent generally discloses a PCMCIA format card which is adapted to perform as a data storage device, similarly to a floppy disc storage device. The PCMCIA format cart of Morgan et al. is equipped with a real-time clock for providing time and date data to the host system, in order to synchronize the host system time with the time of which the data was actually acquired. The PCMCIA format card of Morgan et al. does not provide any means for real-time data collection and processing and, accordingly, is not suitable for converting a host PC computer into a real-time biological data signal collection, processing, and monitoring system. The system of the Morgan et al. patent requires a separate dedicated computer device for acquiring the data, and a separate personal computer device for processing the data at a later time.

U.S. Pat. No. 5,546,432 to Thomson discloses a spirometer which includes control electronics located remotely from a hand-held housing. Communication between the hand-held housing, which includes an analog-to-digital (A/D) converter and an amplifier, occurs through a cable. A dedicated microprocessor including a simple keyboard structured and adapted specifically to control the operation of a spirometer is included in the Thomson device. The handle-shaped housing of the Thomson patent is quite different from a PC card.

A need exists in the prior art for real-time biological data signal collecting, processing, and monitoring systems, which are extremely lightweight and portable. The prior art has not introduced any cost-effective PC card, which is adapted to convert a host personal computer into any of a variety of real-time data collecting and processing systems.

SUMMARY OF THE INVENTION

The real-time biological data processing PC card of the present invention is very lightweight, cost effective, and portable. The real-time biological data processing PC card of the present invention is capable of converting a host personal computer system into a powerful diagnostic instrument. Each real-time biological data processing PC card is adapted to input and process biological data from one or more biological data sensors, and is interchangeable with other real-time biological data processing PC cards. A practitioner having three different real-time biological data processing PC cards, each one corresponding to a different biological data collection device, effectively carries three full-sized, powerful diagnostic instruments. The full resources of a host personal computer may be utilized and converted into a powerful diagnostic instrument, for each biological data collection device, by the insertion of one of the real-time biological data processing PC cards.

A portable computer card for collecting biological data, according to the present invention, includes a pressure transducer adapted to receive an air pressure from an air tube and to convert the air pressure into an electrical signal. The portable computer card includes an analog-to-digital converter adapted to receive and digitize the electrical signal, and a portable computer card interface adapted to provide an interface between the portable computer card and a host microprocessor system. The portable computer card interface may comprise a PCMCIA card interface. An amplifier, which is adapted to receive and amplify the electrical signal from the pressure transducer, is disposed between the pressure transducer and the analog-to-digital converter. The amplified electrical signal is related to the air pressure. The portable computer card further includes a housing, which is adapted for holding the pressure transducer, the amplifier, the analog-to-digital converter, and the portable computer card interface. A pressure input port is disposed on the housing. This pressure input port is in fluid communication with the pressure transducer and is adapted to receive an air pressure from an air tube. The portable computer card further includes a flexible air passageway, which is integrally connected to the housing, and which is adapted to supply an air pressure to the pressure input port.

According to still another aspect of the present invention, a portable biological data collection device includes a portable computer card housing, a biological data receiver, signal conditioning circuitry, and a portable computer card interface. The biological data receiver is adapted to receive biological data and to output the biological data, and the signal conditioning circuitry is adapted to receive the biological data from the biological data receiver and to convert the biological data into digitized biological data. The portable computer card interface is disposed within the portable computer card housing, and is adapted to communicate with a host computer to relay the digitized biological data to the host computer on a real-time basis as the biological data is converted by the signal conditioning circuitry.

The biological data receiver can be adapted to receive biological data from a pulse oximetry sensor, which is located externally of the portable biological data collection device. The biological data receiver can further be adapted to receive biological data from an ECG sensor. The biological data sensor is adapted to output low-amplitude signals on an order of one millivolt. The digitized data from the analog-to-digital converter preferably has a resolution greater than 12 bits and, preferably, has a resolution of 16 bits. The biological data sensor may further include a spirometer air tube.

According to another aspect of the present invention, a host computer is configurable among a plurality of biological data collection device modes. The host computer includes a portable computer card slot adapted to receive a portable computer card therein, a portable computer card interface adapted to communicate with a portable computer card inserted into the portable computer card slot, a microprocessor, a data bus, and input means for receiving designation data from a portable computer card within the portable computer card slot. The portable computer card interface is adapted to receive digitized biological data from a portable computer card inserted into the portable computer card slot, and the input means is operatively connected to the microprocessor. The designation data is indicative of a type of digitized biological data from a portable computer card inserted into the portable computer card slot. The designation data may comprise either a first identifier for indicating that the digitized biological data should be interpreted by the microprocessor as spirometer-pressure data or a second identifier indicating that the digitized biological data should be interpreted by the microprocessor as pulse oximetry electrical data. The host computer includes configuration means for configuring the host computer into a real-time spirometer-pressure data collecting and analyzing device upon receipt of the first identifier, and for configuring the host computer into a real-time pulse oximetry electrical data collecting and analyzing device upon receipt of the second identifier. The host computer may also be configured into an ECG data collection device mode, upon receipt of a third identifier from the input means. Additionally, the host computer may be configured among various other biological data collection device modes, upon receipt of additional identifiers.

According to yet another aspect of the present invention, a combination of a plurality of interchangeable biological data portable computer cards includes a spirometer portable computer card and a pulse oximetry portable computer card. The spirometer portable computer card and the pulse oximetry portable computer card are both insertable into a personal computer system, and are interchangeable. The spirometer portable computer card is adapted to convert the host computer into a spirometer data collecting and analyzing device, and the pulse oximetry portable computer card is adapted to convert the host computer into a pulse oximetry data collecting and analyzing device. The combination of interchangeable biological data portable computer cards may further include an ECG portable card, as well as other computer cards, each being adapted to convert the host personal computer into a different type of biological data collecting and analyzing device.

According to another aspect of the present invention, a portable computer card for delivering biological data to a host computer includes a portable computer card housing, at least one conductor connected to the portable computer card housing, an amplifier operatively connected to the at least one conductor, a power source operatively connected to the amplifier, and insulating means for providing electrical insulation between the power source and the conductor. The conductor is adapted to collect biological data from a patient, and the amplifier is adapted to receive the biological data and to output an amplified signal. The insulating means may comprise an optical translator, and can be positioned between the conductor and the amplifier. The portable computer card further includes an analog-to-digital converter for digitizing the amplified signal, and a portable computer card interface for providing a communication link between the portable computer card and a host personal computer system. The portable computer card interface is adapted to relay the digitized amplified signal to the host computer on a real-time basis, as biological data is collected from a patient. The power source comprises a conductor, which is adapted for receiving power from the host personal computer.

The present invention, together with additional features and advantages thereof, may best be understood by reference to the following description taken in connection with the accompanying illustrative drawings.

BRIEF DESCRIPTION OF THE DRAWINGS

FIG. 1a illustrates an end view of the real-time biological data processing PC card of FIG. 1, taken from the direction of the line 1a–1a;

FIG. 6a illustrates a simplified perspective view of the main circuit board of the real-time biological data processing PC card according to the present invention;

FIG. 6b illustrates a pulse oximeter module circuit board according to the present invention;

FIG. 7 illustrates an articulated finger clip sensor according to the present invention;

DETAILED DESCRIPTION OF THE PRESENTLY PREFERRED EMBODIMENTS

Figure 1A:
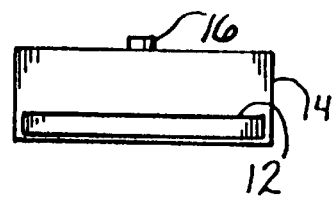
Figure 1B:
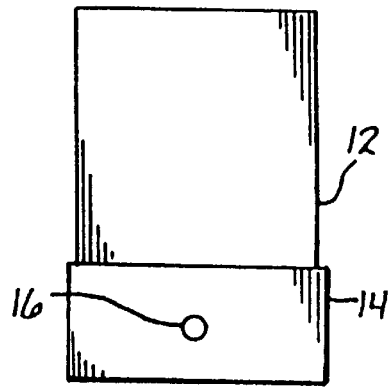
FIG. 1b illustrates a top planar view of the real-time biological data processing PC card, without the air tube connection.
Figure 1:
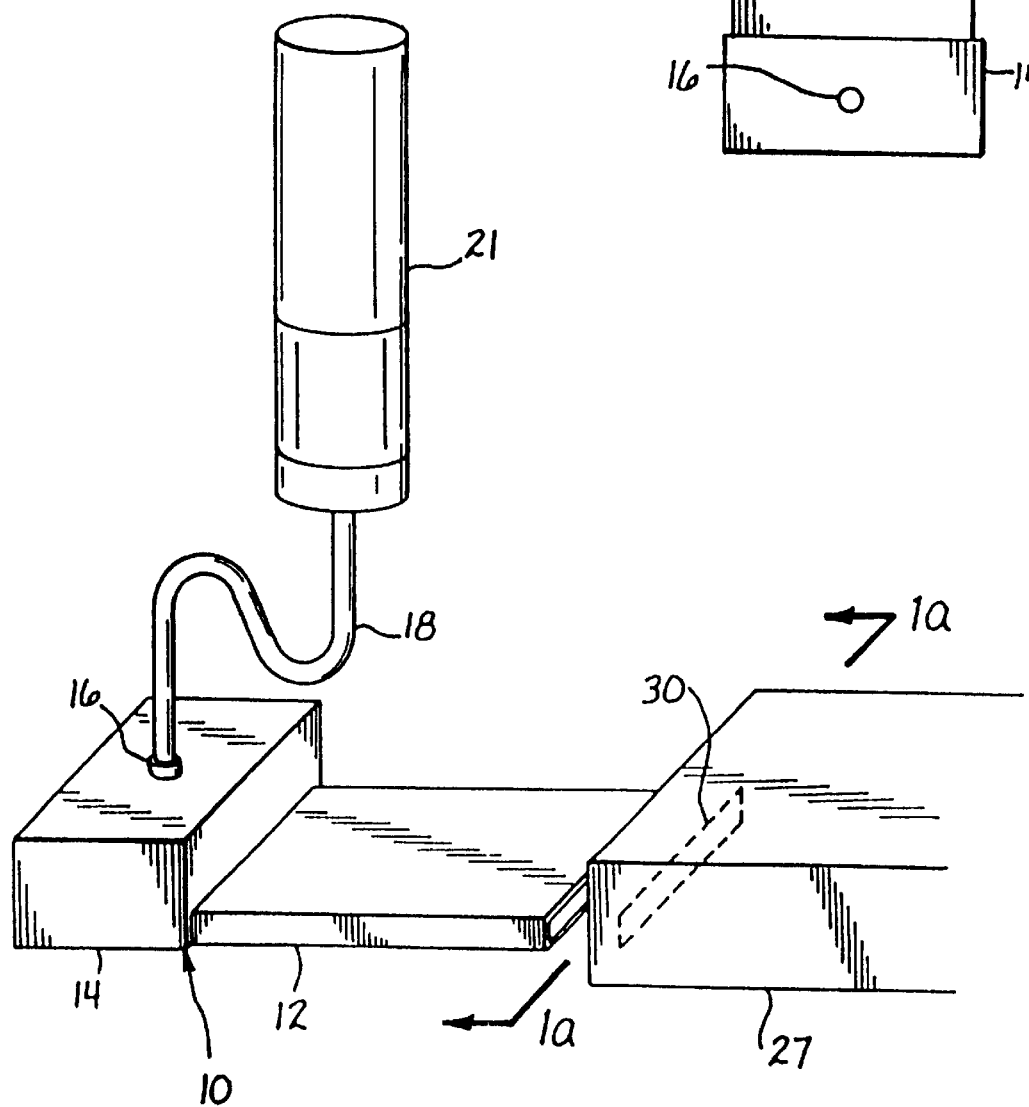
FIG. 1 illustrates a real-time biological data processing PC card according to the present invention.

Turning to FIG. 1, a real-time biological data processing PC card 10 is illustrated having a Personal Computer Memory Card International Association (PCMCIA) format housing 12 and a pressure transducer housing 14. The pressure transducer housing 14 preferably comprises a pressure input port 16, which is adapted to removably accommodate a flexible air passageway 18. A disposable spirometry mouthpiece 21 is attached to one end of the flexible air passageway 18, and a connector is attached to the other end of the flexible air passageway 18. As presently embodied, the connector comprises a truncated, conical shape which is adapted for matingly fitting within the pressure input port 16. After a user breaths into the disposable spirometry mouthpiece 21, the flexible air passageway 18 and the disposable spirometry mouthpiece 21 may be removed from the pressure input port 16, and discarded. In the below description and claims, the term "spirometry" is intended to encompass not only the general meaning of the word, but also to broadly encompass any other pulmonary function which can be detected by measuring air flow, pressure or volume.

The PCMCIA format housing 12 of the real-time biological data processing PC card 10 is preferably configured to conform with PCMCIA dimensional standards. As presently preferred, the PCMCIA format housing has a width of approximately 2.95 inches. The PCMCIA format housing 12 preferably comprises a length of approximately 3.40 inches. The pressure transducer housing 14, according to the presently preferred embodiment, has dimensions which are larger than PCMCIA conventions permit. As presently embodied, the pressure transducer housing 14 comprises a height of approximately 1 inch. These enlarged dimensions of the pressure transducer housing 14 facilitate placement of biological sensor circuitry, such as, for example, a pressure transducer.

FIG. 1*a* illustrates an end view of the real-time biological data processing PC card 10, taken from a view along the line 1*a*–1*a* of FIG. 1, and FIG. 1*b* illustrates a top-planar view of the real-time biological data processing PC card 10. A host personal computer 27 comprises a PCMCIA format slot 30, which is sized and dimensioned according to PCMCIA dimensional standards, in order to facilitate insertion of the PCMCIA format housing 12 therein.

Figure 2:
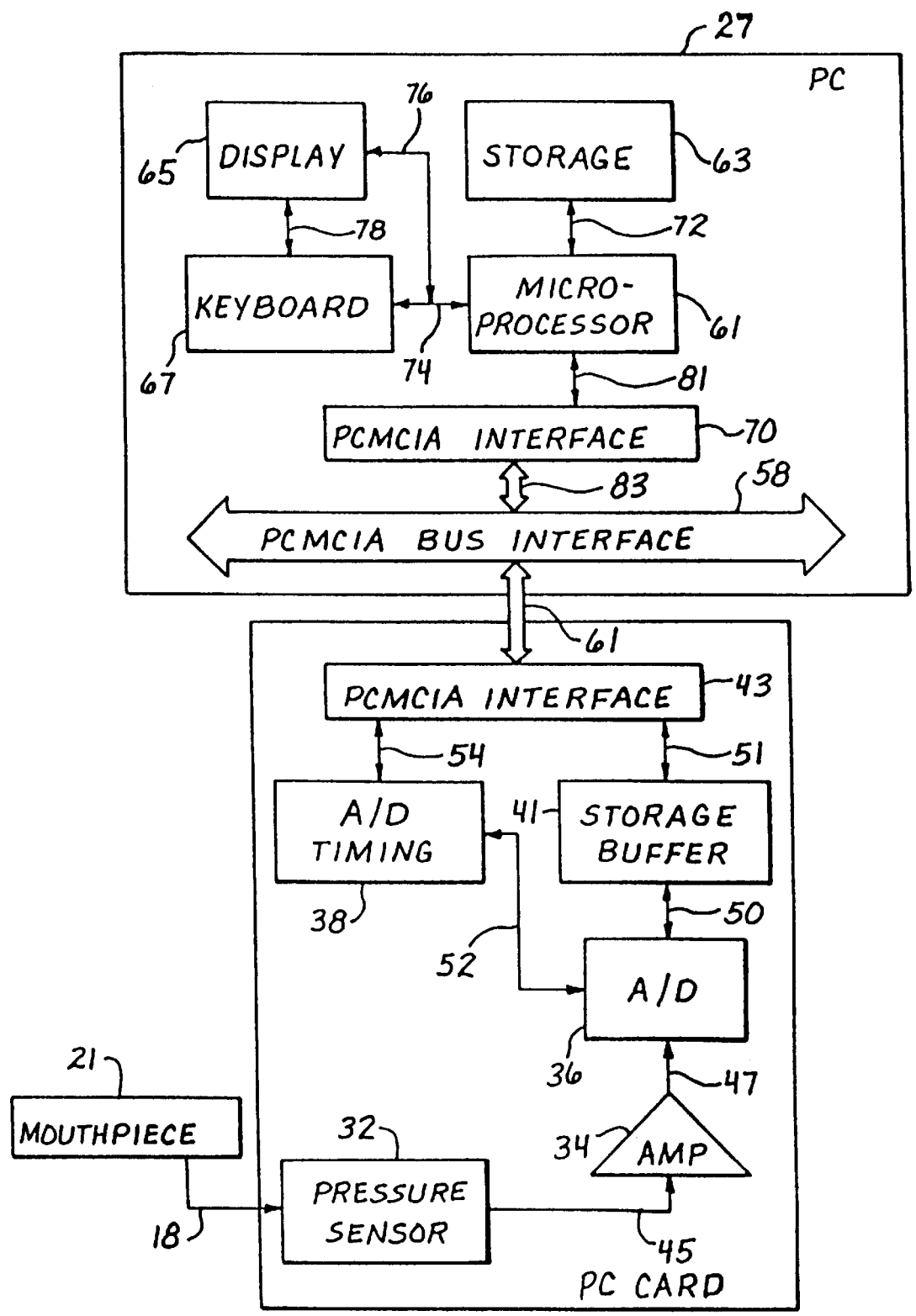
FIG. 2 illustrates a schematic block diagram of the circuitry of the real-time biological data processing PC card and a host personal computer system, according to the present invention.

FIG. 2 illustrates a schematic block diagram of components associated with the real-time biological data processing PC card 10 and the host personal computer 27. The real-time biological data processing PC card 10 comprises a pressure sensor 32, an amplifier 34, an analog-to-digital converter 36, an analog-to-digital timing circuit 38, a storage buffer 41, and a PCMCIA interface 43. The flexible air passageway 18 connects the disposable spirometry mouthpiece 21 to the pressure sensor 32, and a conductor path 45 connects the pressure sensor 32 to the amplifier 34. The amplifier 34 is connected to the analog-to-digital converter 36 via a conductor path 47, and the analog-to-digital converter 36 is connected to the storage buffer 41 via a conductor path 50. A conductor path 52 connects the analog-to-digital converter 36 to the analog-to-digital timing circuit 38, and a conductor path 54 connects the analog-to-digital timing circuit 38 to the PCMCIA interface 43. The storage buffer 41 is connected to the PCMCIA interface 43 via a conductor path 51. Upon insertion of the real-time biological data processing PC card 10 into the PCMCIA format slot 30, the PCMCIA interface 43 is connected to a PCMCIA bus interface 58 via a bus 61.

The host personal computer 27 comprises a microprocessor 61, a storage 63, a display 65, a keyboard 67, and a PCMCIA interface 70. The host personal computer 27, of course, may comprise other components which are not shown in FIG. 2. The microprocessor 61 is connected to the storage 63 via a bus 72, and is connected to the keyboard 67 via a bus 74. A bus 76 connects the display 65 to the bus 74, and a bus 78 connects the display 65 to the keyboard 67. The microprocessor 61 is connected tot he PCMCIA interface 70 via a bus 81, and the PCMCIA interface 70 is connected to the PCMCIA bus interface 58 via a bus 83.

When the real-time biological data processing PC card 10 and the host personal computer 27 are configured as shown in FIG. 2, communication between the devices 10 and 27 can occur via standardized PCMCIA protocols. The PCMCIA Developer's Guide—2nd Edition, published by Sycard Technology in 1994, the contents of which are expressly incorporated herein by reference, discloses information on PCMCIA conventions and protocols.

Although the embodiment of FIG. 2 is shown comprising a pressure sensor 32 and a disposable spirometry mouthpiece 21, any biological data sensor and/or associated components may be incorporated into the real-time biological data processing PC card 10 in accordance with the present invention.

In one embodiment, each biological data sensor, having a different format of biological data, is configured in a separate real-time biological data processing PC card. The various real-time biological data processing PC cards are interchangeable, to thereby configure the host personal computer 27 into various real-time biological data collecting and processing modes. Alternatively, a single real-time biological data processing PC card 10 may be configured to accommodate one or more different types of biological data sensors. According to the present invention, various interchangeable real-time biological data processing PC cards can configure the host personal computer 27 into various collecting, processing, and monitoring modes, including spirometry, electrocardiography (including resting, 24-hour, stress testing, signal averaging, event ECG, and heart-rate variability), blood pressure, body temperature, electroencephalograhy (EEG), echocardiography, Doppler, pulse oximetry (SPO2), sleep analysis, tcPO2, tcPCO2, nitrogen dioxide, capnography, respiratory rate, pulse rate, polysomnography, carbon monoxide, gastroesophageal pH, hydrogen, nitric oxide, bio-impedance, glucometer, audiometry, plethysmograph, weight, electromyography, urometry, and tympanometry, for example. The term "bio-impedance" is intended to include the general meaning of the term "bio-impedance" and to also include body composition analysis, cardiac output or any other bio-impedance analysis. Other biological data may also be collected and processed by the host personal computer 27, after being configured by a corresponding real-time biological data processing PC card.

The real-time biological data processing PC card 10 shown in FIG. 2, which is adapted for configuring the host personal computer 27 for spirometry procedures, receives a pressure signal from the mouth piece 21. The pressure sensor 32, which preferably comprises a pressure transducer, converts the pressure signal into an electrical signal, which is amplified by the amplifier 34. The analog-to-digital converter 36, which is timed by the analog-to-digital timing circuit 38, receives the amplified biological data from the amplifier 34, and digitizes the biological data. The analog-to-digital timing circuit 38 provides a timing signal, which facilitates sampling of the amplified biological data on the conductor path 47. This digitized biological data is output onto the conductor path 50. The storage buffer 41 receives the digitized biological data, and outputs this digitized biological data onto a conductor path 51, where the digitized biological data is made available to the PCMCIA interface 43. The storage buffer 41 preferably comprises a first in first out (FIFO) buffer, and may be omitted for simple configurations where buffering capabilities are not needed. The real-time biological data processing PC card 10 further comprises control circuitry, and the PCMCIA interface 43 preferably comprises input output (I/O) interface glue logic and an input output connector.

Upon insertion of the real-time biological data processing PC card 10 into the PCMCIA format slot 30 of the host computer 27, the microprocessor 61, the PCMCIA interface 70 of the host computer 27, and the PCMCIA interface 43 of the real-time biological data processing PC card 10 begin communicating via established PCMCIA format conventions. The microprocessor 61 determines the type of real-time biological data processing PC card which has been inserted into the PCMCIA format slot 30. In the illustrated case of FIG. 2, designation data from the PCMCIA interface 43 indicates to the microprocessor 61 that a spirometry-type real-time biological data processing PC card 10 has been inserted. Designation data from the PCMCIA interface 43 may, alternatively, identify the real-time biological data processing PC card 10 as being adapted for relaying oximetry, ECG, or other biological data to the host personal computer 27. As an alternative to, or in addition to, the illustrated embodiment of FIG. 2, a user may input designation data via the keyboard 67 or the display 65, indicating the type of real-time biological data processing PC card 10 which has been inserted into the PCMCIA format slot 30 of the host personal computer 27.

After the host personal computer 27 has "set up" the real-time biological data processing PC card 10, the host personal computer 27 prompts, via the display 65, the user to begin the spirometry test. As presently embodied, multi-media devices, such as entertaining displays and sounds, are implemented by the host personal computer 27 in order to educate the patient on how to perform the biological data test. The display 65 prompts the patient to begin the test, and coaches the patient during the test with, for example, entertaining incentives. This multi-media instructional system is configured to assist patients, especially in home disease management situations, helping asthmatics and cystic fibrosis patients, for example, comply with testing protocols. Additionally, the system of the present invention may reduce the need for skilled human interaction in order to achieve successful administration of the biological data tests.

The biological data from the pressure sensor 32, after being processed by the amplifier 34 and the analog-to-digital converter 36, is preferably immediately transferred from the PCMCIA interface 43 of the real-time biological data processing PC card 10 to the PCMCIA interface 70 of the host personal computer 27. The host personal computer 27, having received designation data indicating that the real-time biological data processing PC card 10 is a spirometry real-time biological data processing PC card, is configured to function as a complete spirometry data collecting, processing, and monitoring device. For example, a volume-versus-time wave form or a flow-versus-volume curve may be displayed on the display 65, indicating the real-time biological data received by the pressure sensor 32. A number of other parameters, such as maximum exhale volume, maximum inhale volume, and maximum flow rate, to name a few, may also be shown on the display 65 of the host personal computer 27. This data also may be compiled and printed in a variety of analytical and comparative formats.

Figure 3:
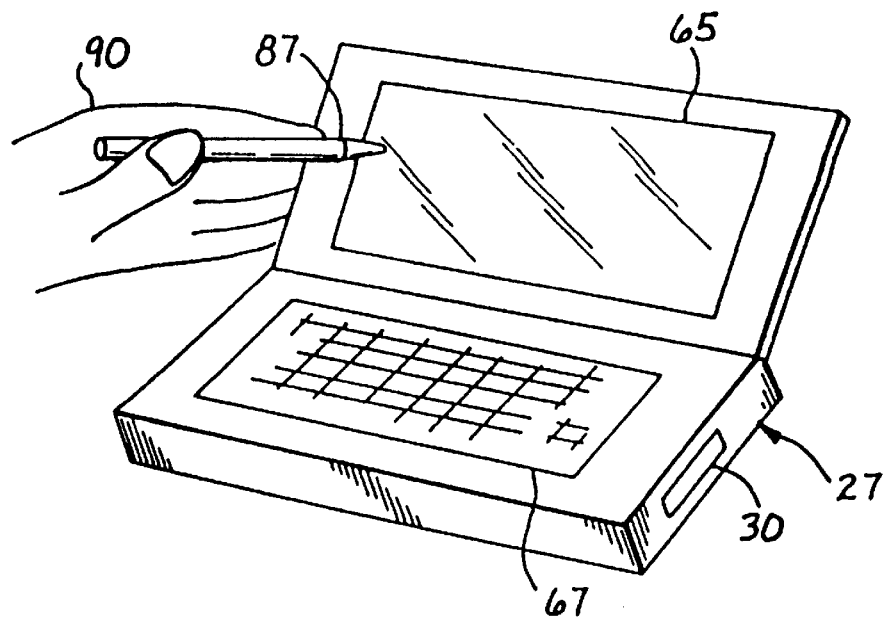
FIG. 3 illustrates a host-personal computer system according to the present invention.

FIG. 3 illustrates a host personal computer 27, according to the presently preferred embodiment. The host personal computer 27 preferably comprises a Personal Digital Assistant (PDA). The host personal computer 27 may comprise any desktop of laptop computer, as well. When the host personal computer 27 comprises a personal digital assistant, as presently preferred, Windows® CE (Pegasus) software is preferably used. This software preferably operates on the Windows® CE operating system. Other commercially available software packages, or customized software packages, may be used with the present invention. A pointing device 87, held by the hand 90 of a user, may be used to input data into the host personal computer 27 via a touch sensitive display 65. The host personal computer 27, having the real-time biological data processing PC card 10 of FIG. 1 inserted therein, is configured into a powerful diagnostic spirometry data collecting and analyzing instrument. Since the real-time biological data processing PC card 10 uses the keyboard 67, display 65, storage 63, microprocessor 61, power supply (not shown), and data transmission and printing capabilities (not shown) of the host computer system 27, the real-time biological data processing PC card 10 itself is very inexpensive and rudimentary in design. Yet, the real-time biological data processing PC card 10 is very powerful. The software loaded within the host personal computer 27 is preferably configured to allow the real-time biological data processing PC card 10 to interface, via PCMCIA format, with any other of a variety of personal computers, such as a desktop personal computer, or a notebook personal computer, for example.

The host personal computer 27 can transmit data via any conventional means, such as a serial port cable or a modem connection through an RJ11 phone plug. Data may be transmitted over the Internet, for example. In home disease management, for example, the host personal computer 27 can be configured to gather, process, and transmit additional information on the patient's medication, diet, symptoms, and other parameters. The combination of elements of the present invention thus provides a very portable, lightweight, and inexpensive means for diagnosing and monitoring patients.

Figure 4:
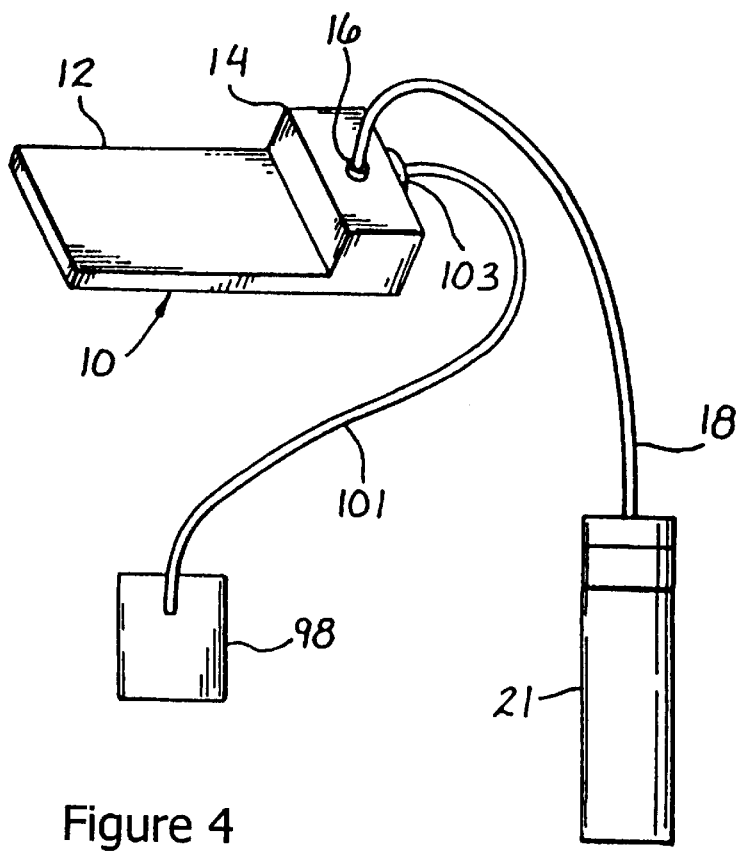
FIG. 4 illustrates a real-time biological data processing PC card according to the present invention.

FIG. 4 illustrates a real-time biological data processing PC card 10, having both a disposable spirometry mouthpiece 21 and a pulse oximeter finger clip 98. Like components are designated with like reference numbers. As with the embodiment of FIG. 1, the disposable spirometry mouthpiece 21 is connected to pressure transducer housing 14 via a flexible air passageway 18 and a pressure input port 16. The pulse oximeter finger clip 98 is connected to the pressure transducer housing 14 via a pulse oximeter cable 101, which transitions into a connector 103.

Figure 5:
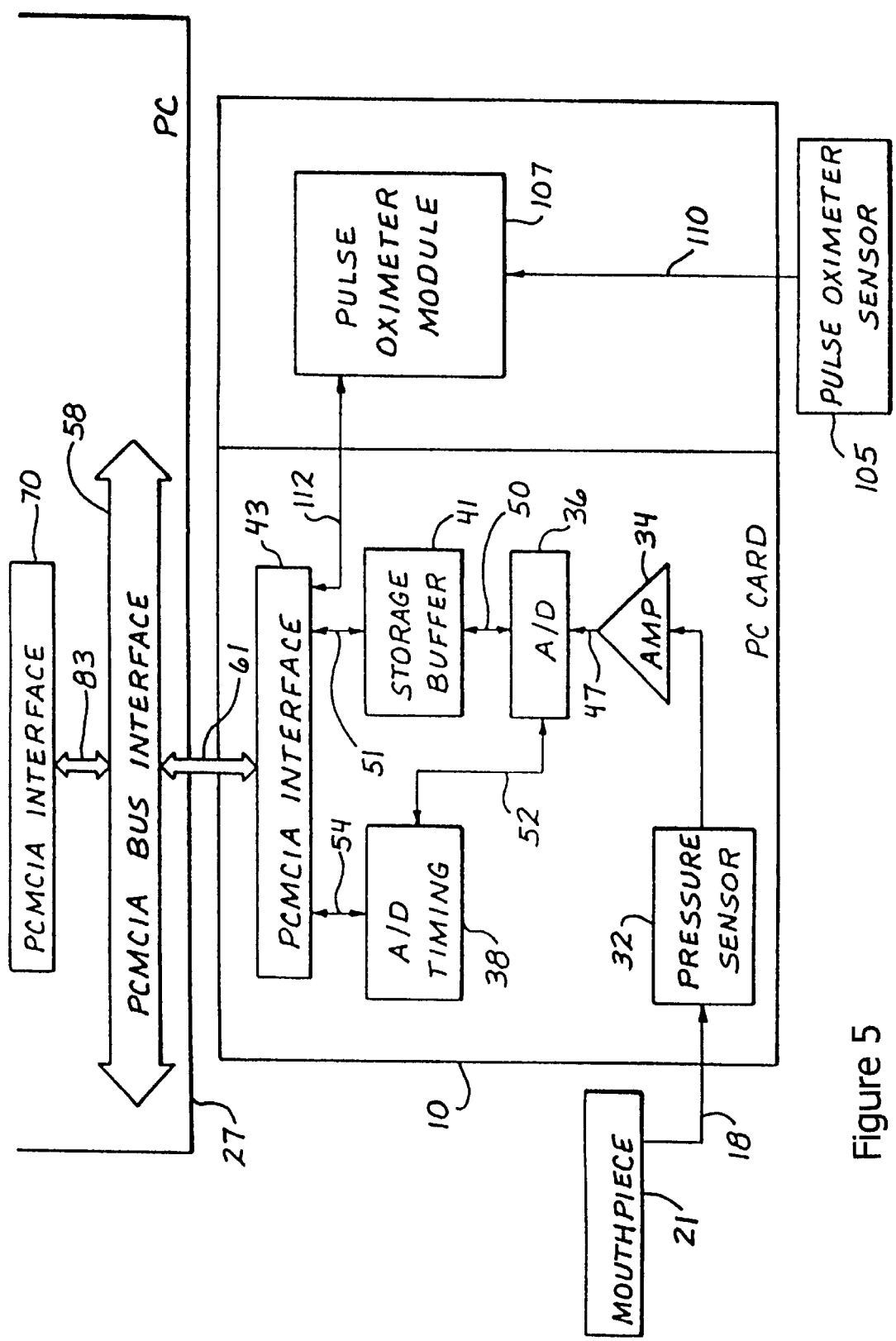
FIG. 5 illustrates a schematic block diagram of the circuitry of the real-time biological data processing PC card according to the present invention.

FIG. 5 illustrates a schematic block diagram of an embodiment of FIG. 4. Basically, data from a pulse oximeter sensor 105, such as the pulse oximeter clip 98 (FIG. 4), is fed to a pulse oximeter module 107 via a conductor path 110. As presently embodied, an optical coupler is positioned between the pulse oximeter finger clip 98 and a power source (not shown) connection of the real-time biological data processing PC card 10, to thereby prevent a patient from being shocked therefrom. Data from the pulse oximeter module 107 is then fed to the PCMCIA interface 43 via a conductor path 112. The pulse oximeter module 107 preferably comprises elements similar to the amplifier 34, the analog-to-digital converter 36, the analog-to-digital timing circuit 38, and the storage buffer 41. The elements of the pulse oximeter module 107 may be combined with or into the elements 34, 36, 38, 41 or, as presently embodied, maintained separately therefrom in the pulse oximeter module 107.

The host personal computer 27 may receive on a real-time basis, process, and monitor spirometry data and pulse oximetry data, either separately or simultaneously. The designation data, in the illustrated embodiment, indicates to the host personal computer 27 that the real-time biological data processing PC card 10 comprises both spirometry data and pulse oximetry data sensors. The pressure sensor 32 may alternatively be located on the disposable spirometry mouthpiece 21, as can the amplifier 34, the analog-to-digital converter 36, and the analog-to-digital timing circuitry 38, or any combination thereof. Any or all of these elements, in addition to the storage buffer 41, may be positioned on either the disposable spirometry mouthpiece 21, the pulse oximeter sensor 105, or the real-time biological data processing PC card 10, or any combination thereof, or eliminated altogether. Since the present invention is not intended to be limited to PCMCIA interfaces 43, any circuitry capable of forwarding an analog signal to a host personal computer 27 could reduce the need for components within the real-time biological data processing PC card 10. The pulse oximeter sensor 105 and the pulse oximeter module 107 may be manufactured by Nonin® Medical, Inc., located in Plymouth, Minnesota. According to one embodiment, the pulse oximeter sensor 105 may be similar that in an 8600 portable pulse oximeter, manufactured by Nonin® Medical, Inc.

FIG. 6a illustrates the main circuit board 118 of the presently preferred embodiment, generally corresponding to the elements 32–54 of FIG. 5. The main circuit board 118 is illustrated comprising a number of IC chips 121, a pressure input port 16, and a pressure sensor 32. A pulse oximetry module connector 125 accommodates a pulse oximetry module connector 127, which is illustrated in FIG. 6b. The pulse oximetry module connector 127 of FIG. 6b is electrically connected to a supplemental circuit board 130. The supplemental circuit board 130 generally corresponds to the pulse oximeter module 107 of FIG. 5.

FIG. 7 illustrates a perspective view of a pulse oximeter finger clip 98 connected to a hand 87 of a user. The pulse oximeter finger clip 98 is connected to the supplemental circuit board 130 via a pulse oximeter cable 101.

Figure 8:
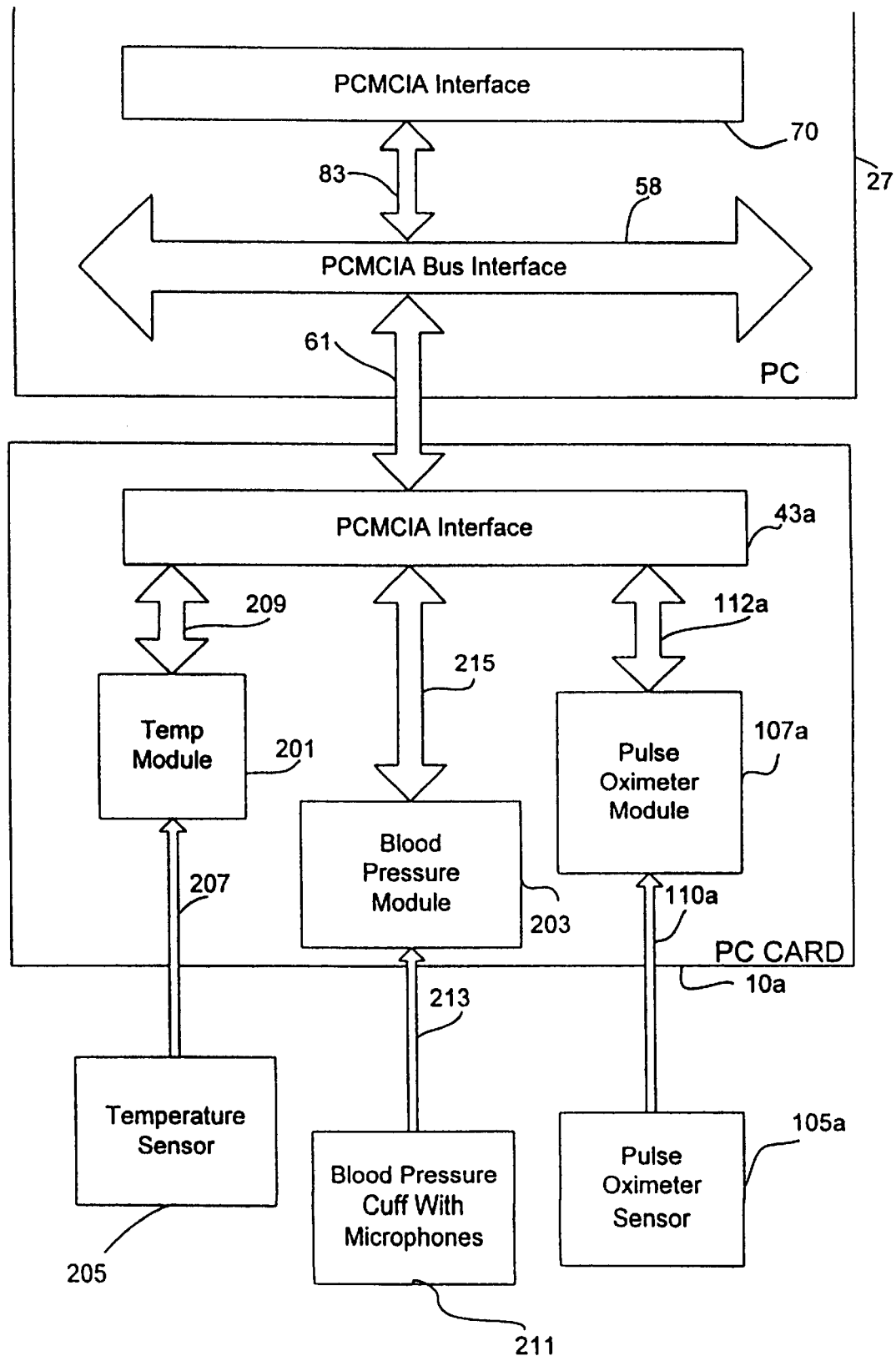
FIG. 8 illustrates a schematic block diagram of a real-time biological data processing PC card for collecting and forwarding on a real-time basis vitals data.

FIG. 8 illustrates a schematic block diagram of a real-time biological data processing PC card 10a for collecting and forwarding on a real-time basis vitals data. In the embodiment of FIG. 8, like elements are designated with like reference numerals followed by the letter "a." Data from a pulse oximeter sensor 105a is fed to a pulse oximeter module 107a via a conductor path 110a. As presently embodied, an optical coupler is positioned between a pulse oximeter finger clip (not shown) and a power source (not shown) connection of the real-time biological data processing PC card 10a, to thereby prevent a patient from being shocked therefrom. Data from the pulse oximeter module 107a is then fed to the PCMCIA interface 43a via a conductor path 112a. The pulse oximeter module 107a may comprise conventional circuitry for processing data from the pulse oximeter sensor 105a, such as elements including an amplifier, an analog-to-digital converter, an analog-to-digital timing circuit, and a storage buffer. The elements of the pulse oximeter module 107a may be combined with or into the elements of the temperature module 201 and the blood pressure module 203 or, as presently embodied, maintained separately therefrom in the pulse oximeter module 107a.

Data from a temperature sensor 205, indicating a body temperature of a patient, is fed to the temperature module 201 via a conductor path 207. Data from the temperature module 201 is then fed to the PCMCIA interface 43a via a conductor path 209. The temperature module 201 may comprise conventional circuitry for processing data from the temperature sensor 205, such as elements including an amplifier, an analog-to-digital converter, an analog-to-digital timing circuit, and a storage buffer. The elements of the temperature module 201 may be combined with or into the elements of the pulse oximeter module 107a and/or the elements of the blood pressure module 203 or, as presently embodied, maintained separately therefrom in the temperature module 201.

Data from a blood pressure sensor 211, indicating a blood pressure of a patient, is fed to the blood pressure module 203 via a conductor path 213. Data from the blood pressure module 203 is then fed to the PCMCIA interface 43a via a conductor path 215. The blood pressure sensor 211 preferably comprises a cuff with microphones as is known in the art. The blood pressure module 203 may comprise conventional circuitry for processing data from the blood pressure sensor 211, such as elements including an amplifier, an analog-to-digital converter, an analog-to-digital timing circuit, and a storage buffer. The elements of the blood pressure module 203 may be combined with or into the elements of the pulse oximeter module 107a and/or the elements of the temperature module 201 or, as presently embodied, maintained separately therefrom in the blood pressure module 203.

As presently embodied, a host personal computer 27 receives on a real-time basis, processes, and monitors pulse oximetry data, body temperature data, and blood pressure data either separately, sequentially, or simultaneously. The designation data, in the presently preferred embodiment, indicates to the host personal computer 27 that the real-time biological data processing PC card 10a comprises pulse oximetry data, temperature data and blood pressure data sensors. One or more of the components comprising the pulse oximeter module 107a, the temperature module 201 and/or the blood pressure module 203 may alternatively be located on the respective sensors 105a, 205, 211.

Figure 9:
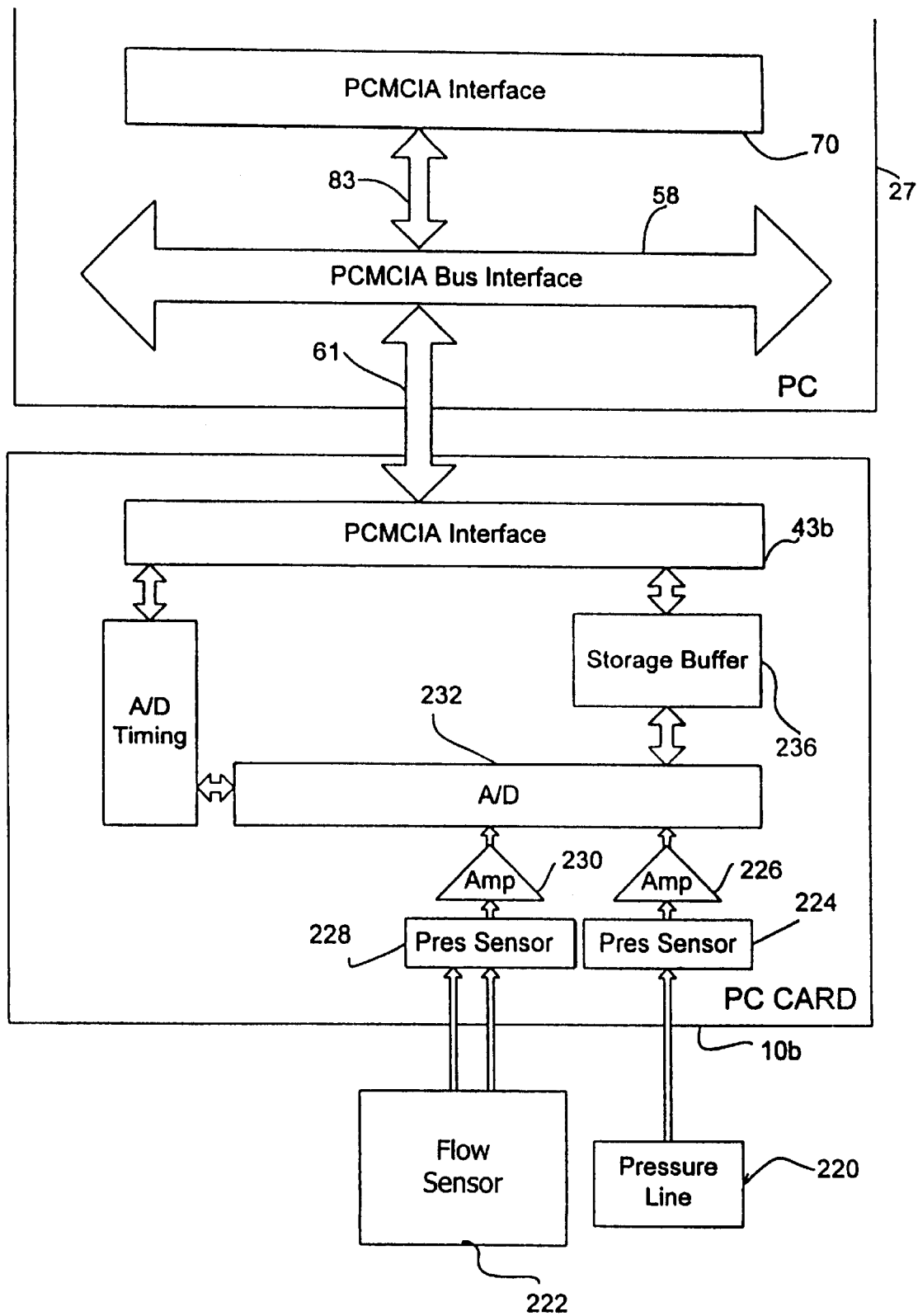
FIG. 9 illustrates a schematic block diagram of a real-time biological data processing PC card for collecting and forwarding on a real-time basis ventilator-operation data.

Turning to FIG. 9, a schematic block diagram of a real-time biological data processing PC card for collecting and forwarding on a real-time basis ventilator operation data is shown. In the embodiment of FIG. 9, like elements are designated with like reference numerals followed by the letter "b." A pressure line 220 and flow line 222 are connected to monitor pressure and flow rate of a ventilator connected to a patient. The pressure line inputs pressure data from a hose of the ventilator to a pressure sensor 224 and, subsequently, to an amplifier 226. The flow line 222 are input into the pressure sensors 228 and the amplifier 230. An analog-to-digital converter 232 receives the signals from the amplifiers 226 and 230, and converts the signals to digital signals. The digital signals are forwarded to the PCMCIA interface 43b via a storage buffer 236.

The host personal computer 27 receives on a real-time basis, processes and monitors the pressure and flow rate data from the sensors 220 and 222 either separately, sequentially or simultaneously. The designation data indicates to the host personal computer 27 that the real-time biological data processing PC card 10b comprises pressure and flow rate data from a ventilator hose connected to a patient. One or more of the components of the PC card may be placed on the pressure line 220 or the differential flow line 222.

Figure 10:
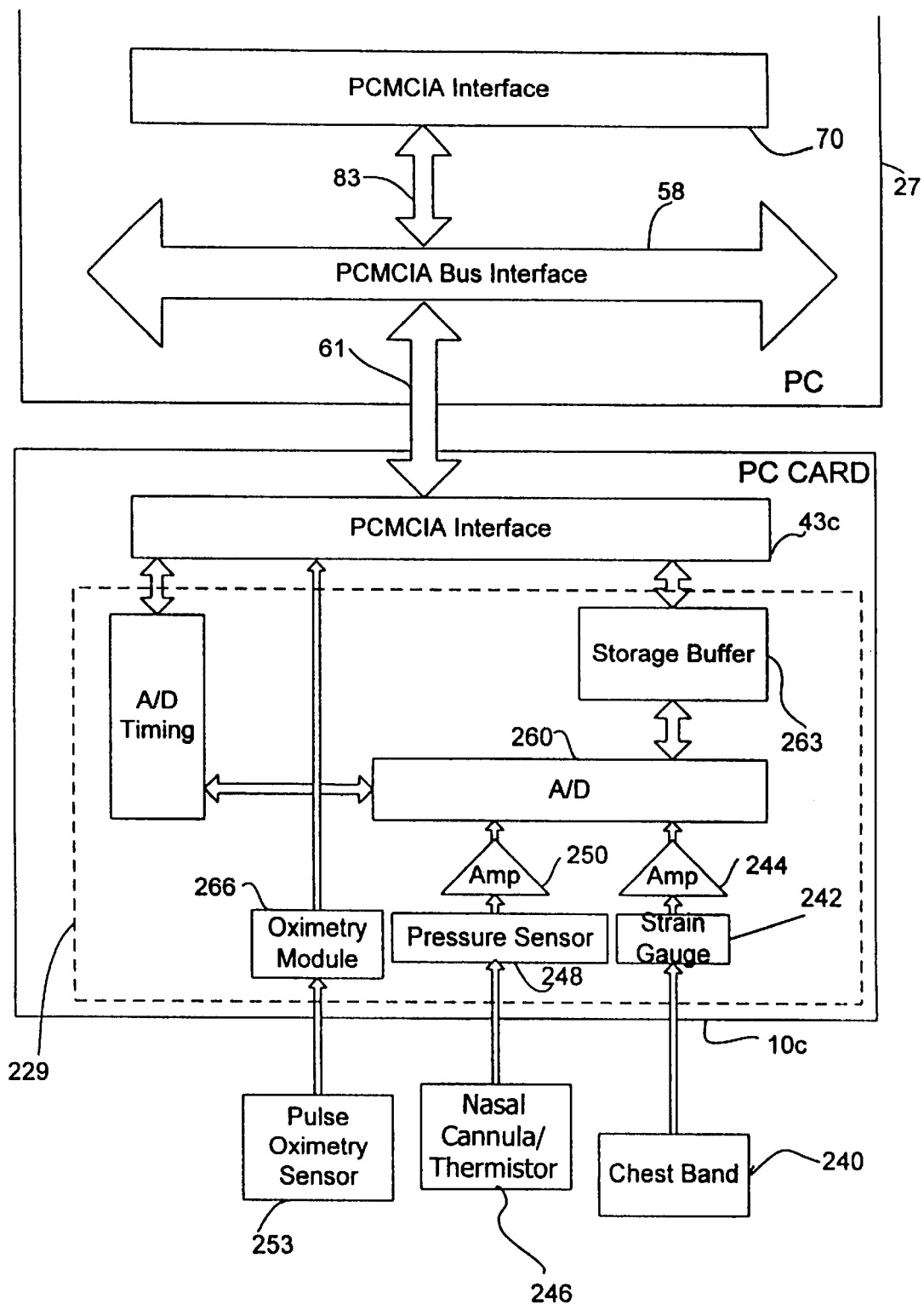
FIG. 10 illustrates a schematic block diagram of a real-time biological data processing PC card for collecting and forwarding on a real-time basis sleep-related data.

FIG. 10 illustrates a schematic block diagram of a real-time biological data processing PC card for collecting and forwarding on a real-time basis, sleep-related data. A chest band 240 is placed around a patient's chest to measure the patient's respiration rate, for example. Sensors on the chest band 240 measure movement of the patient's chest while the patient is sleeping for determining, for example, whether the patient is breathing through his or her nose and whether an obstruction is present. Data from sensors on the chest band 240 is input into a strain gauge 242 and subsequently amplified by an amplifier 244. A nasal canula/thermistor 246 measures breathing through a patient's nose, and the data therefrom is input into a pressure sensor 248 and subsequently amplified by the amplifier 250. A pulse oximetry sensor 253 measures the patient's pulse rate and/or blood-oxygen concentration. Data from the chest band 240 and the nasal canula/thermistor 246 is digitized by the analog-to-digital converter 260 and passed to the PCMCIA interface 43c via a storage buffer 263. Data from the pulse oximetry sensor 253 is similarly passed to the PCMCIA interface 43c after being processed by an oximetry module 266. The data from the chest band 240, the nasal canula/thermistor 246 and the pulse oximetry sensor 253 is transferred to the host personal computer 27 on a real-time basis, either separately, sequentially of simultaneously.

Figure 11:
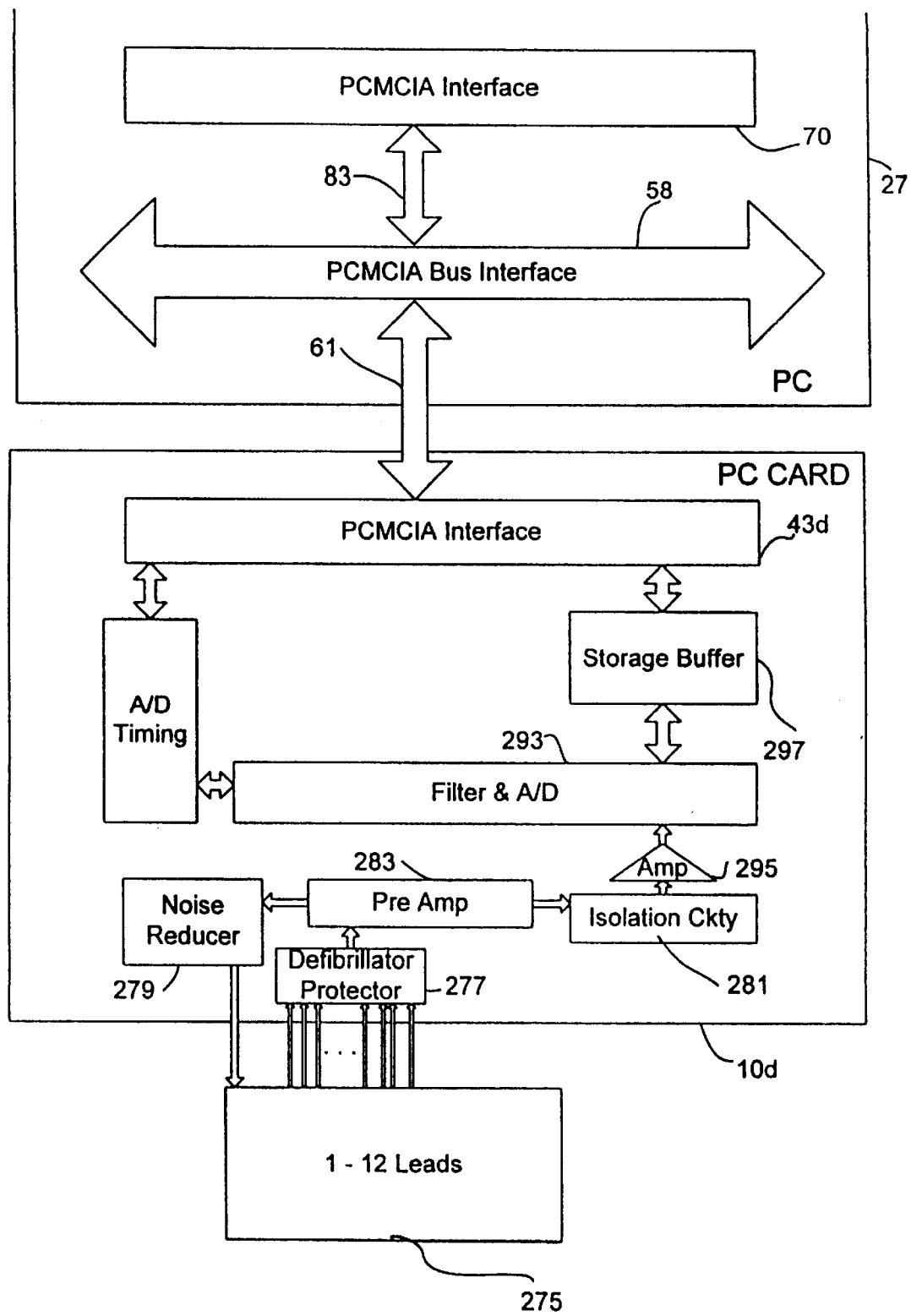
FIG. 11 illustrates a schematic block diagram of a real-time biological data processing PC card for collecting and forwarding on a real-time basis ECG data.

FIG. 11 illustrates a schematic block diagram of a real-time biological data processing PC card for collecting and forwarding on a real-time basis ECG data. One to twelve leads 275 are attached to a patient for inputting ECG data to a defibrillator protector 277. The defibrillator protector 277 accommodates operation of the PC card 10d when the patient is defibrillated, as is known in the art. Conventional noise reduction 279 and isolation 281 components receive data from the preamp 283. Data from the isolation circuitry 281 is input to a filter and analog-to-digital conversion module 293 via an amplifier 295. The ECG data is input into a PCMCIA interface 43d via a storage buffer 297. The noise reducer 279 may comprise, for example, a driven right leg and driven shield configuration, wherein an ECG signal from the leads 275 is inverted and injected back into the patient's right leg to cancel noise. The driven shield comprises a similar mechanism for reducing noise as is known in the art.

The PC card 10d may be configured to implement a signal averaging mode of ECG data collection, wherein a relatively high sampling rate of 2,000 to 3,000 samples per second is implemented, for example. The samples are subsequently averaged for providing additional resolution, compared to a slower sampling rate such as 250 samples per second. Moreover, instead of implementing one to twelve leads for feeding electrical signals from the patient to the PC card 10d, a wireless embodiment may be implemented. In this embodiment, electrical signals from the patient are transmitted to a receiver on a PC card, for example. Processed data from the twelve leads 275 is transferred from the PC card 10d to the host personal computer 27 on a real-time basis in accordance with the present invention.

Figure 12:
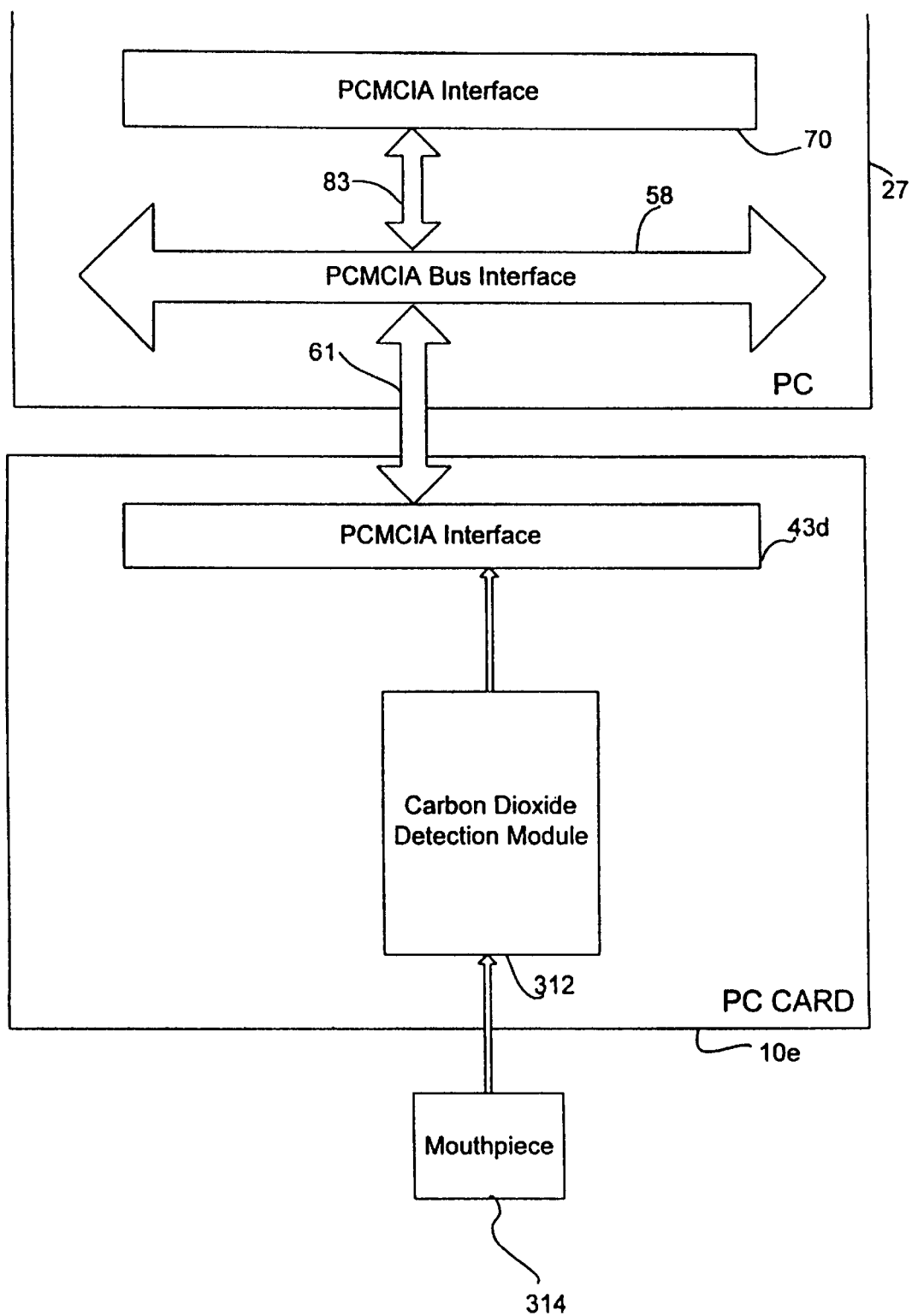
FIG. 12 illustrates a schematic block diagram of a real-time biological data processing PC card for collecting and forwarding on a real-time basis carbon-dioxide detection data.
Figure 13:
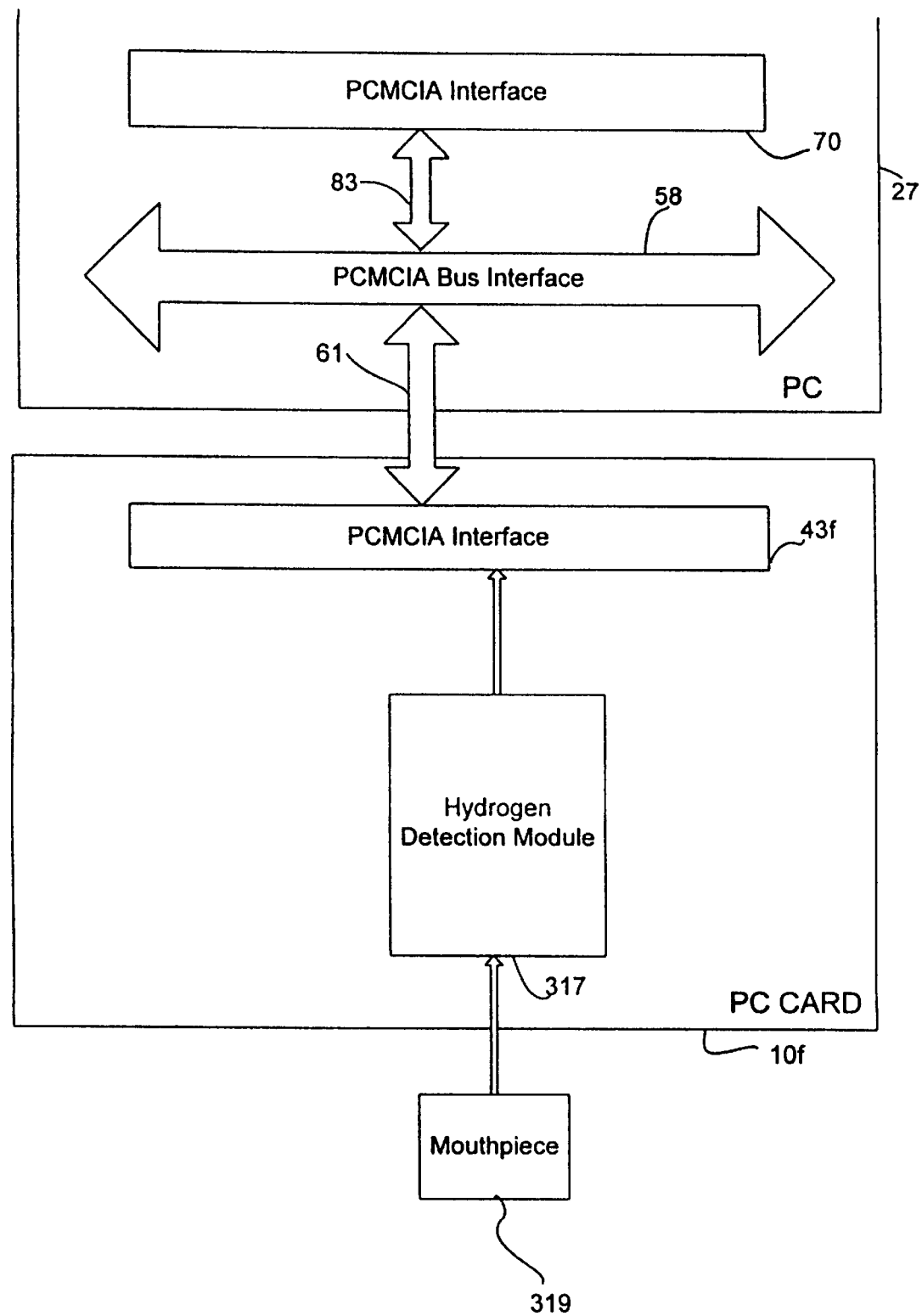
FIG. 13 illustrates a schematic block diagram of a real-time biological data processing PC card for collecting and forwarding on a real-time basis hydrogen detection data.
Figure 14:
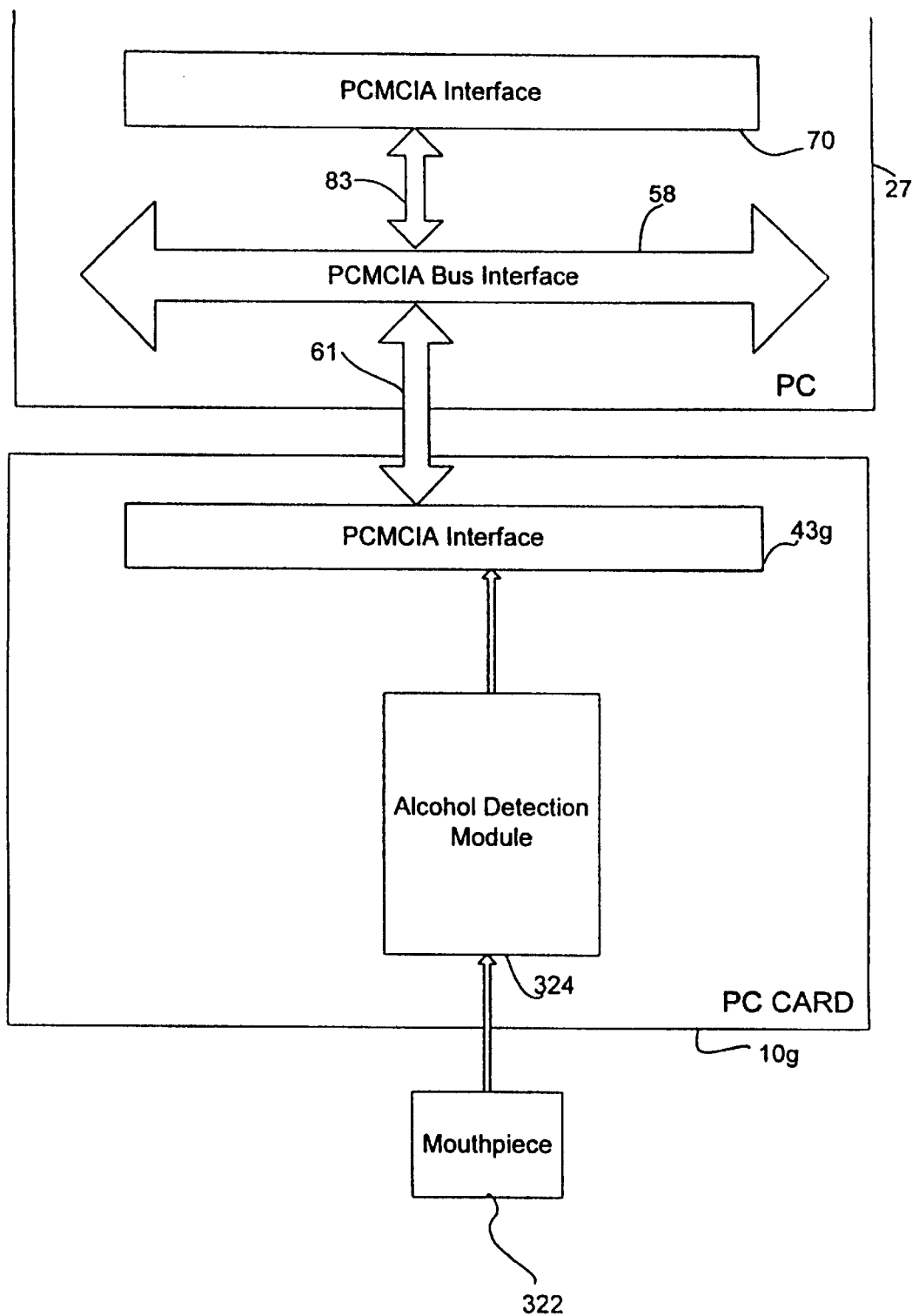
FIG. 14 illustrates a schematic block diagram of a real-time biological data processing PC card for collecting and forwarding on a real-time basis alcohol detection data.

Turning to FIG. 12, a PC card 10e for collecting and forwarding on a real-time basis carbon dioxide detection data to a host personal computer 27 on a real-time basis is disclosed. Carbon dioxide in the breath of a patient is detected by a carbon dioxide detection module 312, after being input through a mouthpiece 314. FIG. 13 illustrates a hydrogen detection module 317 within a PC card 10f. A patient breathes into a mouthpiece 319. A reading on a detected amount of hydrogen is forwarded to the PC card 27 via a PCMCIA interface 43f of the PC card 10f on a real-time basis. As shown in FIG. 14, a real-time biological data processing PC card 10g collects breath from a user via a mouthpiece 322. An amount of alcohol in the user's breath is detected by an alcohol detection module 324, which sends digital data to the PCMCIA interface 43g for subsequent routing on a real-time basis to the personal computer 27.

Figure 15:
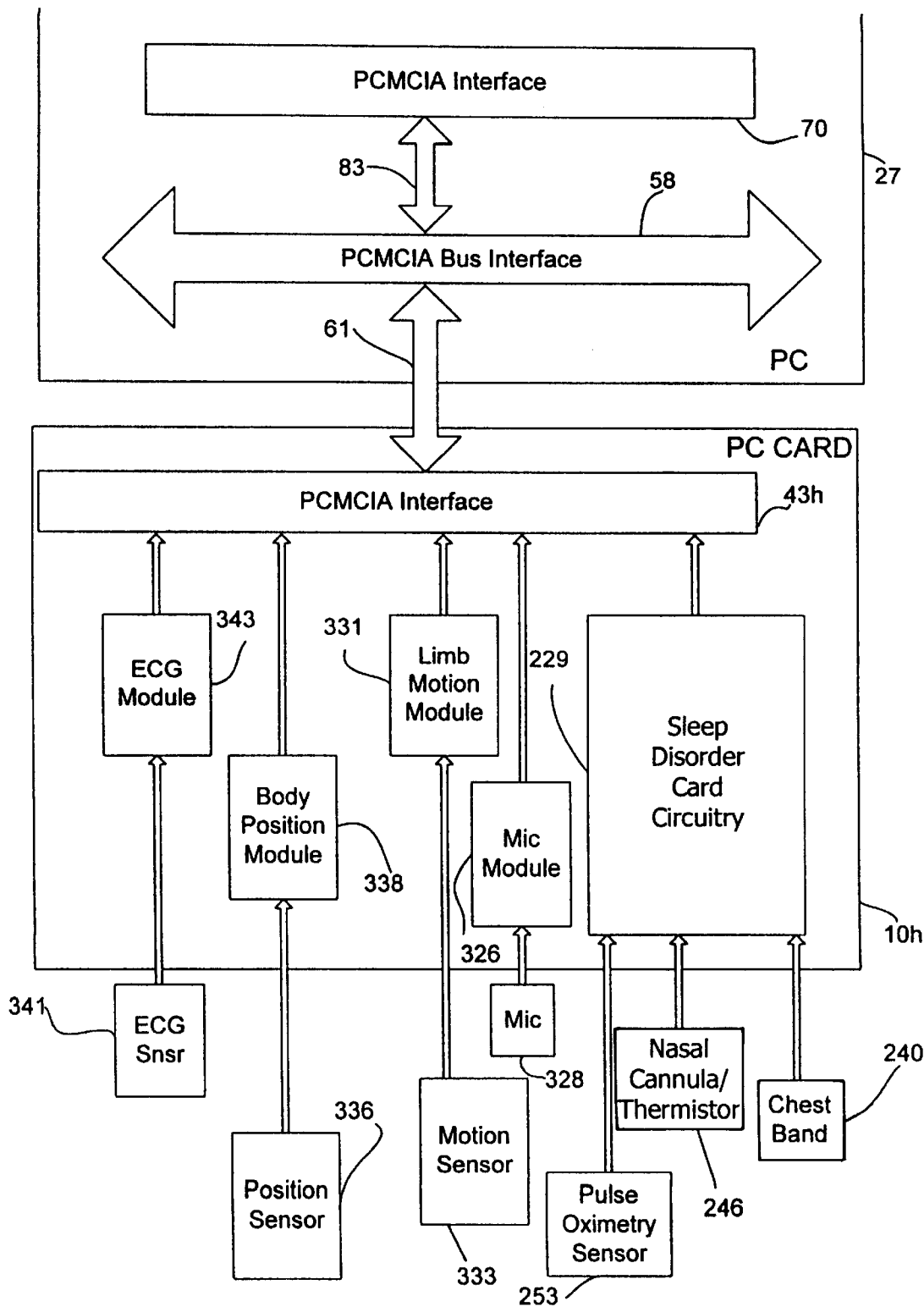
FIG. 15 illustrates a schematic block diagram of a real-time biological data processing PC card for collecting and forwarding on a real-time basis sleep-related data including body motion and position and ECG.

A real-time biological data processing PC card for collecting and forwarding on a real-time basis sleep-related data including body motion and position, and ECG, is shown in FIG. 15. The apnea card circuitry generally corresponds to that disclosed in FIG. 10, and the PC card 10h further comprises a microphone module 326 for receiving sound signals from a microphone 328 and forwarding digitized signals on a real-time basis to the PCMCIA interface 43h. A limb motion module 331 inputs data from motion sensors 333. Data from the motion sensor or sensors 333 is processed by the limb motion module 331 and forwarded on a real-time basis to the PCMCIA interface 43h. Position data from a position sensor 336 is forwarded to the body position module 338, processed, and subsequently forwarded on a real-time basis to the PCMCIA interface 43h. The microphone 328 can be attached to a neck of a patient, for example, for providing information as to whether the patient is snoring. The motion sensor 333 may comprise an accelerometer, for example, and may be attached to a limb of a patient to determine limb and/or body motion. The position sensor 336 may comprise a mercury switch, for example, and may be attached to a portion of a patient to determine whether the patient is lying on his or her stomach or back, for example. An ECG sensor 341 may comprise one or two channels, for example, for inputting electrical information to the ECG module 343. Processed information from the ECG module 343 is subsequently forwarded on a real-time basis to the PCMCIA interface 43h.

Figure 16:
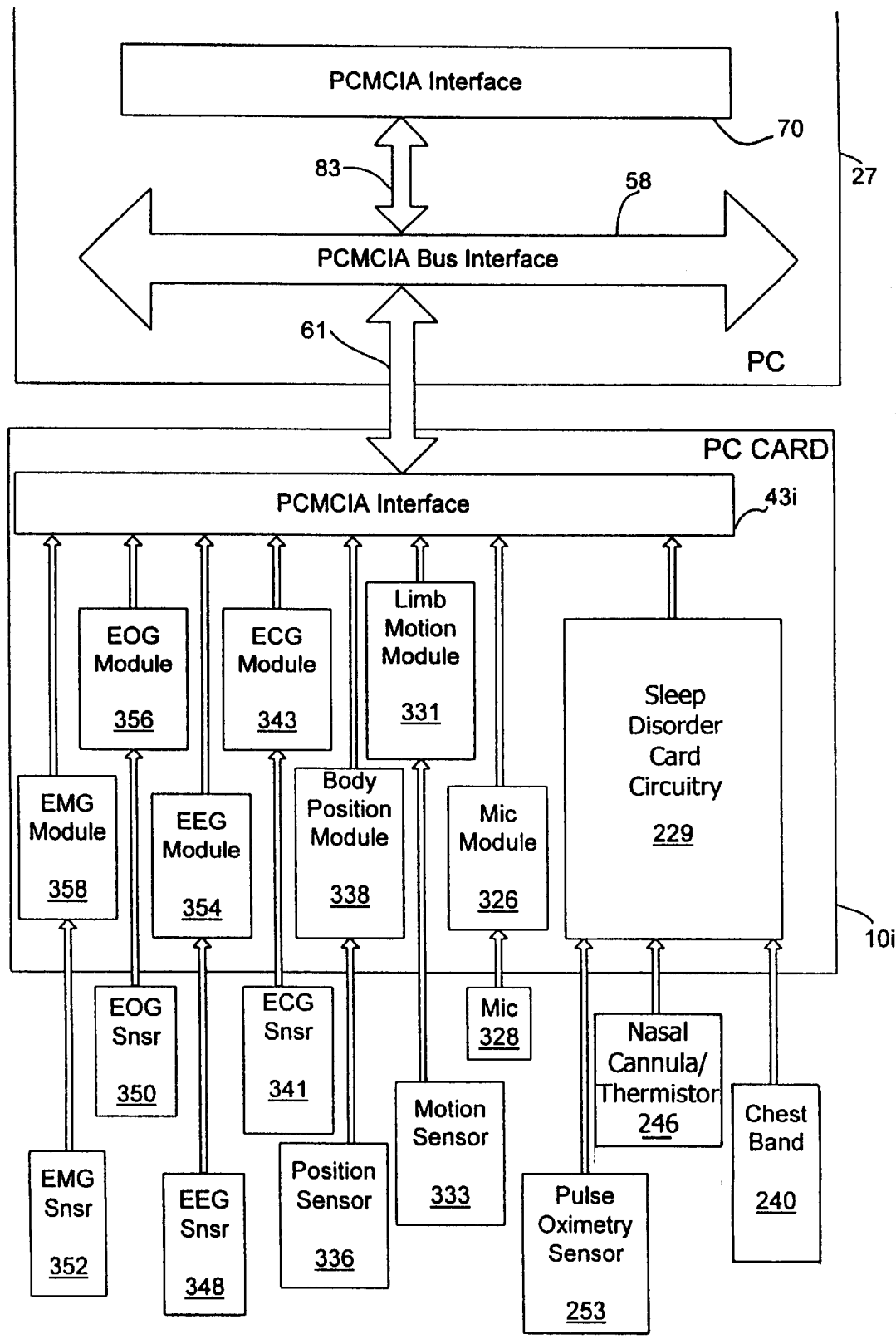
FIG. 16 illustrates a schematic block diagram of a real-time biological data processing PC card for collecting and forwarding on a real-time basis sleep-related data including body motion and position, ECG, EOG and EMG.

The PC card 10i of FIG. 16 is similar to that depicted in FIG. 15, with additional EEG, EOG, and EMG components. An EEG sensor 348, an EOG sensor 350 and an EMG sensor 352 forward signals detected on a patient to an EEG module 354, an EOG module 356, and an EMG module 358, respectively, on a real-time basis. The EEG module 354, the EOG module 356 and the EMG module 358 forward processed data to the PCMCIA interface 43i on a real-time basis and, subsequently, as with the other embodiments of the present invention, the PCMCIA interface 43i preferably forwards the real-time data to the host personal computer 27 on a real-time basis.

Figure 17:
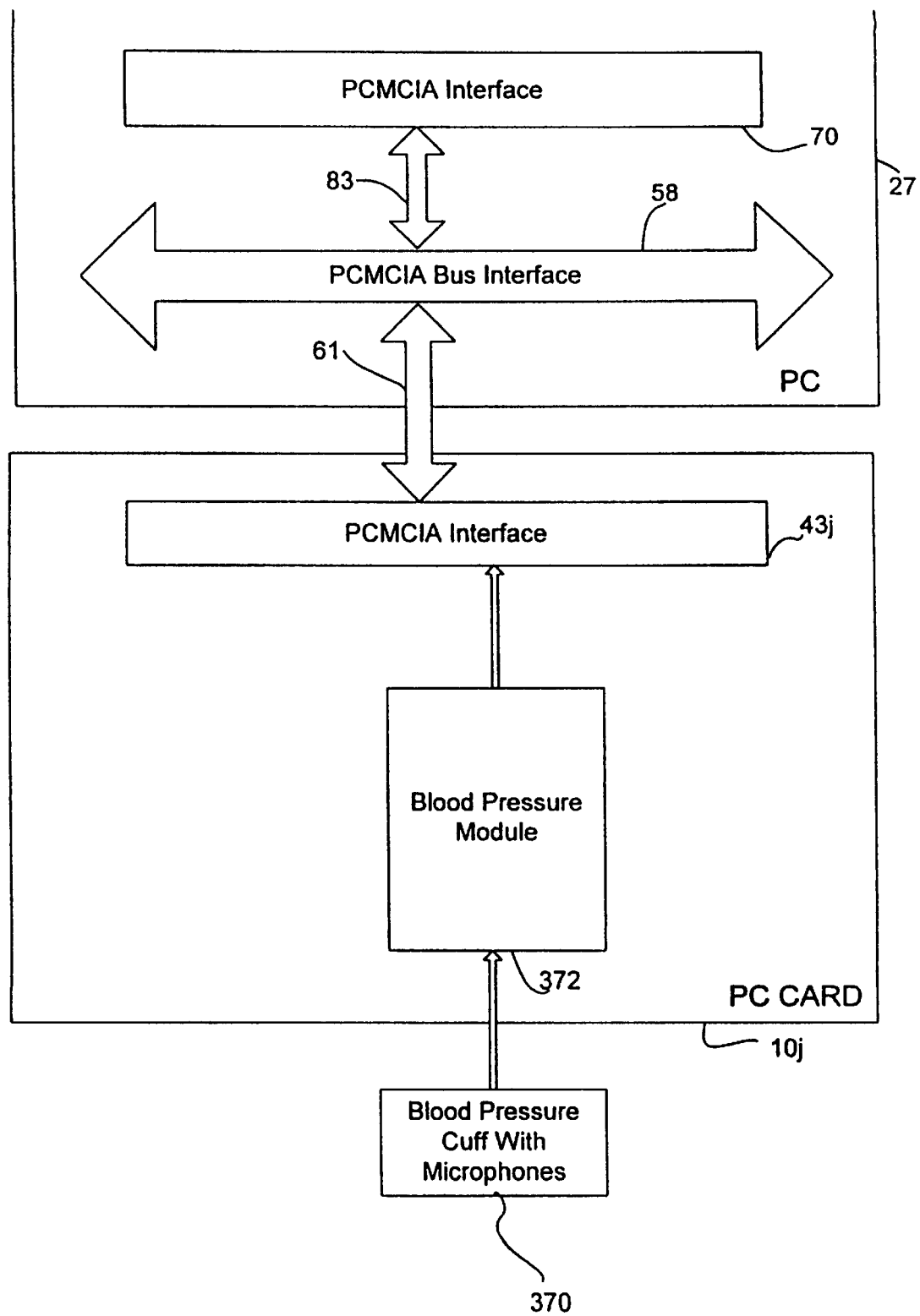
FIG. 17 illustrates a schematic block diagram of a real-time biological data processing PC card for collecting and forwarding on a real-time basis blood pressure related data.

Turning to FIG. 17, a real-time biological data processing PC card 10j inputs blood pressure data from a blood pressure sensor 370 on a real-time basis. The blood pressure sensor preferably comprises a blood pressure cuff with microphones. A blood pressure module 372 receives the data from the sensor 370 and forwards processed digitized data on a real-time basis to the PCMCIA interface 43j.

Figure 18:
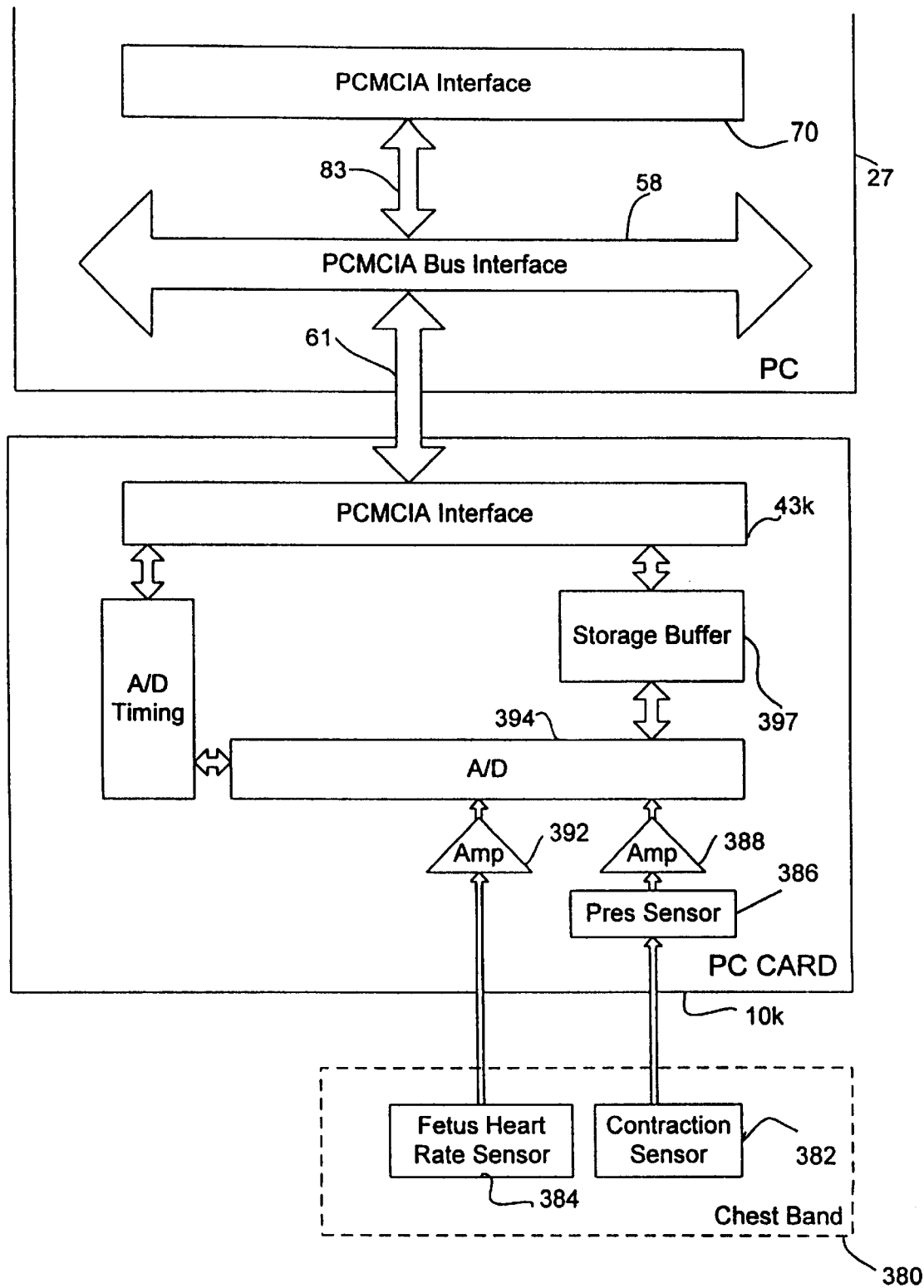
FIG. 18 illustrates a schematic block diagram of a real-time biological data processing PC card for collecting and forwarding on a real-time basis birth procedure related data.

FIG. 18 illustrates a real-time biological data processing PC card for collecting and forwarding on a real-time basis birth procedure related data. A chest band 380 comprises a contraction sensor 382 and a fetus heart rate sensor 384. The contraction sensor 382 may comprises a pressure sensor, for example, which is adapted to be disposed on a woman's stomach via the chest band 380, and the fetus heart rate sensor 384 may comprise a microphone. An additional sensor (not shown) may also be incorporated for monitoring on a real-time basis the mother's heart rate. The additional sensor may comprise, for example, a pulse oximeter. Data from the contraction sensor 382 and the fetus heart rate sensor 384 is input into the pressure sensors and amplifiers 386, 388, 390, 392. An analog-to-digital converter 394 processes the information and outputs the information to the PCMCIA interface 43k via a storage buffer 397.

Figure 19:
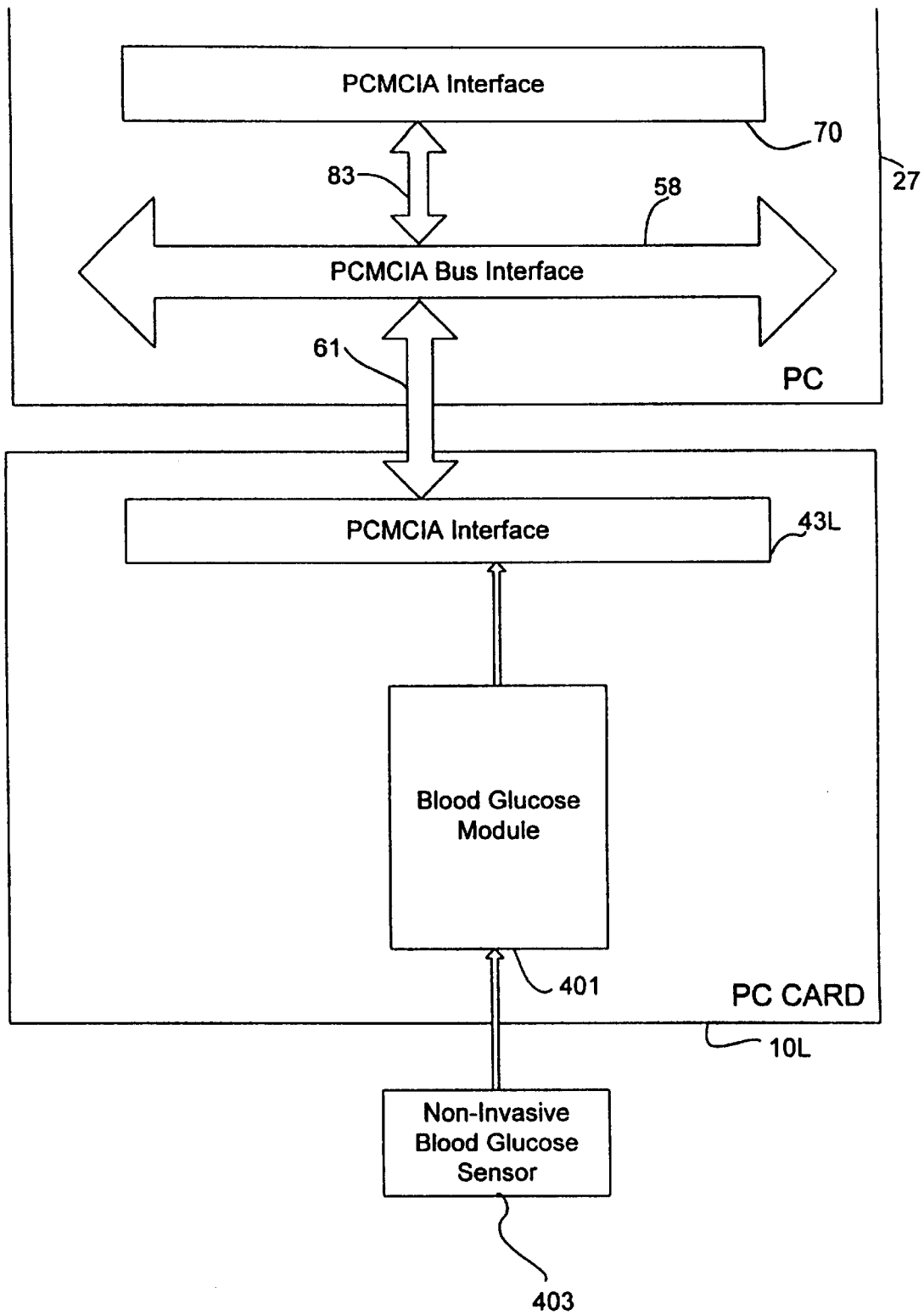
FIG. 19 illustrates a schematic block diagram of a real-time biological data processing PC card for collecting and forwarding on a real-time basis blood glucose detection data.
Figure 20:
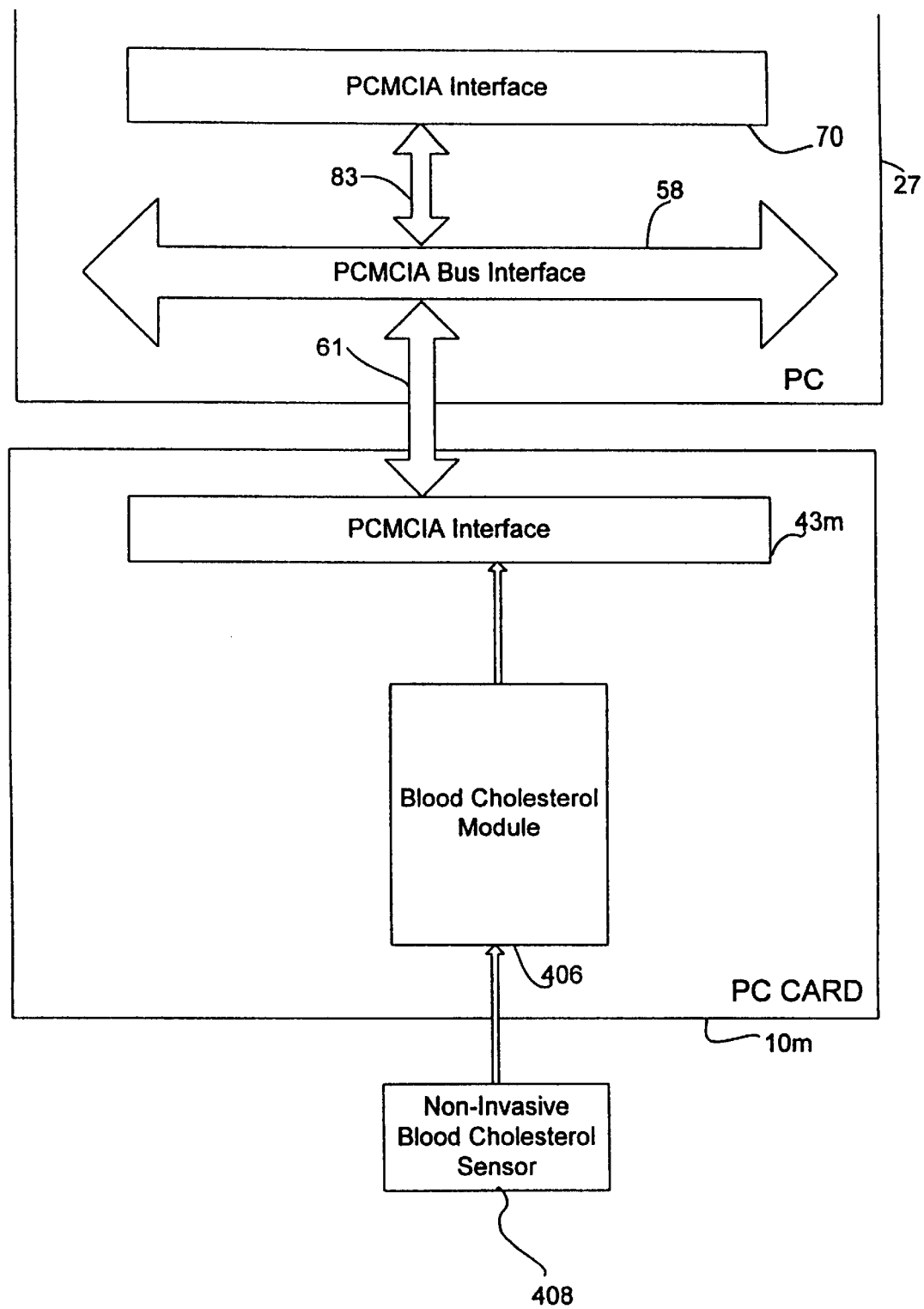
FIG. 20 illustrates a schematic block diagram of a real-time biological data processing PC card for collecting and forwarding on a real-time basis blood cholesterol detection data.
Figure 21:
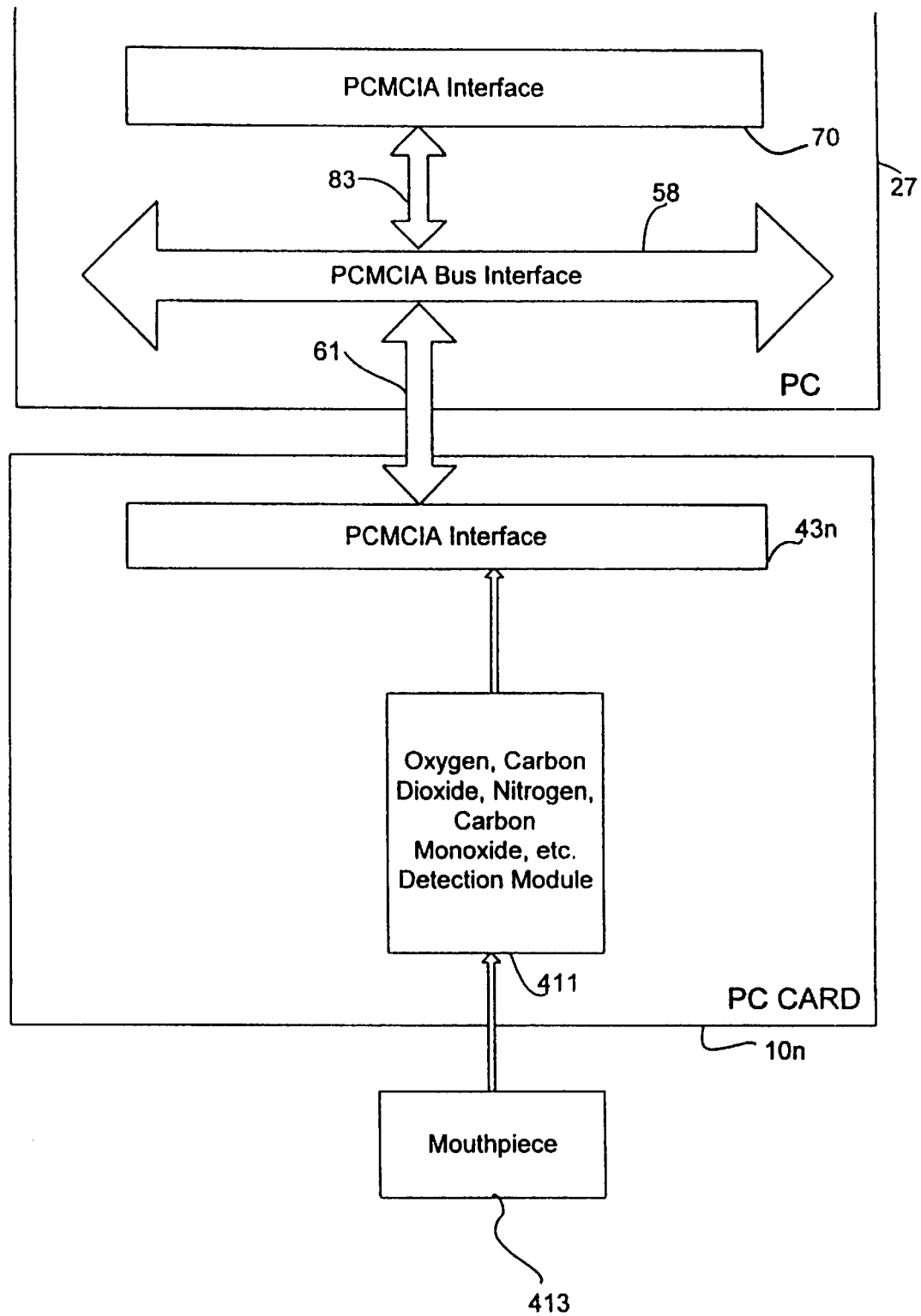
FIG. 21 illustrates a schematic block diagram of a real-time biological data processing PC card for collecting and forwarding on a real-time basis blood arterial-blood-gas detection data.
Figure 22:
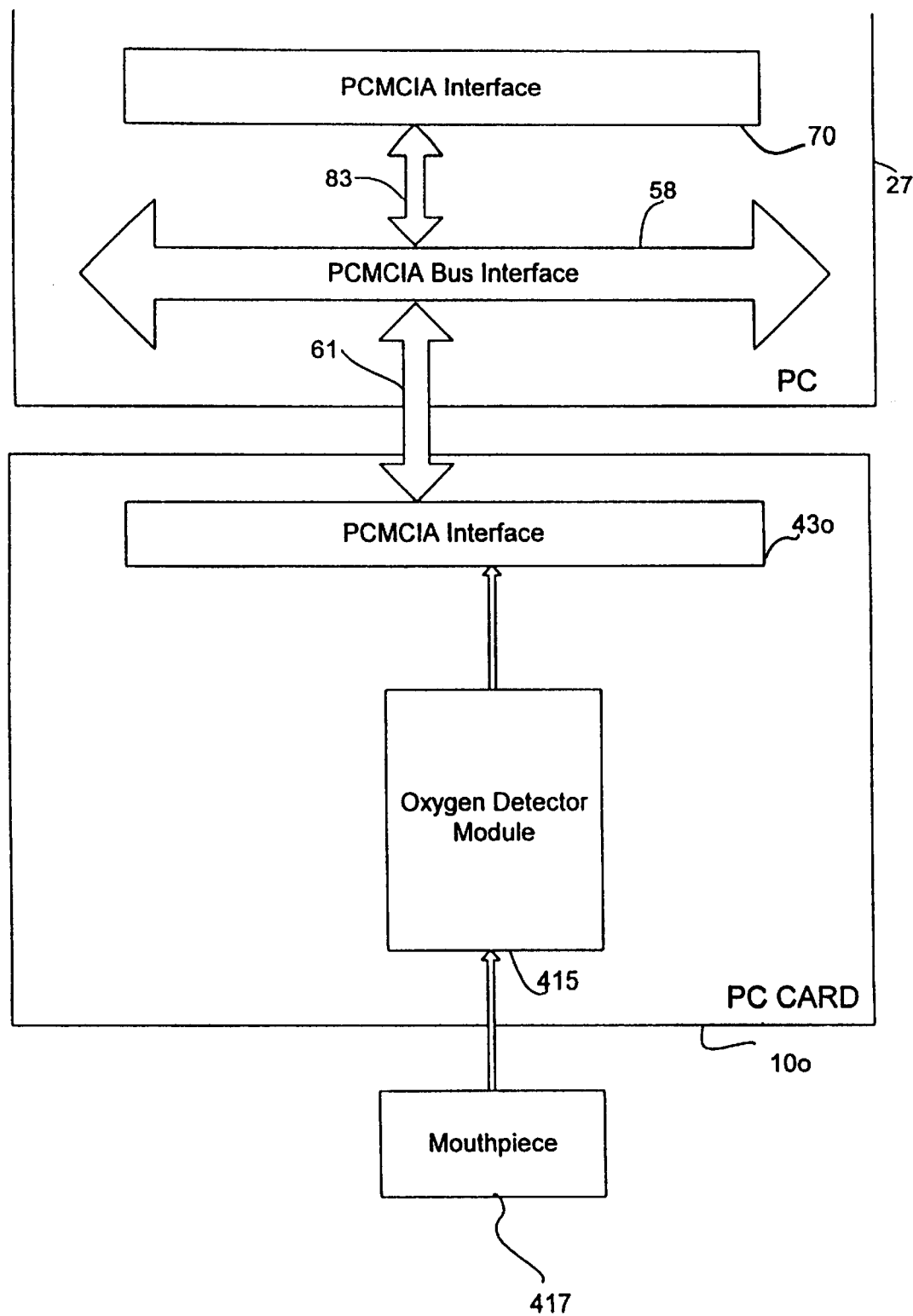
FIG. 22 illustrates a schematic block diagram of a real-time biological data processing PC card for collecting and forwarding on a real-time basis oxygen detection data.

FIGS. 19, 20, and 21 illustrate non-invasive blood composition detection PC cards 10L, 10m and 10n, respectively, for collecting on a real-time basis biological data and forwarding the data on a real-time basis to a host personal computer 27. The blood glucose module 401 of the PC card 10L inputs blood glucose data from a non-invasive blood glucose sensor 403 on a real-time basis. The non-invasive blood glucose sensor 403 may comprise any conventional means for measuring a blood glucose concentration of a patient, such as, for example, a patch adapted to be attached to a person's skin or an optical measuring apparatus. A blood cholesterol module 406 of the PC card 10m (FIG. 20) inputs blood cholesterol data from a non-invasive blood cholesterol sensor 408. The non-invasive blood cholesterol sensor 408 may comprise any non-invasive blood-cholesterol measuring apparatus. The detection module 411 (FIG. 21) of the PC card 10n is adapted to receive a breath of a patient via a mouthpiece 413, and detect on a real-time basis gases including, oxygen, carbon dioxide, nitrogen and/or carbon monoxide. Each of the modules 401, 406 and 411 forwards processed sensor data on a real-time basis to the PCMCIA interfaces 43L, 43m and 43n, respectively. FIG. 22 illustrates a PC card 10o comprising an oxygen detector 415 for inputting breath from a mouthpiece 417 and forwarding processed data on a real-time basis to a PCMCIA interface 43o.

Figure 23:
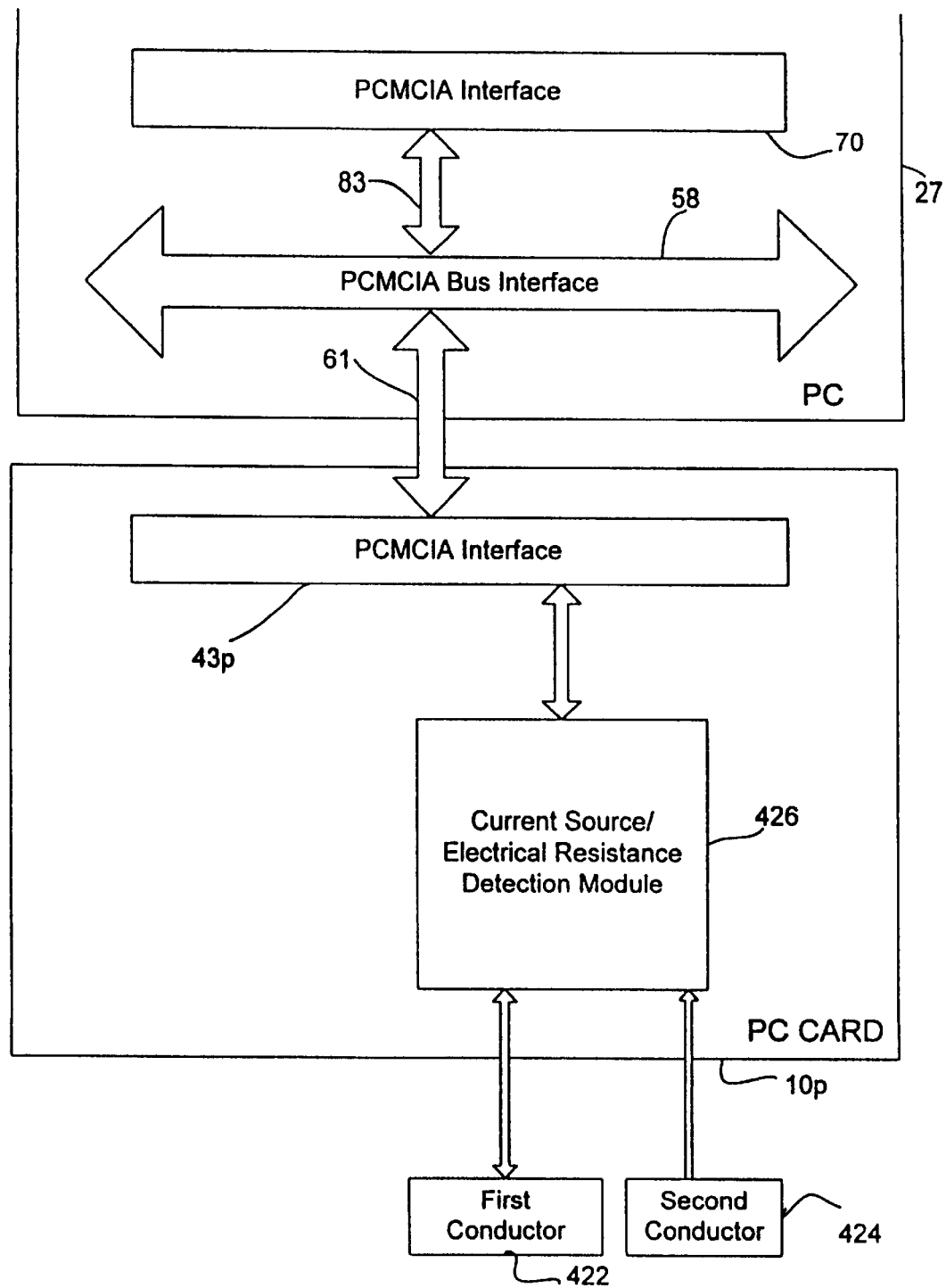
FIG. 23 illustrates a schematic block diagram of a real-time biological data processing PC card for collecting and forwarding on a real-time basis body composition data.

A real-time biological data processing PC card 10p for collecting and forwarding on a real-time basis body composition data is illustrated in FIG. 23. A first conductor 422 and a second conductor 424 provide electrical resistance data on a real-time basis to the current source/electrical resistance module 426, which subsequently forwards processed information to the PCMCIA interface 43*p*. The current source/electrical resistance detection module 426 in a preferred embodiment injects an electrical signal into a patient via the first conductor 422, and uses the second detector 424 to determine an electrical resistance of the patient. In modified embodiments, either the current source, the electrical resistance detector, or both, may be disposed within the host personal computer 27. Based upon the measured electrical resistance and the electrical signal injected into the patient, an estimate of a fat composition of the patient is generated and forwarded to the PCMCIA interface 43*p* on a real-time basis.

Figure 24:
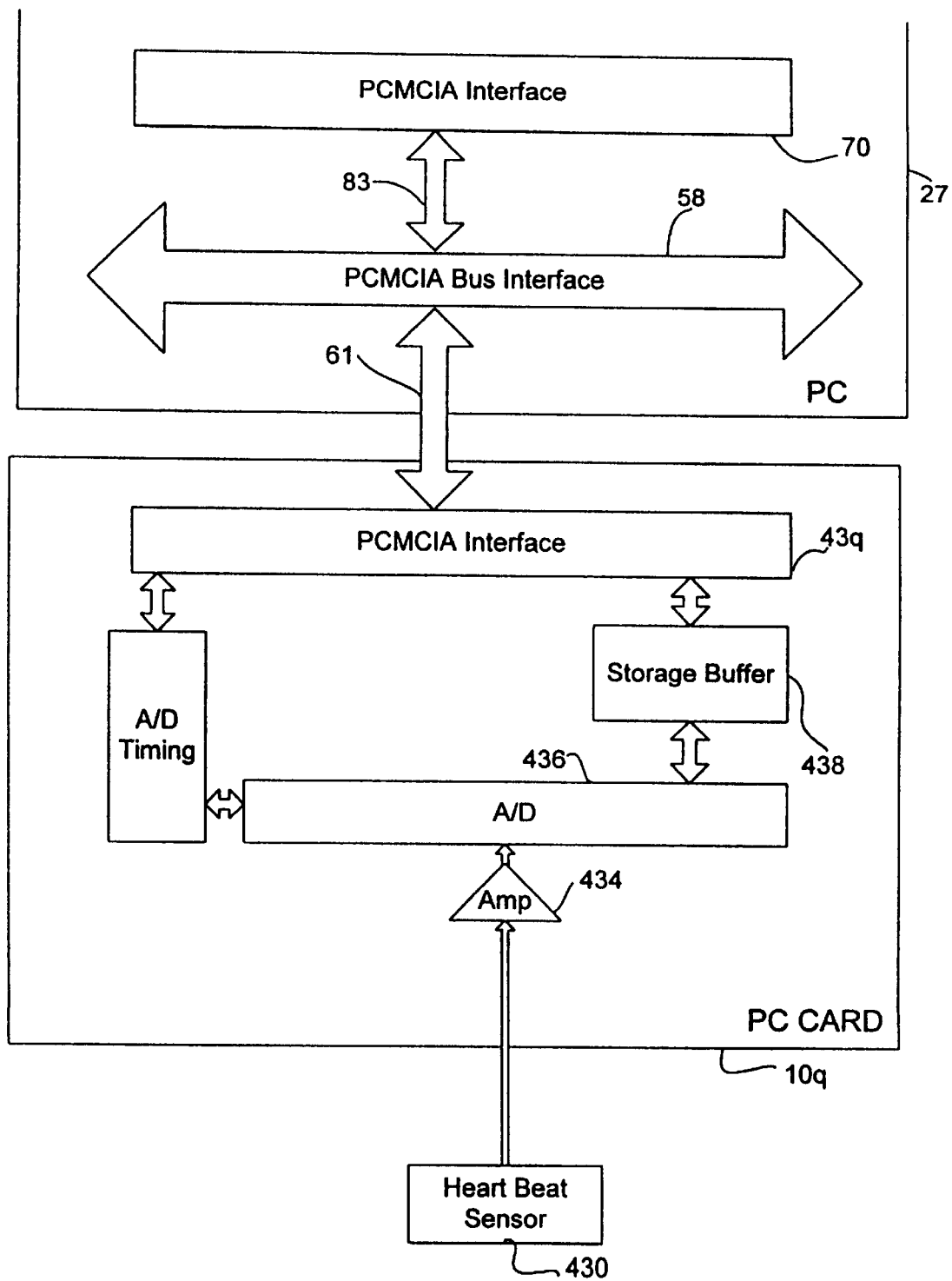
FIG. 24 illustrates a schematic block diagram of a real-time biological data processing PC card for collecting and forwarding on a real-time basis heart beat data.

The PC card 10*q* illustrated in FIG. 24 collects heartbeat information on a real-time basis from a heartbeat sensor 430. The heartbeat information is processed via an amplifier 434 and an analog-to-digital converter 436, and is passed on a real-time basis to the PCMCIA interface 43*q* via a storage buffer 438. The real-time heartbeat data can be monitored and manipulated on the personal computer 27.

Figure 25:
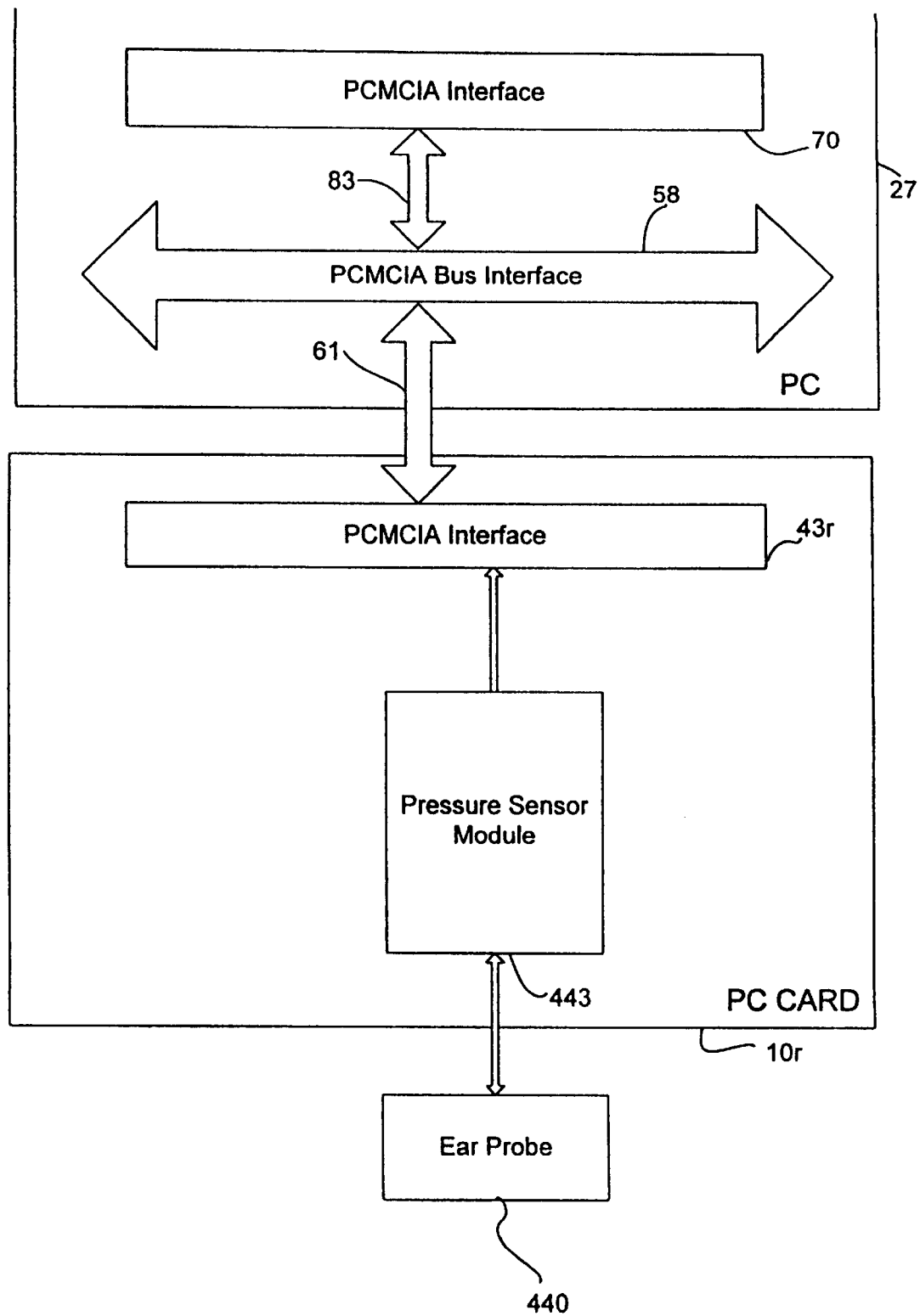
FIG. 25 illustrates a schematic block diagram of a real-time biological data processing PC card for collecting and forwarding on a real-time basis ear-drum pressure data.

The PC card 10*r* of FIG. 25 inputs data on a real-time basis from an ear probe 440 into a pressure sensor module 443, which processes the data and subsequently outputs the processed data to the PCMCIA interface 43*r* on a real-time basis. The ear probe 440 may comprise a hand-held wand for placement into the ear of a patient. The hand-held wand may comprise mechanical means for measuring the eardrum pressure or, alternatively, may comprise optical means for measuring an eardrum pressure of the patient as is well known in the art.

Figure 26:
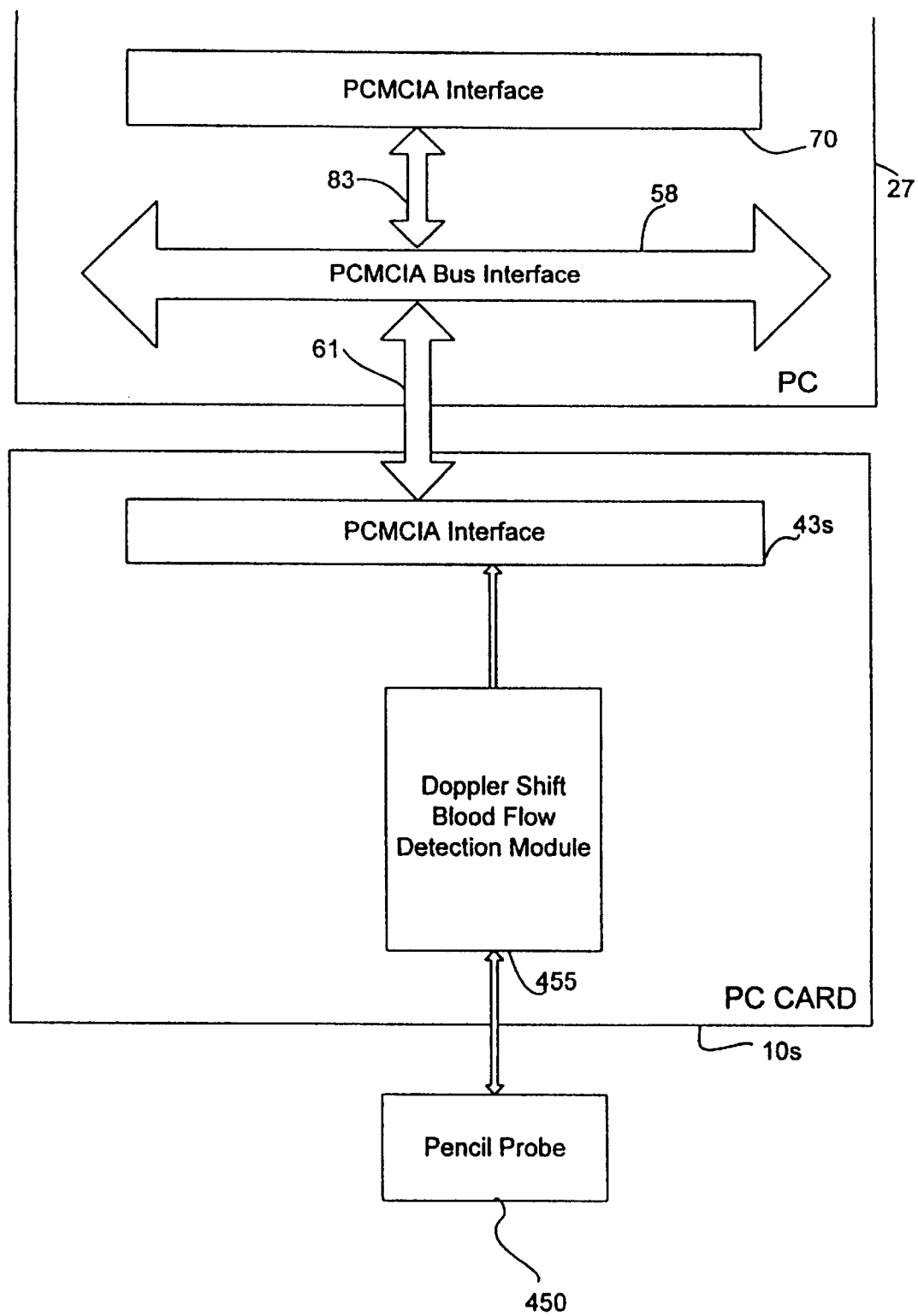
FIG. 26 illustrates a schematic block diagram of a real-time biological data processing PC card for collecting and forwarding on a real-time basis blood flow related data.
Figure 27:
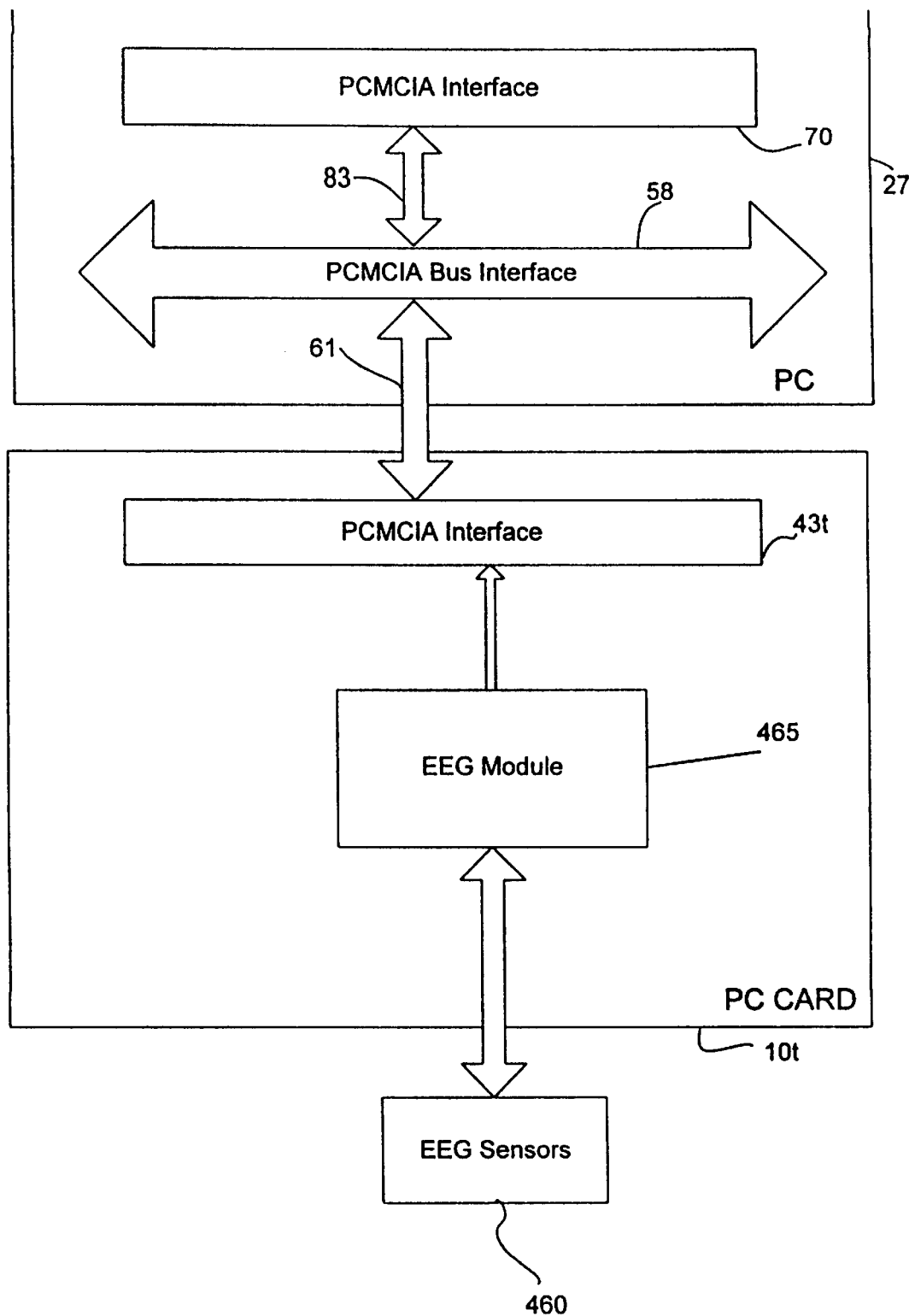
FIG. 27 illustrates a schematic block diagram of a real-time biological data processing PC card for collecting and forwarding on a real-time basis EEG related data.

Turning to FIG. 26, a PC card 10*s* inputs data from a pencil probe 450 into a Doppler shift blood flow detection module 455 on a real-time basis. The pencil probe 450 emits acoustical signals which are used for measuring blood flow as is known in the art. Information from the pencil probe 450 is first processed by the Doppler shift blood flow detection module 455, and is subsequently forwarded on a real-time basis to the PCMCIA interface 43*s* for use by the personal computer 27. The PC card 10*t* in FIG. 27 inputs electrical information from EEG sensors 460 into an EEG module 465 on a real-time basis. The EEG module 465 processes the electrical data and outputs the processed data to a PCMCIA interface 43*t* on a real-time basis for use by the personal computer 27.

Figure 28:
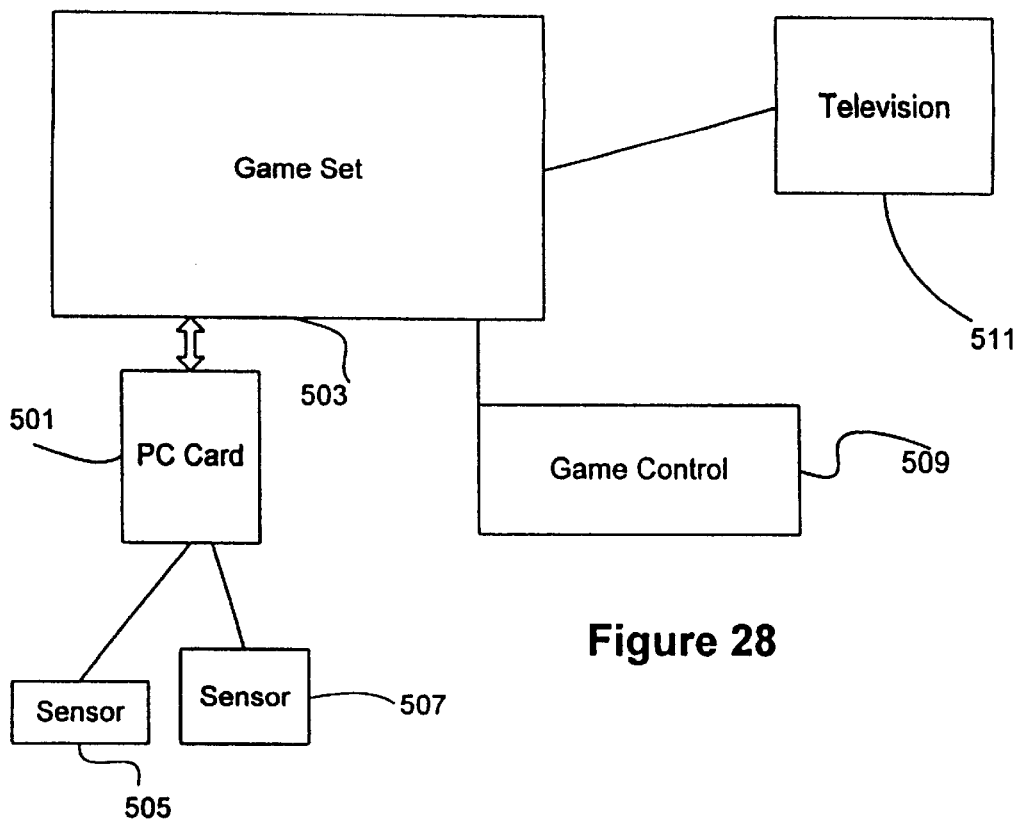
FIG. 28 illustrates a schematic block diagram of a real-time biological data processing PC card for collecting and forwarding on a real-time basis biological data to a game set.

FIG. 28 illustrates a real-time biological data processing PC card 501 connected to a game set 503 for collecting and forwarding on a real-time basis biological data to the game set 503. The biological data is received on a real-time basis into the PC card 501 from one or more sensors 505 and 507. A game control 509 is connected to the game set 503, and a television 511 operates as a monitor. The PC card 501 can be configured similarly to any of the above-described PC cards of the present invention, with an exception of the interface for communicating with the game set. 503. The game set 503 may comprise a game set such as Nintendo® or Sega®. If the game set 503 has a Windows CE operating system and a PCMCIA card slot, then the PC card 501 may be virtually identical to any of the above-discussed PC cards of the present invention. If the game set 503 does not have a PC card slot, then other housings and/or interfaces may be implemented with the PC card 501 to facilitate proper real-time communication between the PC card 501 and the game set 503. One example, compact flash cards and compact flash card housings may be used. As another example, proprietary Nintendo® game set digital interfaces may be used with the PC card 501. The game console 509 may be connected to either the game set 503 or the television 511, and may be linked by a conventional cord or by a wireless communication path.

Figure 29:
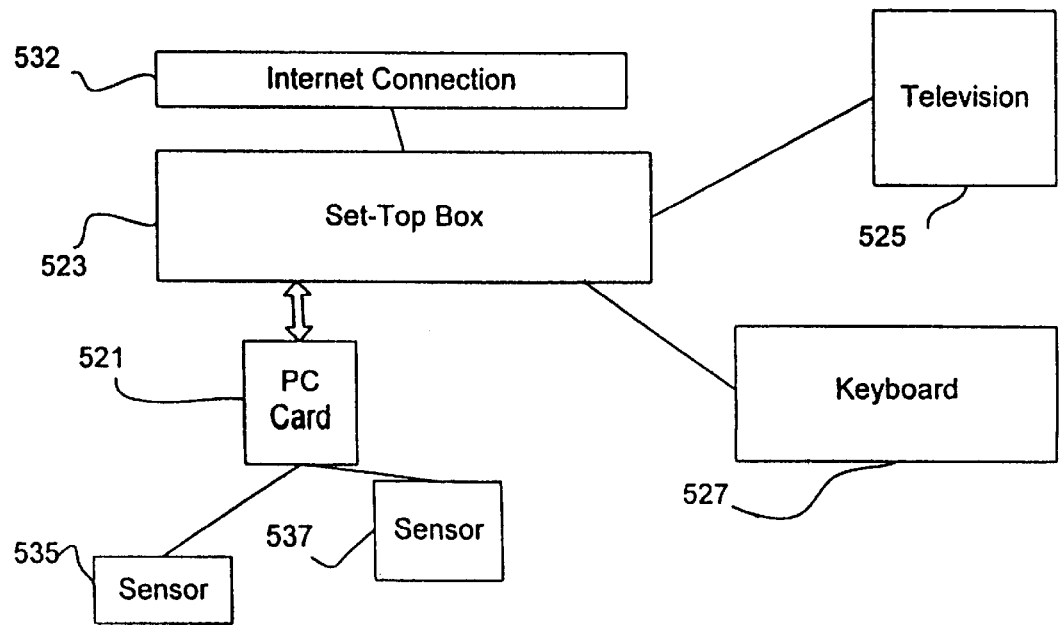
FIG. 29 illustrates a schematic block diagram of a real-time biological data processing PC card for collecting and forwarding on a real-time basis biological data to a set-top box.

FIG. 29 illustrates a real-time biological data processing PC card 521 for collecting and forwarding on a real-time basis biological data to a set-top box 523. The set-top box 523 is connected to a television 525, which operates as a monitor, and is further connected to a keyboard 527. The keyboard 527 may be connected to either the set-top box 523 or the television 525 via a conventional cable or a wireless communication path. In accordance with the illustrated embodiment, the set-top box 523 comprises an Internet connection 532 for facilitating real-time data transfer of biological data from the sensors 535, 537 to one or more receivers on the Internet. The PC card 521 and sensors 535, 537 may comprise any combination of PC cards and sensors discussed in any of the above embodiments. The set-top box 523 can transmit biological data from the sensors 535, 537 on a real-time basis over the Internet to other users, such as a user at a doctor's office or hospital. Additionally, the set-top box 523 can receive biological data on a real-time basis from other users via the Internet connection 532. Information received from other users via the Internet connection 532 can be displayed by the set-top box 523 on the television 525, for example.

Information can be transmitted and received through the Internet connection 532 either on a real-time basis or, alternatively, at predetermined intervals. The set-top box 523 may be configured to automatically dial out and establish an Internet connection, and to transmit or receive real-time biological data over the Internet, at predetermined or user-defined intervals. A patient can conduct tests using one or more sensors, such as the sensors 535 and 537, and at the same time or at a later time, transmit the data to a doctor via the Internet connection 532. In addition to a set-top box 523, Internet telephones, personal computers, wireless Internet computers, network computers or other Internet "appliances" capable of sending real-time data over the Internet may be used. In one embodiment, game sets may be used to transmit or receive the real-time biological data over the Internet.

In modified configurations of the above-described embodiments, some or all of the circuitry and/or components for each of the modules on the personal computer cards can be placed within the host microprocessor system, so long as the card is able to input digital information to the host microprocessor system. Moreover, in other modified configurations circuitry and/or components for each of the modules on the personal computer cards can be placed on the biological data sensors themselves, in addition to or in the alternative to placement of the circuitry and/or components on the host microprocessor system. In embodiments where the signal or signals from the biological data sensor or sensors is simply digitized and forwarded to the host microprocessor system (personal computer, game set, set-top box, etc.) for subsequent processing and interpretation, the signal-conditioning circuitry can comprise the bare-essential elements, such as merely an analog-to-digital converter, for formatting the data from the biological data sensors and forwarding to the host microprocessor system.

In embodiments wherein the host microprocessor system comprises a game set, for example, the personal computer card may have additional initializing data. This may be the case for embodiments wherein other types of host microprocessor systems are used, as well. In some embodiments, the host microprocessor system is loaded with initializing data and instructions, for example, before the personal computer card is loaded into the host microprocessor system. In other embodiments, substantial amounts of data and/or instructions are loaded into the host microprocessor system (or game set, set-top box, etc.) by the personal computer card at the time of insertion of the personal computer card into the host microprocessor system.

In any of the above-described embodiments of the present invention, the personal computer card may comprise a PCMCIA-type card, a card having an interface which is adapted to communicate with a game set, a compact flash card, or any other type of portable card with an interface for transmitting data to a host microprocessor system. An example of a host microprocessor system adapted for accommodating compact flash cards is the Cassiopeia E-10, manufactured by Casio Computer Co. Ltd and described at http://www.casiohpc.com/indes.html.

Although exemplary embodiments of the invention have been shown and described, many other changes, modifications and substitutions, in addition to those set forth in the above paragraphs, may be made by one having ordinary skill in the art without necessarily departing from the spirit and scope of the present invention.

What is claimed is:

1. A portable biological data collection device, comprising:
   at least one biological data receiver for inputting biological data;
   signal-conditioning circuitry operatively coupled to the at least one biological data receiver, the signal-conditioning circuitry comprising at least one analog-to-digital converter and being adapted to output at least one digital signal; and
   a digital interface operatively coupled to the signal-conditioning circuitry the digital interface being adapted to interface the portable biological data collection device to a host microprocessor system, wherein the digital interface comprises a compact flash card interface, the compact flash card interface being adapted to communicate with the host microprocessor system and to relay the at least one digital signal to the host microprocessor system on a real-time basis as the signal conditioning circuitry outputs the at least one digital signal.

2. A portable biological data collection device comprising:
   at least one biological data receiver for inputting biological data;
   signal-conditioning circuitry operatively coupled to the at least one biological data receiver the signal-conditioning circuitry comprising at least one analog-to-digital converter and being adapted to output at least one digital signal; and
   a digital interface operatively coupled to the signal-conditioning circuits the digital interface being adapted to interface the portable biological data collection device to a host microprocessor system wherein the digital interface comprises a game-set card interface, the game-set card interface being adapted to communicate with a game-set host microprocessor system and to relay the at least one digital signal to the game-set host microprocessor system on a real-time basis as the signal conditioning circuitry outputs the at least one digital signal.

3. A personal computer card for collecting biological data, comprising:
   a pulse-oximetry signal receiver, the pulse-oximetry signal receiver being adapted to receive a pulse-oximetry signal from a pulse-oximetry sensor and further being adapted to output the pulse-oximetry signal;
   a blood-pressure signal receiver, the blood-pressure signal receiver being adapted to receive a blood-pressure signal from a blood-pressure sensor and further being adapted to output the blood-pressure signal;
   a temperature signal receiver, the temperature signal receiver being adapted to receive a body-temperature signal from a body-temperature sensor and further being adapted to output the body-temperature signal;
   signal-conditioning circuitry operatively coupled to at least one of the pulse-oximetry signal receiver, the blood-pressure signal receiver and the temperature signal receiver, the signal-conditioning circuitry comprising at least one analog-to-digital converter and being adapted to output at least one digital signal; and
   a personal computer card interface operatively coupled to the signal-conditioning circuitry, the personal computer card interface being adapted to provide an interface between the personal computer card and a host microprocessor system.

4. The personal computer card as set forth in claim 3, wherein the personal computer card interface is adapted to relay the at least one digital signal to the host microprocessor system on a real-time basis as the at least one digital signal is output by the signal-conditioning circuitry.

5. The personal computer card as set forth in claim 3, wherein:
   the personal computer card comprises a personal computer card housing;
   the pulse-oximetry signal receiver is coupled to the personal computer card housing;
   the blood-pressure signal receiver is coupled to the personal computer card housing;
   the temperature signal receiver is coupled to the personal computer card housing;
   the signal-conditioning circuitry is operatively coupled to at least one of the pulse-oximetry signal receiver, the blood-pressure signal receiver and the temperature signal receiver; and
   the personal computer card interface is disposed within the personal computer card housing.

6. The personal computer card as set forth in claim 3, wherein:
   the pulse-oximetry sensor is coupled to the pulse-oximetry signal receiver, the pulse-oximetry sensor being adapted to be placed into close proximity with a patient, to output a pulse-oximetry signal and to relay the pulse-oximetry signal to the pulse-oximetry signal receiver;
   the blood-pressure sensor is coupled to the blood-pressure signal receiver, the blood-pressure sensor being adapted to be placed into close proximity with a patient, to output a blood-pressure signal and to relay the blood-pressure signal to the blood-pressure data receiver;
   the body-temperature sensor is coupled to the temperature signal receiver, the body-temperature sensor being adapted to be placed into close proximity with a patient, to output a body-temperature signal and to relay the body-temperature signal to the temperature signal receiver.

7. A personal computer card for collecting biological data, comprising:
   a temperature signal receiver, the temperature signal receiver being adapted to receive a body-temperature signal from a body-temperature sensor and further being adapted to output the body-temperature signal;

signal-conditioning circuitry operatively coupled to the temperature signal receiver, the signal-conditioning circuitry being adapted to receive the body-temperature signal from the temperature signal receiver and to convert the body-temperature signal into digitized body-temperature data; and a personal computer card interface operatively coupled to the signal-conditioning circuitry, the personal computer card interface being adapted to provide an interface between the personal computer card and a host microprocessor system.

8. The personal computer card as set forth in claim 7, wherein the personal computer card interface is adapted to relay the digitized body-temperature data to the host computer on a real-time basis as the body-temperature signal is converted by the signal conditioning circuitry.

9. The personal computer card as set forth in claim 7, wherein:

the personal computer card comprises a personal computer card housing;

the temperature signal receiver is coupled to the personal computer card housing;

the signal-conditioning circuitry is operatively coupled to the temperature signal receiver; and the personal computer card interface is disposed within the personal computer card housing.

10. The personal computer card as set forth in claim 7, wherein the body-temperature sensor is coupled to the temperature signal receiver, the body-temperature sensor being adapted to be placed into close proximity with a patient, to output a body-temperature signal and to relay the body-temperature signal to the temperature signal receiver.

11. A personal computer card for collecting biological data, comprising:

a blood-pressure signal receiver, the blood-pressure signal receiver being adapted to receive a blood-pressure signal from a blood-pressure sensor and further being adapted to output the blood-pressure signal;

signal-conditioning circuitry operatively coupled to the blood-pressure signal receiver, the signal-conditioning circuitry being adapted to receive the blood-pressure signal from the blood-pressure signal receiver and to convert the blood-pressure signal into digitized blood-pressure data; and a personal computer card interface operatively coupled to the signal-conditioning circuitry, the personal computer card interface being adapted to provide an interface between the personal computer card and a host microprocessor system.

12. The personal computer card as set forth in claim 11, wherein the personal computer card interface is adapted to relay the digitized blood-pressure data to the host computer on a real-time basis as the blood-pressure signal is converted by the signal conditioning circuitry.

13. The personal computer card as set forth in claim 11, wherein:

the personal computer card comprises a personal computer card housing;

the blood-pressure signal receiver is coupled to the personal computer card housing;

the signal-conditioning circuitry is operatively coupled to the blood-pressure signal receiver; and the personal computer card interface is disposed within the personal computer card housing.

14. The personal computer card as set forth in claim 11, wherein the blood-pressure data sensor is coupled to the blood-pressure signal receiver, the blood-pressure data sensor being adapted to be placed into close proximity with a patient, to output a blood-pressure signal and to relay the blood-pressure signal to the blood-pressure receiver.

15. A personal computer card for collecting biological data, comprising:

a flow signal receiver, the flow signal receiver being adapted to receive a flow signal from a flow sensor and further being adapted to output the flow signal;

a line pressure signal receiver, the line pressure signal receiver being adapted to receive a line pressure signal from a line pressure sensor and further being adapted to output the line pressure signal;

signal-conditioning circuitry operatively coupled to at least one of the flow signal receiver and the line pressure signal receiver, the signal-conditioning circuitry comprising at least one analog-to-digital converter and being adapted to output at least one digital signal; and a personal computer card interface operatively coupled to the signal-conditioning circuitry, the personal computer card interface being adapted to provide an interface between the personal computer card and a host microprocessor system.

16. The personal computer card as set forth in claim 15, wherein the personal computer card interface is adapted to relay the at least one digital signal to the host microprocessor system on a real-time basis as the at least one digital signal is output by the signal-conditioning circuitry.

17. The personal computer card as set forth in claim 15, wherein:

the personal computer card comprises a personal computer card housing;

the flow signal receiver is coupled to the personal computer card housing;

the line pressure signal receiver is coupled to the personal computer card housing;

the signal-conditioning circuitry is operatively coupled to at least one of the flow signal receiver and the line pressure signal receiver; and the personal computer card interface is disposed within the personal computer card housing.

18. The personal computer card as set forth in claim 15, wherein:

the flow sensor is coupled to the flow signal receiver, the flow sensor being adapted to contact a line of a ventilator, to output a flow signal and to relay the flow signal to the flow signal receiver; and the line pressure sensor is coupled to the line pressure signal receiver, the line pressure sensor being adapted to contact a line of a ventilator, to output a line pressure signal and to relay the line pressure signal to the line pressure data receiver.

19. The personal computer card as set forth in claim 18, wherein the flow signal receiver comprises at least one pressure sensor; and the line pressure signal receiver comprises a pressure sensor.

20. A personal computer card for collecting biological data, comprising:

flow signal receiver, the flow signal receiver being adapted to receive a flow signal from a flow sensor and further being adapted to output the flow signal;

signal-conditioning circuitry operatively coupled to the flow signal receiver, the signal-conditioning circuitry being adapted to receive the flow signal from the flow signal receiver and to convert the flow signal into digitized flow data; and a personal computer card interface operatively coupled to the signal-conditioning circuitry, the personal computer card interface being adapted to provide an interface between the personal computer card and a host microprocessor system.

21. The personal computer card as set forth in claim 20, wherein the personal computer card interface is adapted to relay the digitized flow data to the host computer on a real-time basis as the flow signal is converted by the signal conditioning circuitry.

22. The personal computer card as set forth in claim 20, wherein:

the personal computer card comprises a personal computer card housing;

the flow signal receiver is coupled to the personal computer card housing;

the signal-conditioning circuitry is operatively coupled to the flow signal receiver; and the personal computer card interface is disposed within the personal computer card housing.

23. The personal computer card as set forth in claim 20, wherein the flow sensor is coupled to the flow signal receiver, the flow sensor being adapted to contact a line of a ventilator, to output a flow signal and to relay the flow signal to the flow signal receiver.

24. The personal computer card as set forth in claim 23, wherein the flow signal receiver comprises at least one pressure sensor.

25. A personal computer card for collecting biological data, comprising:

a line pressure signal receiver, the line pressure signal receiver being adapted to receive a line pressure signal from a line pressure sensor and further being adapted to output the line pressure signal;

signal-conditioning circuitry operatively coupled to the line pressure signal receiver, the signal-conditioning circuitry being adapted to receive the line pressure signal from the line pressure signal receiver and to convert the line pressure signal into digitized line pressure data; and a personal computer card interface operatively coupled to the signal-conditioning circuitry, the personal computer card interface being adapted to provide an interface between the personal computer card and a host microprocessor system.

26. The personal computer card as set forth in claim 25, wherein the personal computer card interface is adapted to relay the digitized line pressure data to the host computer on a real-time basis as the line pressure signal is converted by the signal conditioning circuitry.

27. The personal computer card as set forth in claim 25, wherein:

the personal computer card comprises a personal computer card housing;

the line pressure signal receiver is coupled to the personal computer card housing;

the signal-conditioning circuit is operatively coupled to the line pressure signal receiver; and the personal computer card interface is disposed within the personal computer card housing.

28. The personal computer card as set forth in claim 25, wherein the line pressure sensor is coupled to the line pressure signal receiver, the line pressure sensor being adapted to contact a line of a ventilator, to output a line pressure signal and to relay the line pressure signal to the line pressure receiver.

29. The personal computer card as set forth in claim 28, wherein the line pressure signal receiver comprises a pressure sensor.

30. A personal computer card for collecting biological data, comprising:

a pulse-oximetry signal receiver, the pulse-oximetry signal receiver being adapted to receive a pulse-oximetry signal from a pulse-oximetry sensor and further being adapted to output the pulse-oximetry signal;

a respiration-rate signal receiver, the respiration-rate signal receiver being adapted to receive a respiration-rate signal from a respiration-rate sensor and further being adapted to output the respiration-rate signal;

a nasal-air pressure/thermistor signal receiver, the nasal-air pressure/thermistor signal receiver being adapted to receive a nasal-air pressure/temperature signal from a nasal-air pressure thermistor sensor and further being adapted to output the nasal-air pressure/thermistor signal;

signal-conditioning circuitry operatively coupled to at least one of the pulse-oximetry signal receiver, the respiration-rate signal receiver and the nasal-air pressure/thermistor signal receiver, the signal-conditioning circuitry comprising at least one analog-to-digital converter and being adapted to output at least one digital signal; and a personal computer card interface operatively coupled to the signal-conditioning circuitry, the personal computer card interface being adapted to provide an interface between the personal computer card and a host microprocessor system.

31. The personal computer card as set forth in claim 30, wherein the personal computer card interface is adapted to relay the at least one digital signal to the host microprocessor system on a real-time basis as the at least one digital signal is output by the signal-conditioning circuitry.

32. The personal computer card as set forth in claim 30, wherein:

the personal computer card comprises a personal computer card housing;

the pulse-oximetry signal receiver is coupled to the personal computer card housing;

the respiration-rate signal receiver is coupled to the personal computer card housing;

the nasal-air pressure/thermistor signal receiver is coupled to the personal computer card housing;

the signal-conditioning circuitry is operatively coupled to at least one of the pulse-oximetry signal receiver, the respiration-rate signal receiver and the nasal-air pressure/thermistor signal receiver; and the personal computer card interface is disposed within the personal computer card housing.

33. The personal computer card as set forth in claim 30, wherein:

the pulse-oximetry sensor is coupled to the pulse-oximetry signal receiver, the pulse-oximetry sensor being adapted to be placed into close proximity with a patient, to output a pulse-oximetry signal and to relay the pulse-oximetry signal to the pulse-oximetry signal receiver;

the respiration-rate sensor is coupled to the respiration-rate signal receiver, the respiration-rate sensor being adapted to be placed into close proximity with a patient, to output a respiration-rate signal and to relay the respiration-rate signal to the respiration-rate signal receiver;

the nasal-air pressure/thermistor sensor is coupled to the nasal-air pressure/thermistor signal receiver, the nasal-air pressure/thermistor sensor being adapted to be placed into close proximity with a patient, to output a nasal-air pressure signal and to relay the nasal-air pressure/thermistor signal to the nasal-air pressure/thermistor signal receiver.

34. The personal computer card as set forth in claim 31, wherein:

the respiration-rate sensor comprises a chest band and a microphone; and the nasal-air pressure thermistor sensor comprises a nasal cannula.

35. The personal computer card as set forth in claim 34, wherein:

the respiration-rate signal receiver comprises a strain gauge; and the nasal-air pressure/thermistor signal receiver comprises a pressure/temperature sensor.

36. A personal computer card for collecting biological data, comprising:

a respiration-rate signal receiver, the respiration-rate signal receiver being adapted to receive a respiration-rate signal from a respiration-rate sensor and further being adapted to output the respiration-rate signal;

signal-conditioning circuitry operatively coupled to the respiration-rate signal receiver, the signal-conditioning circuitry being adapted to receive the respiration-rate signal from the respiration-rate signal receiver and to convert the respiration-rate signal into digitized respiration-rate data; and a personal computer card interface operatively coupled to the signal-conditioning circuitry, the personal computer card interface being adapted to provide an interface between the personal computer card and a host microprocessor system.

37. The personal computer card as set forth in claim 36, wherein the personal computer card interface is adapted to relay the digitized respiration-rate data to the host computer on a real-time basis as the respiration-rate signal is converted by the signal conditioning circuitry.

38. The personal computer card as set forth in claim 36, wherein:

the personal computer card comprises a personal computer card housing;

the respiration-rate signal receiver is coupled to the personal computer card housing;

the signal-conditioning circuitry is operatively coupled to the respiration-rate receiver; and the personal computer card interface is disposed within the personal computer card housing.

39. The personal computer card as set forth in claim 36, wherein the respiration-rate sensor is coupled to the respiration-rate signal receiver, the respiration-rate sensor being adapted to be placed into close proximity with a patient, to output a respiration-rate signal and to relay the respiration-rate signal to the respiration-rate receiver.

40. The personal computer card as set forth in claim 39, wherein the respiration-rate signal receiver comprises a strain gauge.

41. A personal computer card for collecting biological data, comprising:

a nasal-air pressure/thermistor signal receiver, the nasal-air pressure/thermistor signal receiver being adapted to receive a nasal-air pressure/thermistor signal from a nasal-air pressure thermistor sensor and further being adapted to output the nasal-air pressure/thermistor signal;

signal-conditioning circuitry operatively coupled to the nasal-air pressure/thermistor signal receiver, the signal-conditioning circuitry being adapted to receive the nasal-air pressure/thermistor signal from the nasal-air pressure/thermistor signal receiver and to convert the nasal-air pressure/thermistor signal into digitized nasal-air pressure/thermistor data;

a personal computer card interface operatively coupled to the signal-conditioning circuitry, the personal computer card interface being adapted to provide an interface between the personal computer card and a host microprocessor system.

42. The personal computer card as set forth in claim 41, wherein the personal computer card interface is adapted to relay the digitized nasal-air pressure thermistor data to the host computer on a real-time basis as the nasal-air pressure/thermistor signal is converted by the signal conditioning circuitry.

43. The personal computer card as set forth in claim 41, wherein:

the personal computer card comprises a personal computer card housing;

the nasal-air pressure/thermistor signal receiver is coupled to the personal computer card housing;

the signal-conditioning circuitry is operatively coupled to the nasal-air pressure/thermistor signal receiver; and the personal computer card interface is disposed within the personal computer card housing.

44. The personal computer card as set fort in claim 41, wherein the nasal-air pressure/thermistor sensor is coupled to the nasal-air pressure/thermistor signal receiver, the nasal-air pressure/thermistor sensor-being adapted to be placed into close proximity with a patient to output a nasal-air pressure/thermistor signal and to relay the nasal-air pressure/thermistor signal to the nasal-air pressure/thermistor signal receiver.

45. The personal computer card as set forth in claim 44, wherein the nasal-air pressure thermistor signal receiver comprises a pressure/temperature sensor.

46. A personal computer card for collecting biological data, comprising:

an electrocardiography (ECG) signal receiver, the ECG signal receiver being adapted to receive ECG signals from a plurality of ECG sensors and further being adapted to output the ECG signals;

signal-conditioning circuitry operatively coupled to the ECG signal receiver, the signal-conditioning circuitry being adapted to receive the ECG signals from the ECG signal receiver and to output digitized ECG data; and a personal computer card interface operatively coupled to the signal-conditioning circuitry, the personal computer card interface being adapted to provide an interface between the personal computer card and a host microprocessor system and to relay the digitized ECG data to the host microprocessor system on a real-time basis as the digitized ECG data is output by the signal-conditioning circuitry.

47. The personal computer card as set forth in claim 46, wherein:

the personal computer card comprises a personal computer card housing;

the ECG signal receiver is coupled to the personal computer card housing;

the signal-conditioning circuitry is operatively coupled to the ECG signal receiver; and the personal computer card interface is disposed within the personal computer card housing.

48. The personal computer card as set forth in claim 46, wherein:

the plurality of ECG sensors are coupled to the ECG signal receiver, the plurality of ECG sensors being adapted to be placed into close proximity with a patient, to output ECG signals and to relay the ECG signals to the ECG signal receiver.

49. A personal computer card for collecting biological data, comprising:

a hydrogen signal receiver, the hydrogen signal receiver being adapted to receive a hydrogen signal from a hydrogen sensor and further being adapted to output the hydrogen signal;

signal-conditioning circuitry operatively coupled to the hydrogen signal receiver, the signal-conditioning circuitry being adapted to receive the hydrogen signal from the hydrogen signal receiver and to output digitized hydrogen data; and a personal computer card interface operatively coupled to the signal-conditioning circuitry, the personal computer card interface being adapted to provide an interface between the personal computer card and a host microprocessor system.

50. The personal computer card as set forth in claim 49, wherein the personal computer card interface is adapted to relay the digitized hydrogen data to the host microprocessor system on a real-time basis as the digitized hydrogen data is output by the signal-conditioning circuitry.

51. The personal computer card as set forth in claim 49, wherein:

the personal computer card comprises a personal computer card housing;

the hydrogen signal receiver is coupled to the personal computer card housing;

the signal-conditioning circuitry is operatively coupled to the hydrogen signal receiver; and the personal computer card interface is disposed within the personal computer card housing.

52. The personal computer card as set forth in claim 49, wherein the hydrogen sensor is coupled to the hydrogen signal receiver, the hydrogen sensor being adapted to be placed into close proximity with a patient, to output a hydrogen signal and to relay the hydrogen signal to the hydrogen signal receiver.

53. A personal computer card for collecting biological data, comprising:

an alcohol signal receiver, the alcohol signal receiver being adapted to receive an alcohol signal from an alcohol sensor and further being adapted to output the alcohol signal;

signal-conditioning circuitry operatively coupled to the alcohol signal receiver, the signal-conditioning circuitry being adapted to receive the alcohol signal from the alcohol signal receiver and to output digitized alcohol data; and a personal computer card interface operatively coupled to the signal-conditioning circuitry, the personal computer card interface being adapted to provide an interface between the personal computer card and a host microprocessor system.

54. The personal computer card as set forth in claim 53, wherein the personal computer card interface is adapted to relay the digitized alcohol data to the host microprocessor system on a real-time basis as the digitized alcohol data is output by the signal-conditioning circuitry.

55. The personal computer card as set forth in claim 53, wherein:

the personal computer card comprises a personal computer card housing;

the alcohol signal receiver is coupled to the personal computer card housing;

the signal-conditioning circuitry is operatively coupled to the alcohol signal receiver; and the personal computer card interface is disposed within the personal computer card housing.

56. The personal computer card as set forth in claim 53, wherein the alcohol sensor is coupled to the alcohol signal receiver, the alcohol sensor being adapted to be placed into close proximity with a patient, to output an alcohol signal and to relay the alcohol signal to the alcohol signal receiver.

57. A personal computer card for collecting biological data, comprising:

a pulse-oximetry signal receiver, the pulse-oximetry signal receiver being adapted to receive a pulse-oximetry signal from a pulse-oximetry sensor and further being adapted to output the pulse-oximetry signal;

a respiration-rate signal receiver, the respiration-rate signal receiver being adapted to receive a respiration-rate signal from a respiration-rate sensor and further being adapted to output the respiration-rate signal;

a nasal-air pressure signal receiver, the nasal-air pressure signal receiver being adapted to receive a nasal-air pressure signal from a nasal-air pressure sensor and further being adapted to output the nasal-air pressure signal;

a sound signal receiver, the sound signal receiver being adapted to receive a sound signal from a sound sensor and further being adapted to output the sound signal;

a motion signal receiver, the motion signal receiver being adapted to receive a motion signal from a motion sensor and further being adapted to output the motion signal;

a position signal receiver, the position signal receiver being adapted to receive a position signal from a position sensor and further being adapted to output the position signal;

an electrocardiography (ECG) signal receiver, the ECG signal receiver being adapted to receive ECG signals from a plurality of ECG sensors and further being adapted to output the ECG signals;

signal-conditioning circuitry operatively coupled to at least one of the pulse-oximetry signal receiver, the respiration-rate signal receiver, the nasal-air pressure signal receiver, the sound signal receiver, the motion signal receiver, the position signal receiver and the ECG signal receiver, the signal-conditioning circuitry comprising at least one analog-to-digital converter and being adapted to output at least one digital signal; and a personal computer card interface operatively coupled to the signal-conditioning circuitry, the personal computer card interface being adapted to provide an interface between the personal computer card and a host microprocessor system.

58. The personal computer card as set forth in claim 57, wherein the personal computer card interface is adapted to relay the at least one digital signal to the host microprocessor system on a real-time basis as the at least one digital signal is output by the signal-conditioning circuitry.

59. The personal computer card as set forth in claim 57, wherein:
 the personal computer card comprises a personal computer card housing;
 the pulse-oximetry signal receiver is coupled to the personal computer card housing;
 the respiration-rate signal receiver is coupled to the personal computer card housing;
 the nasal-air pressure/thermistor signal receiver is coupled to the personal computer card housing;
 the sound signal receiver is coupled to the personal computer card housing;
 the motion signal receiver is coupled to the personal computer card housing;
 the position signal receiver is coupled to the personal computer card housing;
 the ECG signal receiver is coupled to the personal computer card housing;
 the signal-conditioning circuitry is operatively coupled to at least one of the pulse-oximetry signal receiver, the respiration-gate signal receiver, the nasal-air pressure/thermistor signal receiver, the sound signal receiver, the motion signal receiver, the position signal receiver and the ECG signal receiver; and
 the personal computer card interface is disposed within the personal computer card housing.

60. The personal computer card as set forth in claim 57, wherein:
 the pulse-oximetry sensor is coupled to the pulse-oximetry signal receiver, the pulse-oximetry sensor being adapted to be placed into close proximity with a patient, to output a pulse-oximetry signal and to relay the pulse-oximetry signal to the pulse-oximetry signal receiver;
 the respiration-rate sensor is coupled to the respiration-rate signal receiver, the respiration-rate sensor being adapted to be placed into close proximity with a patient, to output a respiration-rate signal and to relay the respiration-rate signal to the respiration-rate signal receiver;
 the nasal-air pressure/thermistor sensor is coupled to the nasal-air pressure/thermistor signal receiver, the nasal-air pressure/thermistor sensor being adapted to be placed into close proximity with a patient, to output a nasal-air pressure/thermistor signal and to relay the nasal-air pressure thermistor signal to the nasal-air pressure/thermistor signal receiver;
 the sound sensor is coupled to the sound signal receiver, the sound sensor being adapted to be placed into close proximity with a patient, to output a sound signal and to relay the sound signal to the sound signal receiver;
 the motion sensor is coupled to the motion signal receiver, the motion sensor being adapted to be placed into close proximity with a patient, to output a motion signal and to relay the motion signal to the motion signal receiver;
 the position sensor is coupled to the position signal receiver, the position sensor being adapted to be placed into close proximity with a patient,-to output a position signal and to relay the position signal to the position signal receiver; and
 the plurality of ECG sensors are coupled to the ECG signal receiver, the plurality of ECG sensors being adapted to be placed into close proximity with a patient, to output ECG signals and to relay the ECG signals to the ECG signal receiver.

61. A personal computer card for collecting biological data, comprising:
 a pulse-oximetry signal receiver, the pulse-oximetry signal receiver being adapted to receive a pulse-oximetry signal from a pulse-oximetry sensor and further being adapted to output the pulse-oximetry signal;
 a respiration-rate signal receiver, the respiration-rate signal receiver being adapted to receive a respiration-rate signal from a respiration-rate sensor and further being adapted to output the respiration-rate signal;
 a nasal-air pressure/thermistor signal receiver, the nasal-air pressure/thermistor signal receiver being adapted to receive a nasal-air pressure/thermistor signal from a nasal-air pressure/thermistor sensor and further being adapted to output the nasal-air pressure/thermistor signal;
 a sound signal receiver, the sound signal receiver being adapted to receive a sound signal from a sound sensor and further being adapted to output the sound signal;
 a motion signal receiver, the motion signal receiver being adapted to receive a motion signal from a motion sensor and further being adapted to output the motion signal;
 a position signal receiver, the position signal receiver being adapted to receive a position signal from a position sensor and further being adapted to output the position signal;
 an electrocardiography (ECG) signal receiver, the ECG signal receiver being adapted to receive ECG signals from a plurality of ECG sensors and further being adapted to output the ECG signals;
 an electroencepholograhy (EEG) signal receiver, the EEG signal receiver being adapted to receive EEG signals from a plurality of EEG sensors and further being adapted to output the EEG signals;
 an electrooculogram (EOG) signal receiver, the EOG signal receiver being adapted to receive EOG signals from a plurality of EOG sensors and further being adapted to output the EOG signals;
 an electromyography (EMG) signal receiver, the EMG signal receiver being adapted to receive EMG signals from a plurality of EMG sensors and further being adapted to output the EMG signals;
 signal-conditioning circuitry operatively coupled to at least one of the pulse-oximetry signal receiver, the respiration-rate signal receiver, the nasal-air pressure signal receiver, the sound signal receiver, the motion signal receiver, the position signal receiver, the ECG signal receiver, the EEG signal receiver, the EOG signal receiver and the EMG signal receiver, the signal-conditioning circuitry comprising at least one analog-to-digital converter and being adapted to output at least one digital signal; and
 a personal computer card interface operatively coupled to the signal-conditioning circuitry, the personal computer card interface being adapted to provide an interface between the personal computer card and a host microprocessor system.

62. The personal computer card as set forth in claim 61, wherein the personal computer card interface is adapted to relay the at least one digital signal to the host microprocessor system on a real-time basis as the at least one digital signal is output by the signal-conditioning circuitry.

63. The personal computer card as set forth in claim 61, wherein:

the personal computer card comprises a personal computer card housing;

the pulse-oximetry signal receiver is coupled to the personal computer card housing;

the respiration-rate signal receiver is coupled to the personal computer card housing;

the nasal-air pressure/thermistor signal receiver is coupled to the personal computer card housing;

the sound signal receiver is coupled to the personal computer card housing;

the motion signal receiver is coupled to the personal computer card housing; the position signal receiver is coupled to the personal computer card housing;

the ECG signal receiver is coupled to the personal computer card housing;

the EEG signal receiver is coupled to the personal computer card housing;

the EOG signal receiver is coupled to the personal computer card housing;

the EMG signal receiver is coupled to the personal computer card housing;

the signal-conditioning circuitry is operatively coupled to at least one of the pulse-oximetry signal receiver, the respiration-rate signal receiver, the nasal-air pressure signal receiver, the sound signal receiver, the motion signal receiver, the position signal receiver, the ECG signal receiver, the EEG signal receiver, the EOG signal receiver and the EMG signal receiver; and the personal computer card interface is disposed within the personal computer card housing.

64. The personal computer card as set forth in claim 61, wherein:

the pulse-oximetry sensor is coupled to the pulse-oximetry signal receiver, the pulse-oximetry sensor being adapted to be placed into close proximity with a patient, to output a pulse-oximetry signal and to relay the pulse-oximetry signal to the pulse-oximetry signal receiver;

the respiration-rate sensor is coupled to the respiration-rate signal receiver, the respiration-rate sensor being adapted to be placed into close proximity with a patient, to output a respiration-rate signal and to relay the respiration-rate signal to the respiration-rate signal receiver;

the nasal-air pressure/thermistor sensor is coupled to the nasal-air pressure/thermistor signal receiver, the nasal-air pressure/thermistor sensor to be placed into close proximity with a patient, to output a nasal-air pressure/thermistor signal and to relay the nasal-air pressure/thermistor signal to the nasal-air pressure/thermistor signal receiver;

the sound sensor is coupled to the sound signal receiver, the sound sensor being adapted to be placed into close proximity with a patient, to output a sound signal and to relay the sound signal to the sound signal receiver;

the motion sensor is coupled to the motion signal receiver, the motion sensor being adapted to be placed into close proximity with a patient, to output a motion signal and to relay the motion signal to the motion signal receiver;

the position sensor is coupled to the position signal receiver, the position sensor being adapted to be placed into close proximity with a patient, to output a position signal and to relay the position signal to the position signal receiver;

the plurality of ECG sensors are coupled to the ECG signal receiver, the plurality of ECG sensors being adapted to be placed into close proximity with a patient, to output ECG signals and to relay the ECG signals to the ECG signal receiver;

the plurality of EEG sensors are coupled to the EEG signal receiver, the plurality of EEG sensors being adapted to be placed into close proximity with a patient, to output EEG signals and to relay the EEG signals to the EEG signal receiver;

the plurality of EOG sensors are coupled to the EOG signal receiver, the plurality of EOG sensors being adapted to be placed into close proximity with a patient, to output EOG signals and to relay the EOG signals to the EOG signal receiver; and the plurality of EMG sensors are coupled to the EMG signal receiver, the plurality of EMG sensors being adapted to be placed into close proximity with a patient, to output EMG signals and to relay the EMG signals to the EMG signal receiver.

65. A personal computer card for collecting biological data, comprising:

a sound signal receiver, the sound signal receiver being adapted to receive a sound signal from a sound sensor and further being adapted to output the sound signal;

signal-conditioning circuitry operatively coupled to the sound signal receiver, the signal-conditioning circuitry being adapted to receive the sound signal from the sound signal receiver and to convert the sound signal into digitized sound signal data; and a personal computer card interface operatively coupled to the signal-conditioning circuitry, the personal computer card interface being adapted to provide an interface between the personal computer card and a host microprocessor system.

66. The personal computer card as set forth in claim 65, wherein the personal computer card interface is adapted to relay the digitized sound signal data to the host computer on a real-time basis as the sound signal is converted by the signal conditioning circuitry.

67. The personal computer card as set forth in claim 65, wherein:

the personal computer card comprises a personal computer card housing;

the sound signal receiver is coupled to the personal computer card housing;

the signal-conditioning circuitry is operatively coupled to the sound signal receiver; and the personal computer card interface is disposed within the personal computer card housing.

68. The personal computer card as set forth in claim 65, wherein the sound sensor is coupled to the sound signal receiver, the sound sensor being adapted to be placed into close proximity with a patient, to output a sound signal and to relay the sound signal to the sound signal receiver.

69. A personal computer card for collecting biological data, comprising:

a motion signal receiver, the motion signal receiver being adapted to receive a motion signal from a motion sensor and further being adapted to output the motion signal;

signal-conditioning circuitry operatively coupled to the motion signal receiver, the signal-conditioning circuitry being adapted to receive the motion signal from the motion signal receiver and to convert the motion signal into digitized motion signal data; and a personal computer card interface operatively coupled to the signal-conditioning circuitry, the personal computer card interface being adapted to provide an interface between the personal computer card and a host microprocessor system.

70. The personal computer card as set forth in claim 69, wherein the personal computer card interface is adapted to relay the digitized motion signal data to the host computer on a real-time basis as the motion signal is converted by the signal conditioning circuitry.

71. The personal computer card as set forth in claim 69, wherein:

the personal computer card comprises a personal computer card housing;

the motion signal receiver is coupled to the personal computer card housing;

the signal-conditioning circuitry is operatively coupled to the motion signal receiver; and the personal computer card interface is disposed within the personal computer card housing.

72. The personal computer card as set forth in claim 70, wherein the motion sensor is coupled to the motion signal receiver, the motion sensor being adapted to be placed into close proximity with a patient, to output a motion signal and to relay the motion signal to the motion signal receiver.

73. A personal computer card for collecting biological data, comprising:

a position signal receiver, the position signal receiver being adapted to receive a position signal from a position sensor and further being adapted to output the position signal;

signal-conditioning circuitry operatively coupled to the position signal receiver, the signal-conditioning circuitry being adapted to receive the position signal from the position signal receiver and to convert the position signal into digitized position signal data; and a personal computer card interface operatively coupled to the signal-conditioning circuitry, the personal computer card interface being adapted to provide an interface between the personal computer card and a host microprocessor system.

74. The personal computer card as set forth in claim 73, wherein the personal computer card interface is adapted to relay the digitized position signal data to the host computer on a real-time basis as the position signal is converted by the signal conditioning circuitry.

75. The personal computer card as set forth in claim 73, wherein:

the personal computer card comprises a personal computer card housing;

the position signal receiver is coupled to the personal computer card housing;

the signal-conditioning circuitry is operatively coupled to the position signal receiver; and the personal computer card interface is disposed within the personal computer card housing.

76. The personal computer card as set forth in claim 73, wherein the position sensor is coupled to the position signal receiver, the position sensor being adapted to be placed into close proximity with a patient, to output a position signal and to relay the position signal to the position signal receiver.

77. A personal computer card for collecting biological data, comprising:

an electrooculogram (EOG) signal receiver, the EOG signal receiver being adapted to receive EOG signals from a plurality of EOG sensors and further being adapted to output the EOG signals;

signal-conditioning circuitry operatively coupled to the EOG signal receiver, the signal-conditioning circuitry being adapted to receive the EOG signals from the EOG signal receiver and to output digitized EOG data; and a personal computer card interface operatively coupled to the signal-conditioning circuitry, the personal computer card interface being adapted to provide an interface between the personal computer card and a host microprocessor system.

78. The personal computer card as set forth in claim 77, wherein the personal computer card interface is adapted to relay the digitized EOG data to the host microprocessor system on a real-time basis as the digitized EOG data is output by the signal-conditioning circuitry.

79. The personal computer card as set forth in claim 77, wherein:

the personal computer card comprises a personal computer card housing;

the EOG signal receiver is coupled to the personal computer card housing;

the signal-conditioning circuitry is operatively coupled to the EOG signal receiver; and the personal computer card interface is disposed within the personal computer card housing.

80. The personal computer card as set forth in claim 77, wherein:

the plurality of EOG sensors are coupled to the EOG signal receiver, the plurality of EOG sensors being adapted to be placed into close proximity with a patient, to output EOG signals and to relay the EOG signals to the EOG signal receiver.

81. A personal computer card for collecting biological data, comprising:

an electromyography (EMG) signal receiver, the EMG signal receiver being adapted to receive EMG signals from a plurality of EMG sensors and further being adapted to output the EMG signals;

signal-conditioning circuitry operatively coupled to the EMG signal receiver, the signal-conditioning circuitry being adapted to receive the EMG signals from the EMG signal receiver and to output digitized EMG data; and a personal computer card interface operatively coupled to the signal-conditioning circuitry, the personal computer card interface being adapted to provide an interface between the personal computer card and a host microprocessor system.

82. The personal computer card as set forth in claim 81, wherein the personal computer card interface is adapted to relay the digitized EMG data to the host microprocessor system on a real-time basis as the digitized EMG data is output by the signal-conditioning circuitry.

83. The personal computer card as set forth in claim 81, wherein:

the personal computer card comprises a personal computer card housing;

the EMG signal receiver is coupled to the personal computer card housing;

the signal-conditioning circuitry is operatively coupled to the EMG signal receiver; and the personal computer card interface is disposed within the personal computer card housing.

84. The personal computer card as set forth in claim 81, wherein:

the plurality of EMG sensors are coupled to the EMG signal receiver, the plurality of EMG sensors being adapted to be placed into close proximity with a patient, to output EMG signals and to relay the EMG signals to the EMG signal receiver.

85. A personal computer card for collecting biological data, comprising:

a fetal heart-rate signal receiver, the fetal heart-rate signal receiver being adapted to receive a fetal heart-rate signal from a fetal heart-rate sensor and further being adapted to output the fetal heart-rate signal;

a contraction signal receiver, the contraction signal receiver being adapted to receive a contraction signal from a contraction sensor and further being adapted to output the contraction signal;

signal-conditioning circuitry operatively coupled to at least one of the fetal heart-rate signal receiver and the contraction signal receiver, the signal-conditioning circuitry comprising at least one analog-to-digital converter and being adapted to output at least one digital signal; and a personal computer card interface operatively coupled to the signal-conditioning circuitry, the personal computer card interface being adapted to provide an interface between the personal computer card and a host microprocessor system.

86. The personal computer card as set forth in claim 85, wherein the personal computer card interface is adapted to relay the at least one digital signal to the host microprocessor system on a real-time basis as the at least one digital signal is output by the signal-conditioning circuitry.

87. The personal computer card as set forth in claim 85, wherein:

the personal computer card comprises a personal computer card housing;

the fetal heart-rate signal receiver is coupled to the personal computer card housing;

the contraction signal receiver is coupled to the personal computer card housing;

the signal-conditioning circuitry is operatively coupled to at least one of the fetal heart-rate receiver and the contraction signal receiver; and the personal computer card interface is disposed within the personal computer card housing.

88. The personal computer card as set forth in claim 85, wherein:

the fetal heart-rate sensor is coupled to the fetal heart-rate signal receiver, the fetal heart-rate sensor being adapted to be placed into close proximity with a patient, to output a fetal heart-rate signal and to relay the fetal heart-rate signal to the fetal heart-rate signal receiver; and the contraction sensor is coupled to the contraction signal receiver, the contraction sensor being adapted to be placed into close proximity with a patient, to output a contraction signal and to relay the contraction signal to the contraction signal receiver.

89. A personal computer card for collecting biological data, comprising: a fetal heart-rate signal receiver, the fetal heart-rate signal receiver being adapted to receive a fetal heart-rate signal from a fetal heart-rate sensor and further being adapted to output the fetal heart-rate signal;

signal-conditioning circuitry operatively coupled to the fetal heart-rate signal receiver, the signal-conditioning circuitry being adapted to receive the fetal heart-rate signal from the fetal heart-rate signal receiver and to convert the fetal heart-rate signal into digitized fetal heart-rate data; and a personal computer card interface operatively coupled to the signal-conditioning circuitry, the personal computer card interface being adapted to provide an interface between the personal computer card and a host microprocessor system.

90. The personal computer card as set forth in claim 89, wherein the personal computer card interface is adapted to relay the digitized fetal heart-rate data to the host computer on a real-time basis as the fetal heart-rate signal is converted by the signal conditioning circuitry.

91. The personal computer card as set forth in claim 89, wherein:

the personal computer card comprises a personal computer card housing;

the fetal heart-rate signal receiver is coupled to the personal computer card housing; the signal-conditioning circuitry is operatively coupled to the fetal heart-rate signal receiver; and the personal computer card interface is disposed within the personal computer card housing.

92. The personal computer card as set forth in claim 89, wherein the fetal heart-rate sensor is coupled to the fetal heart-rate signal receiver, the fetal heart-rate sensor being adapted to be placed into close proximity with a patient, to output a fetal heart-rate signal and to relay the fetal heart-rate signal to the fetal heart-rate receiver.

93. A personal computer card for collecting biological data, comprising:

a contraction signal receiver, the contraction signal receiver being adapted to receive a contraction signal from a contraction sensor and further being adapted to output the contraction signal;

signal-conditioning circuitry operatively coupled to the contraction signal receiver, the signal-conditioning circuitry being adapted to receive the contraction signal from the contraction signal receiver and to convert the contraction signal into digitized contraction data; and a personal computer card interface operatively coupled to the signal-conditioning circuitry, the personal computer card interface being adapted to provide an interface between the personal computer card and a host microprocessor system.

94. The personal computer card as set forth in claim 93, wherein the personal computer card interface is adapted to relay the digitized contraction data to the host computer on a real-time basis as the contraction signal is converted by the signal conditioning circuitry.

95. The personal computer card as set forth in claim 93, wherein:

the personal computer card comprises a personal computer card housing;

the contraction signal receiver is coupled to the personal computer card housing;

the signal-conditioning circuitry is operatively coupled to the contraction signal receiver; and the personal computer card interface is disposed within the personal computer card housing.

96. The personal computer card as set forth in claim 93, wherein the contraction sensor is coupled to the contraction signal receiver, the contraction sensor being adapted to be placed into close proximity with a patient, to output a contraction signal and to relay the contraction signal to the contraction receiver.

97. A personal computer card for collecting biological data, comprising:
- a blood glucose signal receiver, the blood glucose signal receiver being adapted to receive a blood glucose signal from a blood glucose sensor and further being adapted to output the blood glucose signal;
- signal-conditioning circuitry operatively coupled to the blood glucose signal receiver, the signal-conditioning circuitry being adapted to receive the blood glucose signal from the blood glucose signal receiver and to output digitized blood glucose data; and
- a personal computer card interface operatively coupled to the signal-conditioning circuitry, the personal computer card interface being adapted to provide an interface between the personal computer card and a host microprocessor system.

98. The personal computer card as set forth in claim 97, wherein the personal computer card interface is adapted to relay the digitized blood glucose data to the host computer on a real-time basis as the digitized blood glucose data is output by the signal-conditioning circuitry.

99. The personal computer card as set forth in claim 97, wherein:
- the personal computer card comprises a personal computer card housing;
- the blood glucose signal receiver is coupled to the personal computer card housing;
- the signal-conditioning circuitry is operatively coupled to the blood glucose signal receiver; and
- the personal computer card interface is disposed within the personal computer card housing.

100. The personal computer card as set forth in claim 97, wherein:
- the blood glucose sensor comprises a non-invasive blood glucose sensor; and
- the blood glucose sensor is coupled to the blood glucose signal receiver, the blood glucose sensor being adapted to be placed into close proximity with a patient, to output a blood glucose signal and to relay the blood glucose signal to the blood glucose signal receiver.

101. A personal computer card for collecting biological data, comprising:
- a blood cholesterol signal receiver, the blood cholesterol signal receiver being adapted to receive a blood cholesterol signal from a blood cholesterol sensor and further being adapted to output the blood cholesterol signal;
- signal-conditioning circuitry operatively coupled to the blood cholesterol signal receiver, the signal-conditioning circuitry being adapted to receive the blood cholesterol signal from the blood cholesterol signal receiver and to output digitized blood cholesterol data; and
- a personal computer card interface operatively coupled to the signal-conditioning circuitry, the personal computer card interface being adapted to provide an interface between the personal computer card and a host microprocessor system.

102. The personal computer card as set forth in claim 101, wherein the personal computer card interface is adapted to relay the digitized blood cholesterol data to the host computer on a real-time basis as the digitized blood cholesterol data is output by the signal-conditioning circuitry.

103. The personal computer card as set forth in claim 101, wherein:
- the personal computer card comprises a personal computer card housing;
- the blood cholesterol signal receiver is coupled to the personal computer card housing;
- the signal-conditioning circuitry is operatively coupled to the blood cholesterol signal receiver; and
- the personal computer card interface is disposed within the personal computer card housing.

104. The personal computer card as set forth in claim 101, wherein:
- the blood cholesterol sensor comprises a non-invasive blood cholesterol sensor; and
- the blood cholesterol sensor is coupled to the blood cholesterol signal receiver, the blood cholesterol sensor being adapted to be placed into close proximity with a patient, to output a blood cholesterol signal and to relay the blood cholesterol signal to the blood cholesterol signal receiver.

105. A personal computer card for collecting biological data, comprising:
- an oxygen signal receiver, the oxygen signal receiver being adapted to receive oxygen signal from an oxygen sensor and further being adapted to output the oxygen signal;
- a carbon-dioxide signal receiver, the carbon-dioxide signal receiver being adapted to receive a carbon-dioxide signal from a carbon-dioxide sensor and further being adapted to output the carbon-dioxide signal;
- a nitrogen signal receiver, the nitrogen signal receiver being adapted to receive a nitrogen signal from a nitrogen sensor and further being adapted to output the nitrogen signal;
- signal-conditioning circuitry operatively coupled to at least one of the oxygen signal receiver, the carbon-dioxide signal receiver and the nitrogen signal receiver, the signal-conditioning circuitry comprising at least one analog-to-digital converter and being adapted to output at least one digital signal; and
- a personal computer card interface operatively coupled to the signal-conditioning circuitry, the personal computer card interface being adapted to provide an interface between the personal computer card and a host microprocessor system.

106. The personal computer card as set forth in claim 105, wherein the personal computer card interface is adapted to relay the at least one digital signal to the host microprocessor system on a real-time basis as the at least one digital signal is output by the signal-conditioning circuitry.

107. The personal computer card as set forth in claim 105, wherein:
- the personal computer card comprises a personal computer card housing;
- the oxygen signal receiver is coupled to the personal computer card housing;
- the carbon-dioxide signal receiver is coupled to the personal computer card housing;
- the nitrogen signal receiver is coupled to the personal computer card housing;
- the signal-conditioning circuitry is operatively coupled to at least one of the oxygen signal receiver, the carbon-dioxide signal receiver and the nitrogen signal receiver; and the personal computer card interface is disposed within the personal computer card housing.

108. The personal computer card as set forth in claim 105, wherein:

the oxygen sensor comprises a non-invasive oxygen sensor;

the oxygen sensor is coupled to the oxygen signal receiver, the oxygen sensor being adapted to be placed close proximity with a patient, to output an oxygen signal and to relay the oxygen signal to the oxygen signal receiver;

the carbon-dioxide sensor comprises a non-invasive carbon-dioxide sensor;

the carbon-dioxide sensor is coupled to the carbon-dioxide signal receiver, the carbon-dioxide sensor being adapted to be placed into close proximity with a patient, to output a carbon-dioxide signal and to relay the carbon-dioxide signal to the carbon-dioxide signal receiver;

the nitrogen sensor comprises a non-invasive nitrogen sensor; and the nitrogen sensor is coupled to the nitrogen signal receiver, the nitrogen sensor being adapted to be placed into close proximity with a patient, to output a nitrogen signal and to relay the nitrogen signal to the nitrogen signal receiver.

109. The personal computer card as set forth in claim 105, wherein:

the personal computer card further comprises a carbon-monoxide signal receiver, the carbon-monoxide signal receiver being adapted to receive a carbon-monoxide signal from a carbon-monoxide sensor and further being adapted to output the carbon-monoxide signal;

the signal-conditioning circuitry is operatively coupled to at least one of the oxygen signal receiver, the carbon-dioxide signal receiver, the nitrogen signal receiver and the carbon-dioxide signal receiver.

110. A personal computer card for collecting biological data, comprising:

a carbon dioxide receiver, the carbon dioxide signal receiver being adapted to receive a carbon dioxide signal from a carbon dioxide sensor and further being adapted to output the carbon dioxide signal;

signal-conditioning circuitry operatively coupled to the carbon dioxide signal receiver, the signal-conditioning circuitry being adapted to receive the carbon dioxide signal from the carbon dioxide signal receiver and to output digitized carbon dioxide data; and a personal computer card interface operatively coupled to the signal-conditioning circuitry, the personal computer card interface being adapted to provide an interface between the personal computer card and a host microprocessor system.

111. The personal computer card as set forth in claim 110, wherein the personal computer card interface is adapted to relay the digitized carbon dioxide data to the host computer on a real-time basis as the digitized carbon dioxide data is output by the signal-conditioning circuitry.

112. The personal computer card as set forth in claim 110, wherein:

the personal computer card comprises a personal computer card housing;

the carbon dioxide signal receiver is coupled to the personal computer card housing;

the signal-conditioning circuitry is operatively coupled to the carbon dioxide signal receiver; and the personal computer card interface is disposed within the personal computer card housing.

113. The personal computer card as set forth in claim 110, wherein:

the carbon dioxide sensor comprises a non-invasive carbon dioxide sensor; and the carbon dioxide sensor is coupled to the carbon dioxide signal receiver, the oxygen sensor being adapted to be placed into close proximity with a patient, to output a carbon dioxide signal and to relay the carbon dioxide signal to the carbon dioxide signal receiver.

114. A personal computer card for collecting biological data, comprising:

a nitrogen receiver, the nitrogen signal receiver being adapted to receive a nitrogen signal from a nitrogen sensor and further being adapted to output the nitrogen signal;

signal-conditioning circuitry operatively coupled to the nitrogen signal receiver, the signal-conditioning circuitry being adapted to receive the nitrogen signal from the nitrogen signal receiver and to output digitized nitrogen data; and a personal computer card interface operatively coupled to the signal-conditioning circuitry, the personal computer card interface being adapted to provide an interface between the personal computer card and a host microprocessor system.

115. The personal computer card as set forth in claim 114, wherein the personal computer card interface is adapted to relay the digitize nitrogen data to the host computer on a real-time basis as the digitized nitrogen data is output by the signal-conditioning circuitry.

116. The personal computer card as set forth in claim 114, wherein:

the personal computer card comprises a personal computer card housing;

the nitrogen signal receiver is coupled to the personal computer card housing;

the signal-conditioning circuitry is operatively coupled to the nitrogen signal receiver; and the personal computer card interface is disposed within the personal computer card housing.

117. The personal computer card as set forth in claim 114, wherein:

the nitrogen sensor comprises a non-invasive nitrogen sensor; and the nitrogen sensor is coupled to the nitrogen signal receiver, the nitrogen sensor being adapted to be placed into close proximity with a patient, to output a nitrogen signal and to relay the nitrogen signal to the nitrogen signal receiver.

118. A personal computer card for collecting biological data, comprising:

a carbon monoxide receiver, the carbon monoxide signal receiver being adapted to receive a carbon monoxide signal from a carbon monoxide sensor and further being adapted to output the carbon monoxide signal;

signal-conditioning circuitry operatively coupled to the carbon monoxide signal receiver, the signal-conditioning circuitry being adapted to receive the carbon monoxide signal from the carbon monoxide signal receiver and to output digitized carbon monoxide data; and a personal computer card interface operatively coupled to the signal-conditioning circuitry, the personal computer card interface being adapted to provide an interface between the personal computer card and a host microprocessor system.

119. The personal computer card as set forth in claim 118, wherein the personal computer card interface is adapted to relay the digitized carbon monoxide data to the host computer on a real-time basis as the digitized carbon monoxide data is output by the signal-conditioning circuitry.

120. The personal computer card as set forth in claim 118, wherein:
the personal computer card comprises a personal computer card housing;
the carbon monoxide signal receiver is coupled to the personal computer card housing;
the signal-conditioning circuitry is operatively coupled to the carbon monoxide signal receiver; and
the personal computer card interface is disposed within the personal computer card housing.

121. The personal computer card as set forth in claim 118, wherein:
the carbon monoxide sensor comprises a non-invasive carbon monoxide sensor; and the carbon monoxide sensor is coupled to the carbon monoxide signal receiver, the carbon monoxide sensor being adapted to be placed into close proximity with a patient, to output a carbon monoxide signal and to relay the carbon monoxide signal to the carbon monoxide signal receiver.

122. A personal computer card for collecting biological data, comprising:
an oxygen signal receiver, the oxygen signal receiver being adapted to receive an oxygen signal from an oxygen sensor and further being adapted to output the oxygen signal;
signal-conditioning circuitry operatively coupled to the oxygen signal receiver, the signal-conditioning circuitry being adapted to receive the oxygen signal from the oxygen signal receiver and to output digitized oxygen data; and
a personal computer card interface operatively coupled to the signal-conditioning circuitry, the personal computer card interface being adapted to provide an interface between the personal computer card and a host microprocessor system.

123. The personal computer card as set forth in claim 122, wherein the personal computer card interface is adapted to relay the digitized oxygen data to the host microprocessor system on a real-time basis as the digitized oxygen data is output by the signal-conditioning circuitry.

124. The personal computer card as set forth in claim 122, wherein:
the personal computer card comprises a personal computer card housing;
the oxygen signal receiver is coupled to the personal computer card housing;
the signal-conditioning circuitry is operatively coupled to the oxygen signal receiver; and
the personal computer card interface is disposed within the personal computer card housing.

125. The personal computer card as set forth in claim 122, wherein the oxygen sensor is coupled to the oxygen signal receiver, the oxygen sensor being adapted to be placed into close proximity with a patient, to output an oxygen signal and to relay the oxygen signal to the oxygen signal receiver.

126. A personal computer card for collecting biological data, comprising:

a first conductor signal receiver, the first conductor signal receiver being adapted to receive a first conductor signal from a first conductor, the first conductor being adapted to be placed into close proximity with a patient;
a second conductor signal receiver, the second conductor signal receiver being adapted to receive a second conductor signal from a second conductor, the second conductor being adapted to be placed into close proximity with a patient;
signal-conditioning circuitry operatively coupled to the first conductor signal receiver and the second conductor receiver, the signal-conditioning circuitry being adapted to receive the first conductor signal from the first conductor signal receiver and being adapted to receive the second conductor signal from the second conductor signal receiver; and
a personal computer card interface operatively coupled to the signal-conditioning circuitry, the personal computer card interface being adapted to provide an interface between the personal computer card and a host microprocessor system.

127. The personal computer card for collecting biological data as set forth in claim 126, and further comprising:
a current source adapted to apply a predetermined current to at least one of the first conductor signal receiver and the second conductor signal receiver; and
an electrical resistance detector, the electrical resistance detector being adapted to determine an electrical resistance of the patient, based on the predetermined current applied by the current source.

128. The personal computer card as set forth in claim 127, wherein the electrical resistance detector is adapted to determine a body composition of the patient.

129. The personal computer card as set forth in claim 128, wherein the body composition of the patient comprises a fat composition of the patient.

130. The personal computer card as set forth in claim 128, wherein the personal computer card interface is adapted to relay the electrical resistance to the host microprocessor system on a real-time basis as the electrical resistance detector determines the electrical resistance of the patient.

131. The personal computer card as set forth in claim 127, wherein:
the personal computer card comprises a personal computer card housing;
the current source is coupled to the personal computer card housing;
the electrical resistance detector is operatively coupled to the personal computer card housing; and
the personal computer card interface is disposed within the personal computer card housing.

132. The personal computer card as set forth in claim 127, wherein:
the first conductor is coupled to the first conductor signal receiver, the first conductor being adapted to be placed into close proximity with a patient; are coupled to the ECG signal receiver, the plurality of ECG sensors being adapted to be placed into close proximity with a patient, to output ECG signals and to relay the ECG signals to the ECG signal receiver.

133. The personal computer card for collecting biological data as set forth in claim 126, wherein:
at least one of the first conductor signal receiver and the second conductor signal receiver is adapted to receive a predetermined current from a current source on the host microprocessor system; and an electrical resistance between the first conductor signal receiver and the second conductor signal receiver can be determined by an electrical resistance detector on the host microprocessor system, the electrical resistance detector being adapted to determine an electrical resistance of the patient, based on the predetermined current applied by the current source.

134. A personal computer card for collecting biological data, comprising:

a heart-beat signal receiver, the heart beat signal receiver being adapted to receive a heart beat signal from a heart beat sensor and further being adapted to output the heart beat signal;

signal-conditioning circuitry operatively coupled to the heart beat signal receiver, the signal-conditioning circuitry comprising at least one analog-to-digital converter and being adapted to output at least one digital signal; and a personal computer card interface operatively coupled to the signal-conditioning circuitry, the personal computer card interface being adapted to provide an interface between the personal computer card and a host microprocessor system.

135. The personal computer card as set forth in claim 134, wherein the personal computer card interface is adapted to relay the at least one digital signal to the host microprocessor system on a real-time basis as the at least one digital signal is output by the signal-conditioning circuitry.

136. The personal computer card as set forth in claim 134, wherein;

the personal computer card comprises a personal computer card housing;

the heart-beat signal receiver is coupled to the personal computer card housing;

the signal-conditioning circuitry is operatively coupled to the heart-beat signal receiver; and the personal computer card interface is disposed within the personal computer card housing.

137. The personal computer card as set forth in claim 134, wherein the heart-beat sensor is coupled to the heart-beat signal receiver, the heart-beat sensor being adapted to be placed into close proximity with a patient, to output a heart-beat signal and to relay the heart-beat signal to the heart-beat signal.

138. A personal computer card for collecting biological data, comprising:

an ear probe signal receiver, the ear probe signal receiver being adapted to receive an ear probe signal from an ear probe sensor and further being adapted to output the ear probe signal;

signal-conditioning circuitry operatively coupled to the ear probe signal receiver, the signal-conditioning circuitry comprising at least one analog-to-digital converter and being adapted to output at least one digital signal; and a personal computer card interface operatively coupled to the signal-conditioning circuitry, the personal computer card interface being adapted to provide an interface between the personal computer card and a host microprocessor system.

139. The personal computer card as set forth in claim 138, wherein the personal computer card interface is adapted to relay the at least one digital signal to the host microprocessor system on a real-time basis as the at least one digital signal is output by the signal-conditioning circuitry.

140. The personal computer card as set forth in claim 138, wherein:

the personal computer card comprises a personal computer card housing;

the ear probe signal receiver is coupled to the personal computer card housing;

the signal-conditioning circuitry is operatively coupled to the ear probe signal receiver; and the personal computer card interface is disposed within the personal computer card housing.

141. The personal computer card as set forth in claim 138, wherein the ear probe sensor is coupled to the ear probe signal receiver, the ear probe sensor being adapted to be placed into close proximity with a patient, to output an ear probe signal and to relay the ear probe signal to the ear probe signal receiver.

142. The personal computer card as set forth in claim 141, wherein:

the ear probe sensor comprises a hand-held wand adapted to be placed into an ear of a patient; and the ear probe sensor is adapted to measure a pressure of an eardrum of the patient.

143. A personal computer card for collecting biological data, comprising:

a pencil probe signal receiver, the pencil probe signal receiver being adapted to receive a pencil probe signal from a pencil probe sensor and further being adapted to output the pencil probe signal;

signal-conditioning circuitry operatively coupled to the pencil probe signal receiver, the signal-conditioning circuitry comprising at least one analog-to-digital converter and being adapted to output at least one digital signal; and a personal computer card interface operatively coupled to the signal-conditioning circuitry, the personal computer card interface being adapted to provide an interface between the personal computer card and a host microprocessor system.

144. The personal computer card as set forth in claim 143, wherein the personal computer card interface is adapted to relay the at least one digital signal to the host microprocessor system on a real-time basis as the at least one digital signal is output by the signal-conditioning circuitry.

145. The personal computer card as set forth in claim 143, wherein:

the personal computer card comprises a personal computer card housing;

the pencil probe signal receiver is coupled to the personal computer card housing;

the signal-conditioning circuitry is operatively coupled to the pencil probe signal receiver; and the personal computer card interface is disposed within the personal computer card housing.

146. The personal computer card as set forth in claim 143, wherein the pencil probe sensor is coupled to the pencil probe signal receiver, the pencil probe sensor being adapted to be placed into close proximity with a patient, to output a pencil probe signal and to relay the pencil probe signal to the pencil probe signal receiver.

147. The personal computer card as set forth in claim 146, wherein:

the pencil probe sensor comprises a hand-held wand adapted to emit acoustical signals; and the pencil probe sensor is adapted to measure a blood flow of the patient, based upon the emitted acoustical signals.

148. A personal computer card for collecting biological data, comprising:

an electroencephalograhy (EEG) signal receiver, the EEG signal receiver being adapted to receive EEG signals from a plurality of EEG sensors and further being adapted to output the EEG signals;

signal-conditioning circuitry operatively coupled to the EEG signal receiver, the signal-conditioning circuitry comprising at least one analog-to-digital converter and being adapted to output at least one digital signal; and a personal computer card interface operatively coupled to the signal-conditioning circuitry, the personal computer card interface being adapted to provide an interface between the personal computer card and a host microprocessor system and to relay the at least one digital signal to the host microprocessor system on a real-time basis as the at least one digital signal is output by the signal-conditioning circuitry.

149. The personal computer card as set forth in claim 148, wherein:

the personal computer card comprises a personal computer card housing;

the EEG signal receiver is coupled to the personal computer card housing;

the signal-conditioning circuitry is operatively coupled the EEG signal receiver; and the personal computer card interface is disposed within the personal computer card housing.

150. The personal computer card as set forth in claim 148, wherein the plurality of EEG sensors are coupled to the EEG signal receiver, the plurality of EEG sensors being adapted to be placed into close proximity with a patient, to output EEG signals and to relay the EEG signals to the EEG signal receiver.

151. A portable biological data collection device, comprising:

a personal computer card housing;

a biological data receiver coupled to the personal computer card housing, the biological data receiver being adapted to receive biological data and to output the biological data;

signal-conditioning circuitry operatively coupled to the biological data receiver, the signal-conditioning circuitry being adapted to receive the biological data from the biological data receiver and to convert the biological data into digitized biological data; and a personal computer card interface disposed within the personal computer card housing, the personal computer card interface being adapted to communicate with a set-top box and to relay the digitized biological data to the set-top box on a real-time basis as the biological data is converted by the signal conditioning circuitry.

152. The portable biological data collection device as set forth in claim 151, wherein:

the set-top box comprises a host microprocessor system; and the personal computer card interface is adapted to relay the digitized biological data to the set-top box on a real-time basis for transmission by the set-top box to another host microprocessor system.

153. A portable biological data collection device, comprising:

a game-set card housing;

a biological data receiver coupled to the game-set card housing, the biological data receiver being adapted to receive biological data and to output the biological data;

signal-conditioning circuitry operatively coupled to the biological data receiver, the signal-conditioning circuitry being adapted to receive the biological data from the biological data receiver and to convert the biological data into digitized biological data; and a game-set card interface disposed within the game-set card housing, the game-set card interface being adapted to communicate with a game-set and to relay the digitized biological data to the game-set on a real-time basis as the biological data is converted by the signal conditioning circuitry.

154. The portable biological data collection device as set forth in claim 153, wherein:

the game-set card housing comprises a personal computer card housing; and the game-set card interface comprises a personal computer card interface.

155. The host microprocessor system as set forth in claim 153, wherein the game-set card housing comprises a compact flush card housing.

156. A portable biological data collection device, comprising:

a computer card housing;

a biological data receiver coupled to the computer card housing, the biological data receiver being adapted to receive biological data and to output the biological data;

signal-conditioning circuitry operatively coupled to the biological data receiver, the signal-conditioning circuitry being adapted to receive the biological data from the biological data receiver and to convert the biological data into digitized biological data; and a compact flash card interface disposed within the computer card housing, the compact flash card interface being adapted to communicate with a host microprocessor system and to relay the digitized biological data to the host microprocessor system on a real-time basis as the biological data is converted by the signal conditioning circuitry.

157. A host microprocessor system configurable among a plurality of biological data collection device modes, comprising:

a personal computer card slot adapted to receive a personal computer card therein;

a personal computer card interface adapted to communicate with a personal computer card inserted into the personal computer card slot and adapted to receive digitized biological data from a personal computer card inserted into the personal computer card slot;

a microprocessor;

a data bus operatively connected between the microprocessor and the personal computer card interface;

an input device adapted to receive designation data from a personal computer card within the personal computer card slot, the input device being operatively connected to the microprocessor and the designation data being indicative of a type of the digitized biological data from a personal computer card inserted into the personal computer card slot, the designation data comprising one of a first identifier and a second identifier, the first identifier indicating that the digitized biological data should be interpreted by the microprocessor as first biological data and the second identifier indicating that the digitized biological data should be interpreted by the microprocessor as second biological data; and a configurer adapted to configure the host microprocessor system into a first real-time biological data collecting and analyzing device upon receipt of the first identifier, and adapted to configure the host microprocessor system into a second real-time biological data collecting and analyzing device upon receipt of the second identifier, the configurer being operatively connected to the microprocessor.

158. The host microprocessor system as set forth in claim 157, the designation data comprising a third identifier indicating that the digitized biological data should be interpreted by the microprocessor as third biological data, and the host microprocessor system being configurable into a third real-time biological data collecting and analyzing device.

159. The host microprocessor system as set forth in claim 157, wherein:

the host microprocessor system comprises a set-top box; and the set-top box is adapted to receive the digitized biological data and to transmit the digitized biological data to at least one other host microprocessor system.

160. The host microprocessor system as set forth in claim 159, wherein the set-top box is adapted to transmit the digitized biological data real-time to the at least one other host microprocessor system.

161. The host microprocessor system as set forth in claim 159, wherein the set-top box is adapted to transmit the digitized biological data to the at least one other host microprocessor system at a later time either automatically at predetermined intervals or upon transmit instructions.

162. The host microprocessor system as set forth in claim 157, wherein the host microprocessor system comprises a game set.

163. The host microprocessor system as set forth in claim 157, wherein:

the personal computer card slot is adapted to receive a compact flash card therein;

the personal computer card interface is adapted to communicate with a compact flash card inserted into the personal computer card slot.

* * * * *